US012593837B2

(12) United States Patent
Netzer et al.

(10) Patent No.: US 12,593,837 B2
(45) Date of Patent: Apr. 7, 2026

(54) RETINAL PIGMENT EPITHELIUM CELL COMPOSITIONS

(71) Applicant: Cell Cure Neurosciences Ltd., Jerusalem (IL)

(72) Inventors: Nir Netzer, Mazkeret Batya (IL); Ofer Wiser, Jerusalem (IL); Bat Shahaf, Jerusalem (IL); Orit Gamburg, Modiin-Maccabim-Reut (IL); Lior Rosenberg Belmaker, Jerusalem (IL); Dana Hayoun Neeman, Kibbutz Nachshon (IL); Osnat Bohana Kashtan, Jerusalem (IL)

(73) Assignee: Cell Cure Neurosciences Ltd. (IL)

( * ) Notice: Subject to any disclaimer, the term of this patent is extended or adjusted under 35 U.S.C. 154(b) by 409 days.

(21) Appl. No.: 16/958,399

(22) PCT Filed: Dec. 28, 2018

(86) PCT No.: PCT/IB2018/001579

§ 371 (c)(1),
(2) Date: Jun. 26, 2020

(87) PCT Pub. No.: WO2019/130061

PCT Pub. Date: Jul. 4, 2019

(65) Prior Publication Data

US 2021/0000102 A1 Jan. 7, 2021

Related U.S. Application Data

(60) Provisional application No. 62/612,210, filed on Dec. 29, 2017.

(51) Int. Cl.

| | |
|---|---|
| ***A01N 1/125*** | (2025.01) |
| ***A61K 9/00*** | (2006.01) |
| ***A61K 35/30*** | (2015.01) |
| ***A61K 47/02*** | (2006.01) |
| ***A61K 47/18*** | (2017.01) |
| ***A61K 47/20*** | (2006.01) |
| ***A61K 47/26*** | (2006.01) |

(52) U.S. Cl.

CPC ............ *A01N 1/125* (2025.01); *A61K 9/0048* (2013.01); *A61K 35/30* (2013.01); *A61K 47/02* (2013.01); *A61K 47/183* (2013.01); *A61K 47/20* (2013.01); *A61K 47/26* (2013.01)

(58) Field of Classification Search

CPC .............................. A01N 1/0221; A01N 1/122

See application file for complete search history.

(56) References Cited

U.S. PATENT DOCUMENTS

| | | | |
|---|---|---|---|
| 3,791,932 | A | 2/1974 | Schuurs et al. |
| 3,839,153 | A | 10/1974 | Schuurs et al. |
| 3,850,578 | A | 11/1974 | Mcconnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,666,828 | A | 5/1987 | Gusella |
| 4,683,202 | A | 7/1987 | Mullis |
| 4,801,531 | A | 1/1989 | Frossard |
| 4,879,219 | A | 11/1989 | Wands et al. |
| 5,011,771 | A | 4/1991 | Bellet et al. |
| 5,192,659 | A | 3/1993 | Simons |
| 5,272,057 | A | 12/1993 | Smulson et al. |
| 5,281,521 | A | 1/1994 | Trojanowski et al. |
| 5,405,742 | A | 4/1995 | Taylor |
| 5,755,785 | A | 5/1998 | Rowsey et al. |
| 5,843,780 | A | 12/1998 | Thomson |
| 5,854,015 | A | 12/1998 | Garnett et al. |
| 5,941,250 | A | 8/1999 | Aramant et al. |
| 5,962,027 | A | 10/1999 | Hughes |
| 6,045,791 | A | 4/2000 | Liu |
| 6,090,622 | A | 7/2000 | Gearhart et al. |

(Continued)

FOREIGN PATENT DOCUMENTS

| | | |
|---|---|---|
| CN | 101724602 A | 6/2010 |
| CN | 102618497 A | 8/2012 |

(Continued)

OTHER PUBLICATIONS

Baust et al. (Cryobiology 45: 97-108, 2002).*
Ni et al. (Current Molecular Medicine 2017, 17, 637-646).*
Hoang et al. (J. of Ocular Pharmacology and Therapeutics, 37 (8): 441-451, 2021).*
Srinivasan et al. (Apr. 2015) "TEER Measurement Techniques for In Vitro Barrier Model Systems", Journal of Laboratory Automation, 20(2):107-126 (35 pages).
Subrizi et al. (Aug. 11, 2012) "Generation of hESC-Derived Retinal Pigment Epithelium on Biopolymer Coated Polyirnide Membranes", Biomaterials, 33(32):8047-8054.
(Apr. 5, 2022) CryoStor: Optimized Freeze Media for Cells and Tissues, Biolife Solutions, pp. 1-2.

(Continued)

*Primary Examiner* — Bong-Sook Baek
(74) *Attorney, Agent, or Firm* — McNeill PLLC

(57) ABSTRACT

Presented herein are ready to administer (RTA) retinal pigment epithelium (RPE) cell therapy compositions for the treatment of retinal degenerative diseases and injuries. A method of formulating human RPE cells for administration to a subject directly after thawing and of formulating RPE cell therapy compositions for cryopreservation and administration of the cryopreserved composition to a subject subsequent to thawing are also presented. In another aspect, the RTA composition may be formulated as a thaw and inject (TAI) composition, whereby the composition is administered by injection subsequent to thawing.

18 Claims, 19 Drawing Sheets

(56) References Cited

U.S. PATENT DOCUMENTS

| | | | |
|---|---|---|---|
| 6,632,666 B2 | 10/2003 | Baust et al. | |
| 6,921,633 B2 | 7/2005 | Baust et al. | |
| 8,268,303 B2 | 9/2012 | Klimanskaya et al. | |
| 8,956,866 B2 | 2/2015 | Idelson et al. | |
| 9,446,076 B2 | 9/2016 | Gaussin et al. | |
| 11,066,642 B2 | 7/2021 | Bohana-Kashtan et al. | |
| 11,891,622 B2 | 2/2024 | Bohana-Kashtan et al. | |
| 2009/0226955 A1 | 9/2009 | Elliot et al. | |
| 2011/0027333 A1 | 2/2011 | Idelson et al. | |
| 2011/0034422 A1 | 2/2011 | Kannan et al. | |
| 2012/0171295 A1 | 7/2012 | Abramson | |
| 2012/0258451 A1 | 10/2012 | Klimanskaya | |
| 2013/0149284 A1 | 6/2013 | Malcuit et al. | |
| 2013/0195806 A1 | 8/2013 | Gay et al. | |
| 2013/0196369 A1 | 8/2013 | Hikita et al. | |
| 2013/0331393 A1 | 12/2013 | Lewis et al. | |
| 2014/0186309 A1 | 7/2014 | Klassen et al. | |
| 2015/0079046 A1 | 3/2015 | Sinden et al. | |
| 2015/0118749 A1 | 4/2015 | Idelson et al. | |
| 2015/0150796 A1 | 6/2015 | Duggan et al. | |
| 2015/0159134 A1 | 6/2015 | Choudhary et al. | |
| 2015/0175956 A1* | 6/2015 | Elhofy | A01N 1/0226 435/404 |
| 2015/0175964 A1 | 6/2015 | Clegg et al. | |
| 2015/0368713 A1 | 12/2015 | Bharti et al. | |
| 2017/0079262 A1* | 3/2017 | Rowley | C12N 1/04 |
| 2018/0008458 A1 | 1/2018 | Banin et al. | |
| 2018/0011092 A1 | 1/2018 | Bohana-Kashtan et al. | |
| 2018/0016553 A1 | 1/2018 | Bohana-Kashtan et al. | |
| 2018/0216064 A1* | 8/2018 | Reubinoff | A61P 27/02 |
| 2018/0228846 A1 | 8/2018 | Bohana-Kashtan | |
| 2018/0230426 A1 | 8/2018 | Bohana-Kashtan et al. | |
| 2018/0312805 A1 | 11/2018 | Reubinoff et al. | |
| 2019/0030168 A1 | 1/2019 | Gay et al. | |
| 2020/0085882 A1 | 3/2020 | Cuzzani et al. | |
| 2021/0332325 A1 | 10/2021 | Bohana-Kashtan et al. | |
| 2021/0388316 A1 | 12/2021 | Bohana-Kashtan et al. | |
| 2022/0095608 A1 | 3/2022 | Netzer et al. | |
| 2022/0154141 A1 | 5/2022 | Bohana-Kashtan et al. | |
| 2022/0169981 A1 | 6/2022 | Bohana-Kashtan et al. | |
| 2022/0169982 A1 | 6/2022 | Bohana-Kashtan et al. | |
| 2022/0408719 A1 | 12/2022 | Netzer et al. | |
| 2023/0028133 A1 | 1/2023 | Banin et al. | |
| 2023/0051803 A1 | 2/2023 | Bohana-Kashtan et al. | |
| 2023/0119816 A1 | 4/2023 | Netzer et al. | |
| 2023/0310709 A1 | 10/2023 | Eitan et al. | |

FOREIGN PATENT DOCUMENTS

| | | | |
|---|---|---|---|
| CN | 104080464 | A | 10/2014 |
| CN | 105284787 | A | 2/2016 |
| CN | 105358679 | A | 2/2016 |
| CN | 107427534 | A | 12/2017 |
| EP | 2128244 | A1 | 12/2009 |
| EP | 2702135 | A2 | 3/2014 |
| EP | 3240892 | B9 | 7/2020 |
| GB | 2327675 | A | 2/1999 |
| JP | 2008017840 | A | 1/2008 |
| JP | 2009180811 | A | 8/2009 |
| JP | 2010524457 | A | 7/2010 |
| JP | 2014533289 | A | 12/2014 |
| JP | 2016512955 | A | 5/2016 |
| JP | 2018501281 | A | 1/2018 |
| JP | 2020511539 | A | 4/2020 |
| KR | 20100065373 | A | 6/2010 |
| KR | 20170049775 | A | 5/2017 |
| WO | 01/55114 | A1 | 8/2001 |
| WO | 02/060875 | A1 | 8/2002 |
| WO | 03/068233 | A1 | 8/2003 |
| WO | 2005/014549 | A1 | 2/2005 |
| WO | 2006/040763 | A2 | 4/2006 |
| WO | 2006/070370 | A2 | 7/2006 |
| WO | 2008129554 | A1 | 10/2008 |
| WO | 2011/063005 | A1 | 5/2011 |
| WO | 2011063005 | A2 | 5/2011 |
| WO | 2012149484 | A2 | 11/2012 |
| WO | 2013/074681 | A1 | 5/2013 |
| WO | 2013114360 | A1 | 8/2013 |
| WO | 2013184809 | A1 | 12/2013 |
| WO | 2014087244 | A2 | 6/2014 |
| WO | 2014/121077 | A1 | 8/2014 |
| WO | 2014121077 | A2 | 8/2014 |
| WO | 2015087231 | A1 | 6/2015 |
| WO | 2015175504 | A1 | 11/2015 |
| WO | 2016/108219 | A1 | 7/2016 |
| WO | 2016108239 | A1 | 7/2016 |
| WO | 2016108240 | A1 | 7/2016 |
| WO | 2017/021973 | A1 | 2/2017 |
| WO | 2017/072763 | A1 | 5/2017 |
| WO | 2018170494 | A1 | 9/2018 |
| WO | 2019130061 | A2 | 7/2019 |
| WO | 2022261320 | A1 | 12/2022 |

OTHER PUBLICATIONS (2022) Dulbecco's Modified Eagle's Medium (DMEM), Laboratory Notes, pp. 1-5.
(2022) Protic vs. Aprotic Solvents, Chemistry Score, pp. 1-4.
Ahmado et al., Invest Ophthalmol Vis Sci. (2011) 52(10):7148-7159.
Bharti et al., "The new paradigm: retinal pigment epithelium cells generated from embryonic or induced pluripotent stem cells", Pigment Cell Melanoma Res. 2010; 24(1): 21-34.
BioTime Annual Meeting Shareholder Update: Cell Cure NeuroSciences Ltd., Nov. 4, 2014, slides 55-76.
Brandl et al., "In-depth characterisation of retinal pigment epithelium, (RPE) cells derived from human induced pluripotent stem cells (hiPSC)", Neuromuscular Med. 2014; 16(3): 551-564.
Buchholz et al., "Derivation of functional retinal pigmented epithelium from induced pluripotent stem cells", Stem Cells. 2009; 27(10): 2427-2434.
Buchholz et al., "Rapid and Efficient Directed Differentiation of Human Pluripotent Stem Cells into Retinal Pigmented Epithelium", Stem Cells Transl Med. (2013) 2(5):384-393.
Buzhor et al., "Cell-based therapy approaches: the hope for incurable diseases", Regen Med. 2014; 9(5): 649-672.
Carr et al., "Protective effects of human iPS-derived retinal pigment epithelium cell transplantation in the retinal dystrophic rat", PLoS One. 2009; 4(12): e8152.
Deeg et al., "CRALBP is a highly prevalent autoantigen for human autoimmune uveitis", Clin Dev Immunol. 2007; 2007: 39245.
Evidence for publication date of D12 by the U.S. Securities and Exchange Commission (SEC).
FDA Guidance: Content and Review of Chemistry, Manufacturing, and Control (CMC) Information for Human Somatic Cell Therapy Investigational New Drug Applications (INDs), Apr. 2008.
Form 8-K, submitted to the SEC by BioTime on Nov. 4, 2014.
Harmonizome website extracts, "Pineal Body".
Idelson et al., "Directed differentiation of human embryonic stem cells into functional retinal pigment epithelium cells", Cell Stem Cell. 2009; 5(4): 396-408 (incl. Supplemental Date, filed only by O2).
Kamao et al., "Characterization of Human Induced Pluripotent Stem Cell-Derived Retinal Pigment Epithelium Cell Sheets Aiming for Clinical Application", Stem Cell Reports. 2014; 2(2):205-218.
Kokkinaki et al., "Human Induced Pluripotent Stem-Derived Retinal Pigment Epithelium (RPE) Cells Exhibit Ion Transport, Membrane Potential, Polarized Vascular Endothelial Growth Factor Secretion, and Gene Expression Pattern Similar to Native RPE", Stem Cells. (2011) 29(5): 825-835.
Lane et al., "Engineering efficient retinal pigment epithelium differentiation from human pluripotent stem cells", Stem Cells Transl Med. 2014; 3(11): 1295-1304.
Maminishkis et al., 2006 "Confluent Monolayers of Cultured Human Fetal Retinal Pigment Epithelium Exhibit Morphology and Physiology of Native Tissue", Investigative Ophthalmology & Visual Science, 47(8):3612-3624.

(56) References Cited

OTHER PUBLICATIONS

Maruotti et al., Stem Cells Transl Med. (2013) 2(5):341-354 [including Table S4].
Mcgill et al., "Long-term efficacy of GMP grade xeno-free hESC-derived RPE cells following transplantation", Transl Vis Sci Technol. 2017; 6(3): 17.
MTeSR 1 product information sheet.
NCBI entry for "PMEL".
NCBI entry for "RLBP1".
Parvini et al., Mol Neurobiol. (2014) 50(2):597-612.
Patentee's letter dated Mar. 27, 2019.
Schwartz et al., Lancet. 2012, 379(9817):713-20 (inc. supplementary material).
SEC Directory Listing for BioTime's SEC submission, Nov. 4, 2014.
Vaajasaari et al., "Toward the defined and xeno-free differentiation of functional human pluripotent stem cell-derived retinal pigment epithelial cells", Mol Vis. 2011; 17: 558-575.
Watt et al., "PMEL: A pigment cell-specific model for functional amyloid formation", Pigment Cell Melanoma Res. 2013; 26(3): 300-315.
Zhu et al., Invest Ophthalmol Vis Sci. (2011) 52(3):1573-1585.
Tsai, T. et al. "Dimethyl sulphoxide dose-response on rat retinal function" Doc Ophthalmol (2009) 119: 199-207.
Pennington et al., Scientific Reports 11:6286 (2021).
Business Wire Press Release, "Lineage Established Exclusive Worldwide Collaboration with Genentech for the Development and Commercialization of OpRegen® RPE Cell Therapy for the Treatment of Ocular Disorders", Dec. 20, 2021 (5 pages).
International Preliminary Report on Patentability received for International Application No. PCT/IB2018/001579, mailed on Jul. 9, 2020, 18 Pages.
International Search Report and Written Opinion received for International Application No. PCT/IB2018/001579, mailed on Oct. 22, 2019, 21 pages.
Algvere et al. (Mar. 1997) "Transplantation of RPE in Age-related Macular Degeneration: Observations in Disciform Lesions and Dry RPE Atrophy", Graefe's Archive for Clinical and Experimental Ophthalmology, 235 (3):149-158.
Aoi et al. (Aug. 1, 2008) "Generation of Pluripotent Stem Cells from Adult Mouse Liver and Stomach Cells", Science, 321(5889):699-702.
Bigar et al. (Aug. 1992) "Corneal Transplantation", Current Opinion in Ophthalmology, 3(4):473-481.
Bongso et al. (Aug. 1989) "Improved Quality of Human Embryos when Co-Cultured with Human Ampullary Cells", Human Reproduction, 4(6):706-713.
Chacko et al. (Feb. 24, 2000) "Survival and Differentiation of Cultured Retinal Progenitors Transplanted in the Subretinal Space of the Rat", Biochemical and Biophysical Research Communications, 268(3):842-846.
Chung et al. (Feb. 7, 2008) "Human Embryonic Stem Cell Lines Generated without Embryo Destruction", Cell Stem Cell, 2(2):113-117.
Doetschman et al. (May 1988) "Establishment of Hamster Blastocyst-Derived Embryonic Stem (ES) Cells", Developmental Biology, 127(1):224-227.
Gardner et al. (Jan. 1998) "Culture and Transfer of Human Blastocysts Increases Implantation Rates and Reduces the Need for Multiple Embryo Transfers", Fertility and Sterility, 69(1):84-88.
Giles et al. (Oct. 1993) "Pluripotency of Cultured Rabbit Inner Cell Mass Cells Detected by Isozyme Analysis and Eye Pigmentation of Fetuses Following Injection into Blastocysts or Morulae", Molecular Reproduction and Development, 36(2):130-138.
Graves et al. (Dec. 1993) "Derivation and Characterization of Putative Pluripotential Embryonic Stem Cells from Preimplantation Rabbit Embryos", Molecular Reproduction and Development, 36(4):424-433.
Iannaccone et al. (May 1994) "Pluripotent Embryonic Stem Cells from the Rat Are Capable of Producing Chimeras", Developmental Biology, 163(1):288-292.
Kalkan et al. (Dec. 2014) "Mapping the Route From Naive Pluripotency to Lineage Specification", Philosophical Transactions Of The Royal Society B Biological Sciences, 20130540, 369(1657):10 pages.
Mitalipova et al. (2001) "Pluripotency of Bovine Embryonic Cell Line Derived from Precompacting Embryos", Cloning, 3(2):59-67.
Notarianni et al. (1991) "Derivation of Pluripotent, Embryonic Cell Lines from the Pig and Sheep", Journal of Reproduction and Fertility Supplement, 43:255-260.
Oplinger et al. (Apr. 1998)"A Comparison of Corneal Autografts With Homografts", Ophthalmic Surgery, Lasers and Imaging Retina, 29(4):305-308.
Park et al. (Jan. 10, 2008) "Reprogramming of Human Somatic Cells to Pluripotency With Defined Factors", Nature, 451(7175):141-146.
Patel et al. (Apr. 2000) "Indications for and Outcomes of Repeat Penetrating Keratoplasty, 1989-1995", Ophthalmology, 107(4):719-724.
Peyman et al. (Feb. 1991) "A Technique for Retinal Pigment Epithelium Transplantation for Age-related Macular Degeneration Secondary to Extensive Subfoveal Scarring", Ophthalmic Surgery, Lasers and Imaging Retina, 22(2):102-108 (9 pages).
Reubinoff et al. (Apr. 18, 2000) "Embryonic stem cell lines from human blastocysts: somatic differentiation in vitro", Nature Biotechnology, 18(4): 399-404.
Shamblott et al. (Nov. 1998) "Derivation of Pluripotent Stem Cells from Cultured Human Primordial Germ Cells", Proceedings of the National Academy of Sciences of the United States of America, 95(23): 13726-13731.
Sieving et al. (Mar. 7, 2006) "Ciliary Neurotrophic Factor (CNTF) for human retinal degeneration: Phase I Trial of CNTF Delivered by Encapsulated Cell Intraocular Implants", Proceedings of the National Academy of Sciences of the United States of America, 103(10):3896-3901.
Takahashi et al. (Nov. 30, 2007) "Induction of Pluripotent Stem Cells From Adult Human Fibroblasts by Defined Factors", Cell, 131(5):861-872.
Thomson et al. (Nov. 6, 1998) "Embryonic Stem Cell Lines Derived from Human Blastocysts", Science, , 282(5391):1145-1147.
Thomson et al. (Aug. 1995) "Isolation of a Primate Embryonic Stem Cell Line", Proceedings of the National Academy of Sciences of the United States of America, 92(17):7844-7848.
Thomson et al. (Aug. 1996) "Pluripotent Cell Lines Derived from Common Marmoset (Callithrix Jacchus) Blastocysts", Biology of Reproduction, 55(2):254-259.
Tsubota K (Nov.-Dec. 1999) "Ocular Surface Management in Corneal Transplantation, A Review", Japanese Journal of Ophthalmology, 43(6):502-508.
Wheeler Matthew B. (1994) "Development and Validation of Swine Embryonic Stem Cells: A Review", Reproduction, Fertility and Development, 6(5):563-568.
Yamanaka Shinya (Jun. 7, 2007) "Strategies And New Developments In The Generation Of Patient-Specific Pluripotent Stem Cells", Cell Stem Cell, 1(1):39-49.
Extended European Search Report issued in European Application No. 18893743.7, mailed on Aug. 10, 2021, 12 pages.
(Feb. 17, 2015) Cell Cure Neurosciences Ltd. Provides Update on its Product Development and Partnering Activities, 3 pages.
Extended European Search Report for Application No. EP 21215492.6, mailed on Apr. 8, 2022, 12 pages.
Extended European Search Report received for European Patent Application No. 15875361.6, mailed on May 5, 2018, 10 pages.
Extended European Search Report received in Europe Patent Application No. 19207191.8, Mailed on Mar. 18, 2020, 8 Pages.
Oct. 27, 2021, Extended European Search Report received in European Application No. 21170654.4, mailed on Oct. 27, 2021, 8 pages.
International Preliminary Report on Patentability received for International Application No. PCT/IL2015/051270, mailed on Jul. 13, 2017, 8 pages.

(56) References Cited

OTHER PUBLICATIONS

International Preliminary Report on Patentability received for PCT International Application No. PCT/IL2015/050456, mailed on Jul. 13, 2017, 11 pages.
International Preliminary Report on Patentability received for PCT Patent International Application No. PCT/IL15/51269, Mailed on Jul. 13, 2017, 9 Pages.
International Search Report and Written Opinion received for International Application No. PCT/IL2015/051270, mailed on Mar. 29, 2016, 11 pages.
International Search Report and Written Opinion received for PCT Patent International Application No. PCT/IL15/51269, Mailed on Mar. 24, 2016, 12 Pages.
International Search Report and Written Opinion Received for PCT Patent International Application No. PCT/IL2015/050456, mailed on Aug. 12, 2015, 14 pages.
Notice of Opposition received in European Patent Application No. 15832698.3, mailed on Mar. 28, 2022, 34 pages. (Strawman Opposition).
Notice of Opposition received in European Patent Application No. 15832698.3, mailed on Mar. 28, 2022, 68 pages. (Dixon Opposition).
Notice of Opposition received in European Patent Application No. 15875361.6, mailed on Sep. 23, 2021, 37 pages.
Notice of Opposition received in European Patent Application No. 15875361.6, mailed on Oct. 12, 2021 (Meissner Bolte Opposition), 47 pages.
Notice of Opposition received in European Patent Application No. 16795439.5, mailed on Jun. 2, 2022, 5 pages.
Notice of Opposition received in European Patent Application No. 15875361.6, mailed on Sep. 22, 2021, 45 pages.
Patentee's letter, dated Dec. 10, 2018, filed during examination of EP3240612, 4 pages.
(Apr. 13, 2015) Safety and Efficacy Study of OpRegen for Treatment of Advanced Dry-Form Age-Related Macular Degeneration, History of Changes for Study: NCT02286089, 10 pages.
(Feb. 5, 2019) Safety and Efficacy Study of OpRegen for Treatment of Advanced Dry-Form Age-Related Macular Degeneration, History of Changes for Study: NCT02286089, 12 pages.
(Nov. 5, 2014) Safety and Efficacy Study of OpRegen for Treatment of Advanced Dry-Form Age-Related Macular Degeneration, Accession No. NCT02286089, 5 pages.
Search Opinion issued in respect of EP3240612, mailed on dated May 11, 2018, 5 pages.
Amit et al. (Mar. 2004) "Feeder Layer- and Serum-Free Culture of Human Embryonic Stem Cells", Biology of Reproduction, 70(3):837-845.
Bae et al. (2012) "Hypoxia Enhances the Generation of Retinal Progenitor Cells from Human Induced Pluripotent and Embryonic Stem Cells", Stem Cells and Development, 21(8):1344-1355.
Beatty et al. (2000) "The Role of Oxidative Stress in the Pathogenesis of Age-related Macular Degeneration", Survey of Ophthalmology, 45(2):115-134.
Becerra et al. (Feb. 2004) "Pigment Epithelium-derived Factor in the Monkey Retinal Pigment Epithelium and Interphotoreceptor Matrix: Apical Secretion and Distribution", Experimental Eye Research, 78(2):223-234.
Blaauwgeers et al. (Aug. 1999) "Polarized Vascular Endothelial Growth Factor Secretion by Human Retinal Pigment Epithelium and Localization of Vascular Endothelial Growth Factor Receptors on the Inner Choriocapillaris. Evidence for a Trophic Paracrine Relation", The American Journal of Pathology, 155(2):421-428.
Brittan et al. (Mar. 1, 2007) "Bone marrow stem cell-mediated regeneration in IBD: where do we go from here?", Gastroenterology, 132(3):1171-1173.
Burdon et al. (1995), "A Survey of Corneal Graft Practice in the United Kingdom", Eye, 9(Suppl.):6-12.
Cantz Tobias "Declaration by Prof. Tobias Cantz", 13 pages.
Cao et al. (Nov. 2018) "Polarized Retinal Pigment Epithelium Generates Electrical Signals that Diminish with Age and Regulate Retinal Pathology", Journal of Cellular and Molecular Medicine, 22(11):5552-5564.
Cho et al. (May 16, 2012) "Generation of Retinal Pigment Epithelial Cells From Human Embryonic Stem Cell-Derived Spherical Neural Masses", Stem Cell Research, 9(2):101-109.
Clegg et al. (2013) "Derivation of Retinal Pigmented Epithelial Cells for the Treatment of Ocular Disease", Stem Cells Handbook, 411-418.
Dallas et al. (2008) "Transforming Growth Factor-β(Chapter 53)", Principles of Bone Biology (Third Edition), 11:1145-1166.
Du et al. (May 2011) "Induced Pluripotent Stem Cell Therapies for Geographic Atrophy of Age-Related Macular Degeneration", Seminars in Ophthalmology, 26(3):216-224.
Elliot et al. (Apr. 2006) "Retinal Pigment Epithelium Protection from Oxidant-Mediated Loss of MMP-2 Activation Requires Both MMP-14 and TIMP-2", Investigative Ophthalmology & Visual Science, 47(4):1696-1702.
Fronk et al. (2016) "Methods for Culturing Retinal Pigment Epithelial Cells: a Review of Current Protocols and Future Recommendations", Journal of Tissue Engineering, 7:1-23.
Garita-Hernandez et al. (May 2013) "Hypoxia Increases the Yield of Photoreceptors Differentiating from Mouse Embryonic Stem Cells and Improves the Modeling of Retinogenesis in Vitro", Stem Cells, 31(5):966-978.
GENBANK (Feb. 16, 2005) "*Homo sapiens* Genomic DNA, 21q Region, Clone: 289H18X26, Genomic Survey Sequence", Accession No. AG014699.1, 1 page.
Gropp et al. (2012) "Standardization of the Teratoma Assay for Analysis of Pluripotency of Human ES Cells and Biosafety of Their Differentiated Progeny", PLOS One, 7(9):1-10.
Galvao et al. (Mar. 2014) Unexpected Low-dose Toxicity of the Universal Solvent DMSO, The FASEB Journal, 28(3):1317-1330.
Hadasit Bio-Holdings Ltd. (2012) "OpRegen", Datasheet(Online), Hadasit Bio-Holding Ltd., Press Release (2012), 2 pages.
Hill et al. (Jan. 1975) Dimethyl Sulfoxide in the Treatment of Retinal Disease, Annals of the New York Academy of Sciences, 243(1):485-490 (9 pages).
Hrabovszky et al. (Apr. 1995) "Triple-labeling Method Combining Immunocytochemistry and in Situ Hybridization Histochemistry: Demonstration of Overlap Between Fos-immunoreactive and Galanin mRNA-expressing Subpopulations of Luteinizing Hormone-releasing Hormone Neurons in Female Rats", Journal of Histochemistry and Cytochemistry, 43(4):363-370.
Hsiung et al. (Jan. 2015) "Polarized Human Embryonic Stem Cell-derived Retinal Pigment Epithelial Cell Monolayers Have Higher Resistance to Oxidative Stress-induced Cell Death Than Nonpolarized Cultures", Stem Cells Translational Medicine, 4(1):10-20.
Idelson et al. "Directed Differentiation of Human Embryonic Stem Cells into Functional Retinal Pigment Epithelium Cells", Supplemental Data, Cell Stem Cell, 5:(Suppl.)1-10.
Jostock et al. (2001) "Soluble Gp130 is the Natural Inhibitor of Soluble Interleukin-6 Receptor Transsignaling Responses", European Journal of Biochemistry, 268:160-167.
Kamao et al. "Characterization of Human Induced Pluripotent Stem Cell-Derived Retinal Pigment Epithelium Cell Sheets Aiming for Clinical Application", Supplemental Information, Stem Cell Reports, 2:(Suppl.)1-25.
Kamao et al. (Jan. 2017) "Evaluation of the Surgical Device and Procedure for Extracellular Matrix-Scaffold-Supported Human iPSC-Derived Retinal Pigment Epithelium Cell Sheet Transplantation", Retinal Cell Biology, 58(1):211-220.
Krohne et al. (2012) "Generation of Retinal Pigment Epithelial Cells from Small Molecules and OCT4 Reprogrammed Human Induced Pluripotent Stem Cells", Stem Cells Translational Medicine, 1(2):96-109.
Laursen et al. (May 3, 2007) "Regional Differences in Expression of Specific Markers for Human Embryonic Stem Cells", Reproductive BioMedicine Online, 15(1):89-98.

(56) References Cited

OTHER PUBLICATIONS

Lu et al. (Sep. 2009) "Long-term Safety and Function of RPE From Human Embryonic Stem Cells in Preclinical Models of Macular Degeneration", Stem Cells, 27(9):2126-2135.
Lund et al. (2006) "Human Embryonic Stem Cell-Derived Cells Rescue Visual Function In Dystrophic RCS Rats", Cloning and Stem Cells, 8(3):189-199.
Masuda et al. (Aug. 27, 2010) "SOX9, through Interaction with Microphthalmia-associated Transcription Factor (MITF) and OTX2, Regulates BEST1 Expression in the Retinal Pigment Epithelium", The Journal of Biological Chemistry, 285(35):26933-26944.
Ohno-Matsui et al. (2005) "The Effects of Amniotic Membrane on Retinal Pigment Epithelial Cell Differentiation", Molecular Vision, 11:1-10.
Onnela et al. (Dec. 22, 2011) "Electric Impedance of Human Embryonic Stem Cell-Derived Retinal Pigment Epithelium", Medical & Biological Engineering & Computing, 50:107-116.
Patel et al. (2015) "Geographic Atrophy: Clinical Impact and Emerging Treatments", Ophthalmic Surgery, Lasers and Imaging Retina, 46(1):8-13.
Peng et al. (Jul. 2013) "Engineering a Blood-Retinal Barrier with Human Embryonic Stem Cell-Derived Retinal Pigment Epithelium: Transcriptome and Functional Analysis", Stem Cells Translational Medicine, 2(7):534-544.
Pennington et al. (Feb. 2015) "Defined Culture of Human Embryonic Stem Cells and Xeno-Free Derivation of Retinal Pigmented Epithelial Cells on a Novel, Synthetic Substrate", Stem Cells Translational Medicine, 4(2):165-177.
Pfeffer et al. (Sep. 2014) "Cell Culture of Retinal Pigment Epithelium: Special Issue", Experimental Eye Research, 126:1-4.
Press Release (Nov. 11, 2012) "Cell Cure Neurosciences Ltd. Receives Additional Financing From Bio Time Inc", Hadasit Bio-Holdings, 2 pages.
Press Release (Nov. 3, 2014) "Cell Cure Neurosciences Ltd. Receives FDA Authorization to Initiate Phase I/IIa Trial", Hadasit Bio-Holdings Ltd., 3 Pages.
Przybyla et al. (2012) "Probing Embryonic Stem Cell Autocrine and Paracrine Signaling Using Microfluidics", Annual Review of Analytical Chemistry, 5:293-315.
(1999) R&D Systems, "Interleukin 6", Datasheet(online), 4 pages.
Schwartz et al. (2015) "Human Embryonic Stem Cell-Derived Retinal Pigment Epithelium in Patients with Age-Related Macular Degeneration and Stargardt's Macular Dystrophy: Follow-Up of Two Open-Label Phase 1/2 Studies", Lancet, 385(9967):509-516.
Shi et al. (Oct. 2008) "Control of Chemokine Gradients by the Retinal Pigment Epithelium", Investigative Ophthalmology & Visual Science, 49(10):4620-4630.
Simo et al. (Feb. 17, 2010) "The Retinal Pigment Epithelium: Something More than a Constituent of the Blood-Retinal Barrier-Implications for the Pathogenesis of Diabetic Retinopathy", Journal of Biomedicine and Biotechnology, 2010:190724(15 pages).
Singh et al. (Oct. 2013) "Functional Analysis of Serially Expanded Human iPS Cell-Derived RPE Cultures", Investigative Opthamology and Visual Science, 54:6767-6778.
Skeie et al. (Feb. 23, 2011) "Angiogenin in Age-Related Macular Degeneration", Molecular Vision, 17:576-582.
Sonoda et al. (2010) "Attainment of Polarity Promotes Growth Factor Secretion by Retinal Pigment Epithelial Cells: Relevance to Age-related Macular Degeneration", Aging, 2(1):28-42.
Sperling Laurae. (2013) "Embryonic Stem Cell Therapy—From Bench to Bed", Pluripotent Stem Cells, Chapter 18, 18 pages.
Stout et al. (May 2011) "Surgical Approaches to Gene and Stem Cell Therapy for Retinal Disease", Human Gene Therapy, 22(5):531-535.
Strunnikova et al. (2010) "Transcriptome Analysis and Molecular Signature of Human Retinal Pigment Epithelium", Human Molecular Genetics, 19(12):2468-2486.
Tannenbaum et al. (Jun. 20, 2012) "Derivation of Xeno-Free and GMP-Grade Human Embryonic Stem Cells—Platforms for Future Clinical Applications", PLoS ONE, 7(6):e35325(16 pages).
Thomson et al. (1998) "Primate Embryonic Stem Cells", Current Topics in Developmental Biology, 38:133-165.
Vadlapatla et al. (2013) "Molecular Expression and Functional Activity of Efflux and Influx Transporters in Hypoxia Induced Retinal Pigment Epithelial Cells", International Journal of Pharmaceutics, 454(1):444-452.
Vugler et al. (Dec. 2008) "Elucidating the Phenomenon of HESC-Derived RPE: Anatomy of Cell Genesis, Expansion and Retinal Transplantation", Experimental Neurology, 214(2):347-361.
Wu et al. (Aug. 2011) "Induction and Testing of Hypoxia in Cell Culture", Journal of Visualized Experiments, 54:e2899(4 pages).
Xu et al. (Oct. 1, 2001) "Feeder-Free Growth of Undifferentiated Human Embryonic Stem Cells", Nature Biotechnology, 19:971-974.
Yamamoto et al. (2003) "Increased Soluble Interleukin-6 Receptor in Vitreous Fluid of Proliferative Vitreoretinopathy", Current Eye Research, 26(1):9-14.
Yang et al. (Jul. 28, 2021) "Functions and Diseases of the Retinal Pigment Epithelium", Frontiers in Pharmacology, 12(727870):1-7.
Yin et al. (Jul. 25, 2003) "The Effects of Different Intraocular Irrigating Solutions on the Apoptosis of Cultured RPE Cells", Graefe's Archive for Clinical and Experimental Opthalmology, 241(10):834-839.
Zhang et al. (2014) "Direct Conversion of Human Fibroblasts into Retinal Pigment Epithelium-Like Cells by Defined Factors", Protein Cell, 5(1):48-58.
Zhang et al. (2013) "Meeting Report-TGF-β Superfamily: Signaling in Development and Disease", Journal of Cell Science, 126(21):4809-4813.
Zhang et al. (2015) "Synergistic Protective Effects of Escin and Low dose Glucocorticoids against Vascular Endothelial Growth Factor induced Blood retinal Barrier Breakdown in Retinal Pigment Epithelial And Umbilical Vein Endothelial Cells", Molecular Medicine Reports, 11:1372-1377.
Zhu et al. (Jan. 2013) "Three-Dimensional Neuroepithelial Culture from Human Embryonic Stem Cells and Its Use for Quantitative Conversion to Retinal Pigment Epithelium", PLoS One, 8(1):e54552(13 pages).
Fishman, Gerald A. (Nov.-Dec. 2013) "A Historical Perspective on the Early Treatment of Night Blindness and the Use of Dubious and Unproven Treatment Strategies for Patients with Retinitis Pigmentosa", Survey of Ophthalmology, 58(6):652-663.
Garcia, Charles A. (1983) "Ocular Toxicology of Dimethyl Sulfoxide and Effects on Retinitis Pigmentosa", Annals of the New York Academy of Sciences, 411:48-51.
Kociok et al. (Aug. 1998) "The mRNA Expression of Cytokines and Their Receptors in Cultured Iris Pigment Epithelial Cells: A Comparison with Retinal Pigment Epithelial Cells", Experimental Eye Research, 67:237-250.
Stylianou et al. (2006) "Novel Cryoprotectant Significantly Improves the Post-thaw Recovery and Quality of HSC from CB", Cytotherapy, 8(1):57-61.
Saari et al. (Mar. 2001) "Visual Cycle Impairment in Cellular Retinaldehyde Binding Protein (CRALBP) Knockout Mice Results in Delayed Dark Adaptation", Neuron, 29(3):739-748.
Watt, Brenda (2011) "Dissecting the PMEL Amyloid: An Example of Functional vs. Pathological Amyloid", University of Pennsylvania ProQuest Dissertations, 1-12 (24 pages).
Rowley et al., "Lens deposits associated with RIMSO-50 (dimethylsulphoxide)," Eye. 15:332-333 (2001).

* cited by examiner

RETINAL PIGMENT EPITHELIUM CELL COMPOSITIONS

CROSS-REFERENCE TO RELATED APPLICATION

This application claims the benefit of U.S. Provisional Patent Application No. 62/612,210 filed Dec. 29, 2017, the contents of which is hereby incorporated by reference in its entirety.

BACKGROUND

The retinal pigment epithelium (RPE) is a monolayer of neuroepithelium-derived pigmented cells that lays on a Bruch's membrane between the photoreceptor outer segments (POS) and the choroidal vasculature. The RPE monolayer is critical to the function and health of the photoreceptors. Dysfunction, injury, and loss of retinal pigment epithelium (RPE) cells are prominent features of certain eye diseases and disorders, such as age-related macular degeneration (AMD), hereditary macular degenerations including Best disease (the early onset form of vitelliform macular dystrophy), and subtypes of retinitis pigmentosa (RP). The transplantation of RPE (and photoreceptors) into the retina of those affected with such diseases can be used as cell replacement therapy in retinal diseases where RPE have degenerated.

Human fetal and adult RPE have been used as a donor source for allogeneic transplantation. However, practical problems in obtaining sufficient tissue supply and the ethical concerns regarding the use of tissues from aborted fetuses limit widespread use of these donor sources. Given the limitations in the supply of adult and fetal RPE grafts, the potential of alternative donor sources has been studied.

Human pluripotent stem cells provide significant advantages as a source of RPE cells for transplantation. Their pluripotent developmental potential enables their differentiation into authentic functional RPE cells, and given their potential for infinite self-renewal, they can serve as an unlimited donor source of RPE cells. Indeed, it has been demonstrated that human embryonic stem cells (hESCs) and human induced pluripotent stem cells (iPSCs) may differentiate into RPE cells in vitro, attenuate retinal degeneration and preserve visual function after subretinal implantation. Therefore, hESCs can be an unlimited source for the production of RPE cells for cell therapy.

However, most cell based treatments are usually preserved frozen in a cryo-solution that is not compatible with direct administration into the body, creating a practical problem for clinical use. Cells should be transplanted within hours after they are thawed, or they may begin to lose viability and quality. In addition, cells must be prepared prior to administration in certified facilities, which may not be in close proximity to clinical sites, hospitals or other treatment facilities. Finally, each subject's treatment dose must be released by a qualified technician since preparation of the final formulation is considered to be part of the cell therapy production process.

The present disclosure addresses these and other shortcomings in the field of regenerative medicine and RPE cell therapy.

BRIEF SUMMARY

In one aspect, ready to administer (RTA) retinal pigment epithelium (RPE) cell therapy compositions for the treatment of retinal degenerative diseases and injuries are presented. A method of formulating human RPE cells for administration to a subject directly after thawing and of formulating RPE cell therapy compositions for cryopreservation and administration of the cryopreserved composition to a subject subsequent to thawing are also presented. In another aspect, the RTA composition may be formulated as a thaw and inject (TAI) composition, whereby the composition is administered by injection subsequent to thawing.

In other aspects, methods for one or more of, slowing the progression of retinal degenerative disease, slowing the progression of age related macular degeneration (AMD) and/or Geographic Atrophy (GA), preventing retinal degenerative disease, preventing AMD, preventing GA, restoring retinal pigment epithelium (RPE), increasing RPE, replacing RPE or treating RPE defects, in a subject by administering to the subject a composition comprising RPE cells and a ready to administer biocompatible cryopreservation media are presented.

The cryopreservation media described herein may comprise about 2% DMSO, 5% DMSO, between about 1% and about 15% DMSO, or between about 0.5% and about 7% DMSO, or between about 1.5% and about 6.5% DMSO, or between about 1.5% and about 3% DMSO, or between about 4% and about 6% DMSO.

In some aspects, the cryopreservation media comprises: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO).

In other aspects, the retinal degenerative disease comprises one or more of: RPE dysfunction, photoreceptor dysfunction, accumulation of lipofuscin, formation of drusen, or inflammation.

The retinal degenerative disease may be selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage caused by any one of photic, laser, infection, radiation, neovascular or traumatic injury. In addition, the AMD may comprise geographic atrophy (GA).

In another aspect, the RPE defects result from one or more of: advanced age, cigarette smoking, unhealthy body weight, low intake of antioxidants, or cardiovascular disorders. In yet another aspect, the RPE defects result from a congenital abnormality.

In some aspects, a method of restoring vision in a subject in need thereof is described, including: administering to the subject a composition comprising: adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), water, and retinal pigment epithelium (RPE) cells.

In other aspects, a method of restoring vision in a subject in need thereof is described, including: administering to the subject a composition comprising: a cell preservation media comprising: a purine nucleoside (e.g., adenosine), a branched glucan (e.g., dextran-40), a zwitterionic organic chemical buffering agent (e.g., HEPES (N-(2-Hydroxyethyl)

piperazine-N'-(2-ethanesulfonic acid))), and a cell tolerable polar aprotic solvent (e.g., dimethyl sulfoxide (DMSO); and RPE cells.

In other aspects, a method of formulating human retinal pigment epithelium (RPE) cells for administration to a subject directly after thawing is described, including: (a) suspending RPE cells to form a cell suspension in a cell preservation media comprising: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); (b) storing the cell suspension at a cryopreservation temperature; and (c) thawing the cryopreserved suspension, wherein at least about 60% to about 92% of the cells are viable after thawing.

In some aspects, a method of formulating human retinal pigment epithelium (RPE) cells for administration to a subject directly after thawing is described, including: (a) suspending RPE cells to form a cell suspension in a cell preservation media comprising: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); (b) storing the cell suspension at a cryopreservation temperature; and (c) thawing the cryopreserved suspension, wherein there is at least about a 50% to about a 120% yield of cells after thawing.

In some aspects, there was at least about 65% to about 70% yield of cells after thawing; at least about 64% to about 97% yield of cells after thawing; at least about 59% to about 82% yield of cells after thawing.

In other aspects, a method of formulating human retinal pigment epithelium (RPE) cells for administration to a subject directly after thawing is described, including: (a) suspending RPE cells to form a cell suspension in a cell preservation media comprising: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); (b) storing the cell suspension at a cryopreservation temperature; and (c) thawing the cryopreserved suspension, wherein there was at least about a 30% to about a 112% vitality of cells about twenty-four (24) hours after thawing.

In some aspects, there was at least about an 89% to about a 110% vitality of cells about twenty-four (24) hours after thawing; there was at least about a 76% to about a 112% vitality of cells about twenty-four (24) hours after thawing.

In other aspects, a method of formulating human retinal pigment epithelium (RPE) cells for administration to a subject directly after thawing is described, the method including: (a) suspending RPE cells to form a cell suspension in a cell preservation media comprising: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); (b) storing the cell suspension at a cryopreservation temperature; and (c) thawing the cryopreserved suspension, wherein there was at least about a 3 to about a 7-fold expansion of cells about 8-18 days after thawing and culturing.

In other aspects, there was at least about a 4.2 to about a 5.4-fold expansion of cells about fourteen (14) days after thawing and culturing. In yet other aspects, there was at least about a 4.2 to about a 4.9-fold expansion of cells about fourteen (14) days after thawing and culturing; there was at least about a 4.5 to about a 5.4 fold expansion of cells about fourteen (14) days after thawing and culturing.

In other aspects, a method of formulating human retinal pigment epithelium (RPE) cells for administration to a subject directly after thawing is described, the method including: (a) suspending RPE cells to form a cell suspension in a cell preservation media comprising: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); (b) storing the cell suspension at a cryopreservation temperature; and (c) thawing the cryopreserved cell suspension, wherein the cells demonstrated one or more of the following after thawing: a barrier function TEER of about 100Ω to about 1300Ω; a PEDF Upper to Lower Ratio of about 3.5 to about 9.4; a VEGF Lower to Upper Ratio of about 1.2 to about 5; or a purity of about 95% to about 100%.

In some aspects, the cells had a barrier function of about 107 to about 402Ω; or of about 241 to about 715Ω. In other aspects, the cells had a PEDF upper to lower ratio of about 5.1 to about 9.4; or of about 3.5 to about 9.4. In other aspects, the cells had a VEGF Lower to Upper Ratio of about 1.2 to about 1.7; or of about 1.2 to about 1.9.

In some aspects, one or more of the purine nucleoside, branched glucan, buffering agent, and the polar aprotic solvent are generally recognized as safe by the US FDA.

In other aspects, the cell preservation further comprising one or more of: a sugar acid (e.g., lactobionic acid), one or more of a base (e.g., sodium hydroxide, potassium hydroxide), an antioxidant (e.g., L-glutathione), one or more halide salt (e.g., potassium chloride, sodium chloride, magnesium chloride), a basic salt (e.g., potassium bicarbonate), phosphate salt (e.g., potassium phosphate, sodium phosphate, potassium phosphate), one or more sugars (e.g., dextrose, sucrose), sugar alcohol, (e.g., mannitol), and water.

In still other aspects, the sugar acid comprises lactobionic acid, glyceric acid, xylonic acid, gluconic acid, ascorbic acid, neuraminic acid, ketodeoxyoctulosonic acid, glucuronic acid, galacturonic acid, galacturonic acid, iduronic acid, tartaric acid, mucic acid, or saccharic acid.

In some aspects, the one or more of a base comprises sodium hydroxide, or potassium hydroxide. In some aspects, the antioxidant comprises L-glutathione, ascorbic acid, lipoic acid, uric acid, a carotene, alpha-tocopherol, or ubiquinol. In some aspects, the one or more halide salt comprises potassium chloride, sodium chloride, or magnesium chloride. In some aspects, the basic salt comprises potassium bicarbonate, sodium bicarbonate, or sodium acetate. In some aspects, the phosphate salt comprises potassium phosphate, sodium phosphate, or potassium phosphate. In some aspects, the one or more sugars comprises dextrose, sucrose. In some aspects, the sugar alcohol comprises mannitol, sorbitol, erythritol or xylitol. In some aspects, the one or more of the sugar acid, base, halide salt, basic salt, antioxidant, phosphate salt, sugars, sugar alcohols are generally recognized as safe by the US FDA.

In other aspects, the RPE composition is administered subretinally. In other aspects, the RPE composition is administered using a delivery device. In other aspects, the delivery device comprises a needle, a capillary and a tip. In other aspects, the delivery device comprises a needle with an outer diameter of about 0.63 mm and an inner diameter of about 0.53 mm, a capillary with an outer diameter of about 0.5 mm and an inner diameter of about 0.25 mm, and a tip with an outer diameter of about 0.12 mm and an inner diameter of about 0.07 mm.

In certain aspects, the post-delivery percent viability is between about 85% and about 99%, the post-delivery percent recovery is between about 65% and about 99%, the post-delivery barrier function TEER is between about 100 and about 600Ω, the PEDF apical/basal ratio is between about 2 and about 7, and the post-delivery VEGF basal/apical ratio is between about 1.5 and about 3.

In some aspects, the composition is administered in the subretinal space. In some aspects, the composition is injected. In some aspects, the composition is administered as a single dose treatment.

In other aspects, the composition does not cause inflammation after it is administered. In yet other aspects, inflammation is characterized by the presence of cells associated with inflammation. In other aspects, the cell composition is administered without vitrectomy and without the need to pierce the retina. In some aspects, the cell composition is administered by a suprachoroidal injection.

In some aspects, the cells secrete one or more of the neurotrophic factors: fibroblast growth factors (bFGF and aFGF), ciliary neurotrophic factor (CNTF), pigment epithelium-derived factor (PEDF), brain-derived neurotrophic factor (BDNF), and vascular endothelial growth factor (VEGF). In some aspects, the cells secrete one or more anti-inflammatory cytokines.

In other aspects, a method of formulating human retinal pigment epithelium (RPE) cells for administration to a subject directly after thawing is described, including: (a) suspending the RPE cells in a media composition comprising: adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water; (b) storing the cell suspension at a temperature adequate for cryopreservation; and (c) thawing the cryopreserved suspension, wherein at least about 60% to about 95% of the cells are viable after thawing.

In other aspects, at least about 40% to about 100% of the cells are viable after thawing; at least about 45% to about 95% of the cells are viable after thawing; at least about 62% to about 70% of the cells are viable after thawing.

In some aspects, a method of formulating human retinal pigment epithelium (RPE) cells for administration to a subject directly after thawing is described, the method includes: (a) differentiating stem cells into a population of cells comprising RPE cells; (b) enzymatically harvesting the RPE cells; (c) neutralizing the enzyme with a neutralizing agent, wherein the neutralizing agent does not comprise human serum; (d) suspending the RPE cells in a media composition comprising: adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water; (e) storing the cell suspension at a temperature adequate for cryopreservation; and (f) thawing the cryopreserved suspension, wherein at least about 70% of the cells are viable after thawing.

In some aspects, the RPE cells are stored in the neutralizing agent for between about 1 to about 8 hours and the viability does not decrease by greater than about 10%. In some aspects, the RPE cells are suspended in the media composition for about 3 hours prior to cryopreservation, and the post thaw percent viability does not decrease by greater than about 10%, the post thaw percent yield does not decrease by greater than 20%, and the post thaw vitality does not decrease by greater than 10% compared to RPE cells suspended in the media for less than 1 hour.

In some aspects, the RPE cells are suspended in the media composition for about 3 hours prior to cryopreservation, and the post thaw barrier function does not decrease, the post thaw PEDF upper to lower ratio does not decrease by greater than 10%, and the post thaw VEGF lower to upper ratio does not decrease compared to RPE cells suspended in the media for less than 1 hour.

In some aspects, the RPE cells are suspended in the media composition for between about 2 to 3 hours prior to cryopreservation, and the post thaw percent viability is between about 50 to about 75, the post thaw percent yield is between about 50 to about 95, the post thaw vitality is between about 80 to about 120, the post thaw barrier function is about 100 to about 750Ω, the post thaw PEDF upper to lower ratio is between about 3 to about 7, and the post thaw VEGF lower to upper ratio is between about 1 to 3.

In some aspects, the methods described further comprise: sequentially filtering the RPE cells following step (c), wherein the percent viability is at least 98%. In some aspects, the method further comprising: sequentially filtering the RPE cells following step (c) and incubating the RPE cells in the media composition for between about 2-4 hours, wherein the percent recovery is between about 80% and about 95%.

In some aspects, the methods described further comprise: sequentially filtering the RPE cells following step (c), incubating the RPE cells in the neutralizing solution for between about 2 to about 4 hours, and incubating the RPE cells in the media composition for between about 2-4 hours, wherein the percent viability is between about 80% and about 99% and wherein the percent recovery is between about 70% and about 95%.

In other aspects, the methods described further comprise: sequentially filtering the RPE cells following step (c), incubating the RPE cells in the neutralizing solution for between about 2 to about 4 hours, and incubating the RPE cells in the media composition for between about 2-4 hours, wherein the post thaw percent viability is between about 80% and about 99%, the post thaw percent recovery is between about 70% and about 95% and the PEDF secretion is between about 2,000 ng/ml/day and about 3,000 ng/ml/day.

In other aspects, the methods described further comprise: incubating the RPE cells in the media composition for between about 2-6 hours at room temperature, wherein the percent viability is between about 80% and about 99% and wherein the percent recovery is between about 80% and about 120%.

In other aspects, a composition is described comprising: (a) adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water; and (b) RPE cells, wherein the composition can be stored at cryothermic temperatures and wherein the composition is ready to administer to a subject directly after thawing.

In other aspects, a composition is described including: (a) a cell preservation media comprising: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); and (b) RPE cells.

In certain compositions, the one or more of the purine nucleoside, branched glucan, buffering agent, and the polar aprotic solvent are generally recognized as safe by the US FDA.

In other aspects, the therapeutic cell compositions described herein further comprise: one or more of: a sugar acid (e.g., lactobionic acid), one or more of a base (e.g., sodium hydroxide, potassium hydroxide), an antioxidant (e.g., L-glutathione), one or more halide salt (e.g., potassium chloride, sodium chloride, magnesium chloride), a basic salt (e.g., potassium bicarbonate), phosphate salt (e.g., potassium phosphate, sodium phosphate, potassium phosphate), one or more sugars (e.g., dextrose, sucrose), sugar alcohol, (e.g., mannitol), and water.

In other aspects of the compositions described, the sugar acid comprises lactobionic acid, glyceric acid, xylonic acid, gluconic acid, ascorbic acid, neuraminic acid, ketodeoxyoctulosonic acid, glucuronic acid, galacturonic acid, galacturonic acid, iduronic acid, tartaric acid, mucic acid, or saccharic acid. In other aspects of the compositions described, the one or more of a base comprises sodium hydroxide, or potassium hydroxide. In other aspects of the compositions described, the antioxidant comprises L-glutathione, ascorbic acid, lipoic acid, uric acid, a carotene, alpha-tocopherol, or ubiquinol. In other aspects of the compositions described, the one or more halide salt comprises potassium chloride, sodium chloride, or magnesium chloride. In other aspects of the compositions described, the basic salt comprises potassium bicarbonate, sodium bicarbonate, or sodium acetate. In other aspects of the compositions described, the phosphate salt comprises potassium phosphate, sodium phosphate, or potassium phosphate. In other aspects of the compositions described, the one or more sugars comprises dextrose, sucrose. In other aspects of the compositions described, the sugar alcohol comprises mannitol, sorbitol, erythritol or xylitol. In other aspects of the compositions described, the one or more of the sugar acid, base, halide salt, basic salt, antioxidant, phosphate salt, sugars, sugar alcohols are generally recognized as safe by the US FDA.

In other aspects of the compositions described, the RPE cell concentration is between about 100,000 and about 10,000,000 cells/ml. In other aspects of the compositions described, the number of cells in said composition is between about 100,000 to about 500,000.

In other aspects of the compositions described, the cell preservation media further comprises one or more of: a sugar acid (e.g., lactobionic acid), one or more of a base (e.g., sodium hydroxide, potassium hydroxide), an antioxidant (e.g., L-glutathione), one or more halide salt (e.g., potassium chloride, sodium chloride, magnesium chloride), a basic salt (e.g., potassium bicarbonate), phosphate salt (e.g., potassium phosphate, sodium phosphate, potassium phosphate), one or more sugars (e.g., dextrose, sucrose), sugar alcohol, (e.g., mannitol), and water.

In other aspects of the compositions described, the compositions further comprise one or more of ROCK inhibitor or NA.

In further aspects, the cryopreservation media comprises: adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water.

In some embodiments, the cryopreservation media includes about 2% DMSO. In other embodiments, the cryopreservation media includes about 5% DMSO. In yet other embodiments, the cryopreservation media includes between about 1% and about 15% DMSO.

In further embodiments, the cryopreservation media includes: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO). In still further embodiments, one or more of the purine nucleoside, branched glucan, buffering agent, and the polar aprotic solvent are generally recognized as safe by the US FDA.

In some embodiments, the cryopreservation media further includes one or more of: a sugar acid (e.g., lactobionic acid), one or more of a base (e.g., sodium hydroxide, potassium hydroxide), an antioxidant (e.g., L-glutathione), one or more halide salt (e.g., potassium chloride, sodium chloride, magnesium chloride), a basic salt (e.g., potassium bicarbonate), phosphate salt (e.g., potassium phosphate, sodium phosphate, potassium phosphate), one or more sugars (e.g., dextrose, sucrose), sugar alcohol, (e.g., mannitol), and water.

In other embodiments, one or more of the sugar acid, base, halide salt, basic salt, antioxidant, phosphate salt, sugars, sugar alcohols are generally recognized as safe by the US FDA.

In certain embodiments, the retinal degenerative disease may be one or more of: RPE dysfunction, photoreceptor dysfunction, accumulation of lipofuscin, formation of drusen, or inflammation.

In other embodiments, the retinal degenerative disease is selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage caused by any one of photic, laser, infection, radiation, neovascular or traumatic injury. In yet other embodiments, the AMD is geographic atrophy (GA).

In certain embodiments, the RPE defects may result from one or more of: advanced age, cigarette smoking, unhealthy body weight, low intake of antioxidants, or cardiovascular disorders. In other embodiments, the RPE defects may result from a congenital abnormality.

In other embodiments, a method of formulating human retinal pigment epithelium (RPE) cells for administration to a subject directly after thawing includes: suspending the RPE cells in a composition comprising: adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water, storing the cell suspension at a temperature adequate for cryopreservation and thawing the cryopreserved suspension, wherein at least about 70% of the cells are viable after thawing.

In other embodiments, a method of formulating human retinal pigment epithelium (RPE) cells for administration to a subject directly after thawing includes: suspending the RPE cells to form a cell suspension in a media which includes: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); storing the cell suspension at a cryopreservation temperature; and thawing the cryopreserved suspension, wherein at least about 60% to about 75% of the cells are viable after thawing.

In other embodiments a method of formulating human retinal pigment epithelium (RPE) cells for administration to a subject directly after thawing includes the addition of one or more of: a sugar acid (e.g., lactobionic acid), one or more of a base (e.g., sodium hydroxide, potassium hydroxide), an antioxidant (e.g., L-glutathione), one or more halide salt (e.g., potassium chloride, sodium chloride, magnesium chloride), a basic salt (e.g., potassium bicarbonate), phosphate salt (e.g., potassium phosphate, sodium phosphate, potassium phosphate), one or more sugars (e.g., dextrose, sucrose), sugar alcohol, (e.g., mannitol), and water to the formulation.

In some embodiments, at least about 40% to about 100% of the cells are viable after thawing; at least about 45% to about 95% of the cells are viable after thawing; at least about 62% to about 70% of the cells are viable after thawing.

In some embodiments, a method of formulating human retinal pigment epithelium (RPE) cells for administration to a subject directly after thawing includes: suspending the RPE cells to form a cell suspension in a media, which includes: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); storing the cell suspension at a cryopreservation temperature; and thawing the cryopreserved suspension, wherein there was at least about a 59% to about a 92% yield of cells after thawing.

In some embodiments, there was at least about 65% to about 70% yield of cells after thawing; at least about 64% to about 92% yield of cells after thawing; at least about 59% to about 82% yield of cells after thawing.

In some embodiments, a method of formulating human retinal pigment epithelium (RPE) cells for administration to a subject directly after thawing includes: suspending the RPE cells to form a cell suspension in a media, which includes: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); storing the cell suspension at a cryopreservation temperature; and thawing the cryopreserved suspension, wherein there was at least about a 76% to about a 112% vitality of cells about twenty-four (24) hours after thawing.

In some embodiments, there was at least about an 89% to about a 110% vitality of cells about twenty-four (24) hours after thawing; there was at least about a 76% to about a 112% vitality of cells about twenty-four (24) hours after thawing.

In other embodiments, a method of formulating human retinal pigment epithelium (RPE) cells for administration to a subject directly after thawing includes: suspending the RPE cells to form a cell suspension in a media, which includes: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); storing the cell suspension at a cryopreservation temperature; and thawing the cryopreserved suspension, wherein there was at least about a 4.2 to about a 5.4 fold expansion of cells about fourteen (14) days after thawing and culturing.

In some embodiments, there was at least about a 4.2 to about a 4.9 fold expansion of cells about fourteen (14) days after thawing and culturing; there was at least about a 4.5 to about a 5.4 fold expansion of cells about fourteen (14) days after thawing and culturing. In some embodiments, there was at least about a 3 to about a 7 fold expansion of cells about 8-18 days after thawing and culturing. In some embodiments, there was at least about a 3 to about a 5 fold expansion of cells about 8 days after thawing and culturing.

In some embodiments, a method of formulating human retinal pigment epithelium (RPE) cells for administration to a subject directly after thawing includes: suspending the RPE cells to form a cell suspension in a media, which includes: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); storing the cell suspension at a cryopreservation temperature; and thawing the cryopreserved suspension, wherein the cells demonstrated one or more of the following after thawing: had a barrier function of about 100 to about 720; had a PEDF Upper to Lower Ratio of about 3.5 to about 9.4; had a VEGF Lower to Upper Ratio of about 1.2 to about 2.7; had a purity of about 95 to about 100%; had a potency of about 150 to about 900.

In some embodiments, the cells had a barrier function of about 107 to about 402Ω; or of about 241 to about 715Ω.

In some embodiments, the cells had a PEDF Upper to Lower Ratio of about 5.1 to about 9.4; or of about 3.5 to about 9.4.

In some embodiments, the cells had a VEGF Lower to Upper Ratio of about 1.2 to about 1.7; or of about 1.2 to about 1.9.

In some embodiments, a method of restoring vision in a subject in need thereof, includes: administering to the subject a composition including: adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), water, and retinal pigment epithelium cells.

In some embodiments, a method of restoring vision in a subject in need thereof, includes: administering to the subject a composition including: a cell preservation media comprising: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); and RPE cells. In some embodiments, the cell preservation media further comprises one or more of: a sugar acid (e.g., lactobionic acid), one or more of a base (e.g., sodium hydroxide, potassium hydroxide), an antioxidant (e.g., L-glutathione), one or more halide salt (e.g., potassium chloride, sodium chloride, magnesium chloride), a basic salt (e.g., potassium bicarbonate), phosphate salt (e.g., potassium phosphate, sodium phosphate, potassium phosphate), one or more sugars (e.g., dextrose, sucrose), sugar alcohol, (e.g., mannitol), and water.

In some embodiments, the cell composition is administered in the subretinal space. In other embodiments, the cell composition is injected. In some embodiments, the cell composition may be administered into the subretinal space transvitreally.

In some embodiments, the cell composition is administered as a single dose treatment. In some embodiments, the single dose treatment comprises a single administration comprising several injections. In some embodiments, the injections comprise the administration of several subretinal blebs.

In some embodiments, the cell composition is administered to the subretinal space without vitrectomy and without the need to pierce the retina. In some embodiments, the cell composition is administered by suprachoroidal injection.

In some embodiments RPE cells secrete a variety of neurotrophic factors, such as fibroblast growth factors (bFGF and aFGF), ciliary neurotrophic factor (CNTF), pigment epithelium-derived factor (PEDF), brain-derived neurotrophic factor (BDNF), vascular endothelial growth factor (VEGF) and others, that help to maintain the structural integrity of choriocapillaris endothelium and photoreceptors. RPE cells also secrete anti-inflammatory cytokines such as transforming growth factor (TGF)-β, important in establishing the immune privileged properties of the eye. The RPE cells used in the RTA therapeutic cell compositions described herein are capable of secreting neurotrophic factors.

In some embodiments, the cell composition does not cause inflammation after it is administered. In some embodiments, a mild inflammation may be characterized by the presence of cells associated with inflammation.

In some embodiments, a composition includes: (a) adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water; and (b) RPE cells, wherein the composition can be stored at cryothermic temperatures and wherein the composition is ready to administer to a subject directly after thawing.

In other embodiments, a therapeutic cell composition may comprise: a cell preservation media including: a purine nucleoside (e.g., adenosine), a branched glucan (e.g., dextran-40), a zwitterionic organic chemical buffering agent (e.g., HEPES (N-(2-Hydroxyethyl) piperazine-N'-(2-ethanesulfonic acid))), and a cell tolerable polar aprotic solvent (e.g., dimethyl sulfoxide (DMSO); and RPE cells.

In some embodiments, the cell preservation media further comprises one or more of: a sugar acid (e.g., lactobionic acid), one or more of a base (e.g., sodium hydroxide, potassium hydroxide), an antioxidant (e.g., L-glutathione), one or more halide salt (e.g., potassium chloride, sodium chloride, magnesium chloride), a basic salt (e.g., potassium bicarbonate), phosphate salt (e.g., potassium phosphate, sodium phosphate, potassium phosphate), one or more sugars (e.g., dextrose, sucrose), sugar alcohol, (e.g., mannitol), and water.

In yet other embodiments, the cell preservation media may comprise one or more of ROCK inhibitor and NA.

In some embodiments, an RPE cell composition comprises adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water; and RPE cells at a cell concentration of between about 2,000,000 and about 5,000,000 cells/ml. The composition can be stored at cryothermic temperatures, and the composition is ready to administer to a subject directly after thawing. In this RPE cell composition the number of cells may be between about 200,000 to about 500,000. In addition, the volume administered to the subject may be between about 50 μl and about 100 μl.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
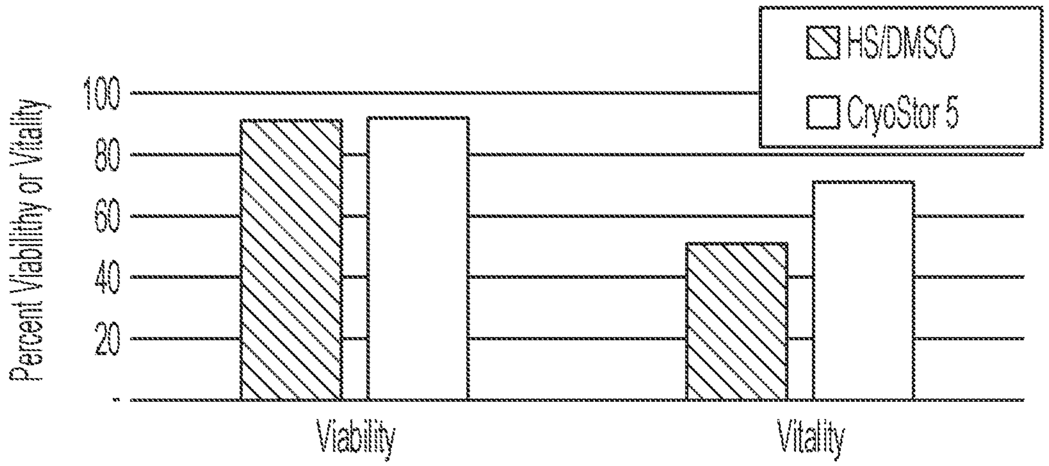
FIG. 1 is a graph showing the viability and vitality of retinal pigment epithelium (RPE) cells after thawing. Cells were cryopreserved in cryopreservation media with 5% DMSO (CS5) prior to thawing.

Compositions described herein may be used as a ready to administer (RTA) retinal pigment epithelium (RPE) cell composition suitable for therapeutic use which does not require preparation procedures such as washing or reconstitution prior to injection or implantation into a subject's eye. In some embodiments, the cell therapy composition is preserved in a non-toxic cryo-solution, shipped to the clinical site, thawed and readily administered to the subject's eye by healthcare personnel. By eliminating preparation procedures prior to administration, especially those preparation procedures that must be carried out under GLP/GMP conditions, widespread access to RPE cell therapy can be made available, while preserving product safety and quality.

"Retinal pigment epithelium cells", "RPE cells", "RPEs", which may be used interchangeably as the context allows, refers to cells of a cell type that is for example, functionally, epi-genetically, or by expression profile similar to that of native RPE cells which form the pigment epithelium cell layer of the retina (e.g., upon transplantation, administration or delivery within an eye, they exhibit functional activities similar to those of native RPE cells).

According to some embodiments, the RPE cell expresses at least one, two, three, four or five markers of mature RPE cells. According to some embodiments, the RPE cell expresses between at least two to at least ten or at least two to at least thirty markers of mature RPE cells. Such markers include, but are not limited to CRALBP, RPE65, PEDF, PMEL17, bestrophin 1 and tyrosinase. Optionally, the RPE cell may also express a marker of a RPE progenitor (e.g., MITF). In other embodiments, the RPE cells express PAX-6. In other embodiments, the RPE cells express at least one marker of a retinal progenitor cell including, but not limited to Rx, OTX2 or SIX3. Optionally, the RPE cells may express either SIX6 and/or LHX2.

As used herein the phrase "markers of mature RPE cells" refers to antigens (e.g., proteins) that are elevated (e.g., at least 2-fold, at least 5-fold, at least 10-fold) in mature RPE cells with respect to non RPE cells or immature RPE cells.

As used herein the phrase "markers of RPE progenitor cells" refers to antigens (e.g., proteins) that are elevated (e.g., at least 2-fold, at least 5-fold, at least 10-fold) in RPE progenitor cells when compared with non RPE cells.

According to other embodiments, the RPE cells have a morphology similar to that of native RPE cells which form the pigment epithelium cell layer of the retina. For example, the cells may be pigmented and have a characteristic polygonal shape.

According to still other embodiments, the RPE cells are capable of treating diseases such as macular degeneration.

According to additional embodiments, the RPE cells fulfill at least 1, 2, 3, 4 or all of the requirements listed herein above.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPSCs), adult stem cells, mesenchymal stem cells and hematopoietic stem cells.

According to some embodiments, the RPE cells are generated from pluripotent stem cells (e.g., ESCs or iPSCs).

Induced pluripotent stem cells (iPSCs) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis. In addition, iPSCs may be generated using non-integrating methods e.g., by using small molecules or RNA.

The phrase "embryonic stem cells" refers to embryonic cells that are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a preimplantation blastocyst), extended blastocyst cells (EBCs) which are obtained from a post-implantation/pre-gastrulation stage blastocyst (see WO 2006/040763) and embryonic germ (EG) cells which are obtained from the genital tissue of a fetus any time during gestation, preferably before 10 weeks of gestation. The embryonic stem cells of some embodiments of the present disclosure can be obtained using well-known cell-culture methods. For example, human embryonic stem cells can be isolated from human blastocysts.

Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by a procedure in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells, see Reubinoff et al. Nat Biotechnol 2000, May: 18(5): 559; Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the present disclosure Human ES cells can be purchased from the NIH human embryonic stem cells registry, www.grants.nih.govstem_cells/ or from other hESC registries. Non-limiting examples of commercially available embryonic stem cell lines are HAD-C I02, ESI, BGO I, BG02, BG03, BG04, CY12, CY30, CY92, CYIO, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WAO I, UCSF4, NYUES I, NYUES2, NYUES3, NYUES4, NYUES5, NYUES6, NYUES7, UCLA 1, UCLA 2, UCLA 3, WA077 (H7), WA09 (H9), WA 13 (HI3), WA14 (HI4), HUES 62, HUES 63, HUES 64, CT 1, CT2, CT3, CT4, MA135, Eneavour-2, WIBR I, WIBR2, WIBR3, WIBR4, WIBR5, WIBR6, HUES 45, Shef 3, Shef 6, BJNhemI9, BJNhem20, SAGO 1, SAOOI.

According to some embodiments, the embryonic stem cell line is HAD-C102 or ESI.

In addition, ES cells can be obtained from other species, including mouse (Mills and Bradley, 2001), golden hamster [Doetschman et al., 1988, Dev Biol. 127: 224-7], rat [Iannaccone et al., 1994, Dev Biol. 163: 288-92], rabbit [Giles et al. 1993, Mol Reprod Dev. 36: 130-8; Graves & Moreadith, 1993, Mol Reprod Dev. 1993, 30 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine days (and preferably not longer than fourteen days) post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

EG (embryonic germ) cells can be prepared from the primordial germ cells obtained from fetuses of about 8-11 weeks of gestation (in the case of a human fetus) using laboratory techniques known to anyone skilled in the arts. The genital ridges are dissociated and cut into small portions which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparing human EG cells, see Shamblott et al., [Proc. Natl. Acad. Sci. USA 95: 13726, 1998] and U.S. Pat. No. 6,090,622 incorporated herein by reference in their entirety.

Yet another method for preparing ES cells is by parthenogenesis. The embryo is also not destroyed in the process.

ES culturing methods may include the use of feeder cell layers which secrete factors needed for stem cell proliferation, while at the same time, inhibiting their differentiation. The culturing is typically carried out on a solid surface, for example a surface coated with gelatin or vimentin. Exemplary feeder layers include human embryonic fibroblasts, adult fallopian epithelial cells, primary mouse embryonic fibroblasts (PMEF), mouse embryonic fibroblasts (MEF), murine fetal fibroblasts (MFF), human embryonic fibroblast (HEF), human fibroblasts obtained from the differentiation of human embryonic stem cells, human fetal muscle cells (HFM), human fetal skin cells (HFS), human adult skin cells, human foreskin fibroblasts (HFF), human umbilical cord fibroblasts, human cells obtained from the umbilical cord or placenta, and human marrow stromal cells (hMSCs). Growth factors may be added to the medium to maintain the ESCs in an undifferentiated state. Such growth factors include bFGF and/or TGF. In another embodiment, agents may be added to the medium to maintain the hESCs in a naive undifferentiated state; see for example Kalkan et al., 2014, Phil. Trans. R. Soc. B, 369: 20130540.

Human umbilical cord fibroblasts may be expanded in Dulbecco's Modified Eagle's Medium (e.g. DMEM, SH30081.01, Hyclone) supplemented with human serum (e.g. 20%) and glutamine. Preferably the human cord cells are irradiated. This may be effected using methods known in the art (e.g. Gamma cell, 220 Exel, MDS Nordion 3,500-7500 rads). Once sufficient cells are obtained, they may be frozen (e.g. cryopreserved). For expansion of ESCs, the human cord fibroblasts may be seeded on a solid surface (e.g. T75 or T I75 flasks) optionally coated with an adherent substrate such as gelatin (e.g. recombinant human gelatin (RhG 100-001, Fibrogen) or human Vitronectin or Laminin 521 (Bio lamina) at a concentration of about 25,000-100,000 cells/$cm^2$ in DMEM (e.g. SH30081.01, Hyclone) supplemented with about 20% human serum (and glutamine). hESCs can be plated on top of the feeder cells 1-4 days later in a supportive medium (e.g. NUTRISTEM® or NUT(+) with human serum albumin). Additional factors may be added to the medium to prevent differentiation of the ESCs such as bFGF and TGFβ. Once a sufficient amount of hESCs are obtained, the cells may be mechanically disrupted (e.g. by using a sterile tip or a disposable sterile stem cell tool; 14602 Swemed). For example, the cells may be expanded mechanically during weekly passaging. Alternatively, the cells may be removed by enzymatic treatment (e.g. collagenase A, or TrypLE Select). This process may be repeated several times to reach the necessary concentration of hESC. According to some embodiments, following the first round of expansion, the hESCs are removed using TrypLE Select and following the second round of expansion, the hESCs are removed using collagenase A.

The ESCs may be expanded on feeders prior to the differentiation step. Exemplary feeder layer based cultures are described herein above. The expansion is typically carried out for at least two days, three days, four days, five days, six days, seven days, eight days, nine days, or ten days. The expansion can be carried out for at least 1 passage, at least 2 passages, at least 3 passages, at least 4 passages, at least 5 passages, at least 6 passages, at least 7 passages, at least 8 passages, at least 9 passages or at least 10 passages. In some embodiments, the expansion is carried out for at least 2 passages to at least 20 passages. In other embodiments, the expansion is performed for at least 2 to at least 40 passages. Following expansion, the pluripotent stem cells (e.g. ESCs) may be subjected to directed differentiation using a differentiating agent.

Feeder cell free systems can also be used in ES cell culturing. Such systems utilize matrices supplemented with serum replacement, cytokines and growth factors (including IL6 and soluble IL6 receptor chimera) as a replacement for the feeder cell layer. Stem cells can be grown on a solid surface such as an extracellular matrix (e.g., MATRIGELR™, laminin or vitronectin) in the presence of a culture medium—for example the Lonza L7 system, mTeSR, StemPro, XFKSR, E8, NUTRISTEM®). Unlike feeder-based cultures which require the simultaneous growth of feeder cells and stem cells and which may result in mixed cell populations, stem cells grown on feeder-free systems are easily separated from the surface. The culture medium used to for growing the stem cells contains factors that effectively inhibit differentiation and promote their growth such as MEF-conditioned medium and bFGF.

In some embodiments, following expansion, the pluripotent ESCs are subjected to directed differentiation on an adherent surface (without intermediate generation of spheroid or embryoid bodies). See, for example, international patent application publication No. WO 2017/072763, incorporated by reference herein in its entirety.

Thus, according to an aspect of the present disclosure, at least 50%, 55%, 60%, 65%, 70%, 75%, 80%, 85%, 90%, 91%, 92%, 93%, 94%, 95%, 96%, 97%, 98%, 99% or 100% of the cells which are subjected to directed differentiation on the adherent surface are undifferentiated ESCs and express markers of pluripotency. For example, at least 50%, 55%, 60%, 65%, 70%, 75%, 80%, 85%, 90%, 91%, 92%, 93%, 94%, 95%, 96%, 97%, 98%, 99% or 100% of the cells are $Oct4^{+}$TRA-I-60+. The non-differentiated ESCs may express other markers of pluripotency, such as NANOG, Rex-1, alkaline phosphatase, Sox2, TDGF-beta, SSEA-3, SSEA-4, SSEA-5, OCT4, TRA-1-60 and/or TRA-1-81.

In one exemplary differentiation protocol, the non-differentiated embryonic stem cells are differentiated towards the RPE cell lineage on an adherent surface using a first differentiating agent and then further differentiated towards RPE cells using a member of the transforming growth factor-β (TGFβ) superfamily, (e.g. TGF I, TGF2, and TGF 3 subtypes, as well as homologous ligands including activin (e.g., activin A, activin B, and activin AB), nodal, anti-mullerian hormone (AMH), some bone morphogenetic proteins (BMP), e.g. BMP2, BMP3, BMP4, BMP5, BMP6, and BMP7, and growth and differentiation factors (GDF)). According to a specific embodiment, the member of the transforming growth factor-β (TGFβ) superfamily is activin A—e.g. between 20-200 ng/ml, e.g. 100-180 ng/ml.

According to some embodiments, the first differentiating agent is nicotinamide (NA) used at concentrations of between about 1-100 mM, 5-50 mM, 5-20 mM, and e.g. 10 mM. According to other embodiments, the first differentiating agent is 3-aminobenzmine.

NA, also known as "niacinamide", is the amide derivative form of Vitamin B3 (niacin) which is thought to preserve and improve beta cell function. NA has the chemical formula C6H6N20. NA is essential for growth and the conversion of foods to energy, and it has been used in arthritis treatment and diabetes treatment and prevention.

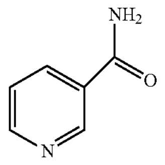

Nicotinamide (NA)

According to some embodiments, the nicotinamide is a nicotinamide derivative or a nicotinamide mimic. The term "derivative of nicotinamide (NA)" as used herein denotes a compound which is a chemically modified derivative of the natural NA. In one embodiment, the chemical modification may be a substitution of the pyridine ring of the basic NA structure (via the carbon or nitrogen member of the ring), via the nitrogen or the oxygen atoms of the amide moiety. When substituted, one or more hydrogen atoms may be replaced by a substituent and/or a substituent may be attached to a N atom to form a tetravalent positively charged nitrogen. Thus, the nicotinamide of the present invention includes a substituted or non-substituted nicotinamide. In another embodiment, the chemical modification may be a deletion or replacement of a single group, e.g. to form a thiobenzamide analog of NA, all of which being as appreciated by those versed in organic chemistry. The derivative in the context of the invention also includes the nucleoside derivative of NA (e.g. nicotinamide adenine). A variety of derivatives of NA are described, some also in connection with an inhibitory activity of the PDE4 enzyme (WO 03/068233; WO 02/060875; GB2327675A), or as VEGF-receptor tyrosine kinase inhibitors (WOO I/55114). For example, the process of preparing 4-aryl-nicotinamide derivatives (WO 05/014549). Other exemplary nicotinamide derivatives are disclosed in WOO I/55114 and EP2128244.

Nicotinamide mimics include modified forms of nicotinamide, and chemical analogs of nicotinamide which recapitulate the effects of nicotinamide in the differentiation and maturation of RPE cells from pluripotent cells. Exemplary nicotinamide mimics include benzoic acid, 3-aminobenzoic acid, and 6-aminonicotinamide. Another class of compounds that may act as nicotinamide mimics are inhibitors of poly(ADP-ribose) polymerase (PARR). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

Additional contemplated differentiation agents include for example noggin, antagonists of Wnt (Dkk1 or IWR1e), nodal antagonists (Lefty-A), retinoic acid, taurine, GSK3b inhibitor (CHIR99021) and notch inhibitor (DAFT).

According to certain embodiments, the differentiation is effected as follows: (a) culture of ESCs in a medium comprising a first differentiating agent (e.g. nicotinamide); and (b) culture of cells obtained from step a) in a medium comprising a member of the TGFβ superfamily (e.g. activin A) and the first differentiating agent (e.g. nicotinamide). Step (a) may be effected in the absence of the member of the TGFβ superfamily (e.g. activin A).

In some embodiments, the medium in step (a) is completely devoid of a member of the TGFβ superfamily. In other embodiments, the level of TGFβ superfamily member in the medium is less than 20 ng/ml, 10 ng/ml, 1 ng/ml or even less than 0.1 ng/ml.

The above described protocol may be continued by culturing the cells obtained in step (b) in a medium comprising the first differentiating agent (e.g. nicotinamide), but devoid of a member of the TGFβ superfamily (e.g. activin A). This step is referred to herein as step (b*).

The above described protocol is now described in further detail, with additional embodiments.

Step (a): The differentiation process is started once sufficient quantities of ESCs are obtained. They are typically removed from the cell culture (e.g. by using collagenase A, dispase, TrypLE select, EDTA) and plated onto a non-adherent substrate (e.g. cell culture plate such as Hydrocell or an agarose-coated culture dish, or petri bacteriological dishes) in the presence of nicotinamide (and the absence of activin A). Exemplary concentrations of nicotinamide are between 0.01-100 mM, 0.1-100 mM, 0.1-50 mM, 5-50 mM, 5-20 mM, and 10 mM. Once the cells are plated onto the non-adherent substrate (e.g. cell culture plate), the cell culture may be referred to as a cell suspension, preferably free-floating clusters in a suspension culture, i.e. aggregates of cells derived from human embryonic stem cells (hESCs). The cell clusters do not adhere to any substrate (e.g., culture plate, carrier). Sources of free floating stem cells were previously described in WO 06/070370, which is herein incorporated by reference in its entirety. This stage may be effected for a minimum of 1 day, more preferably two days, three days, 1 week or even 14 days. Preferably, the cells are not cultured for more than 3 weeks in suspension together with the nicotinamide e.g. between 0.01-100 mM, 0.1-100 mM, 0.1-50 mM, 5-50 mM, 5-20 mM, e.g., 10 mM (and in the absence of activin A). In one embodiment, the cells are cultured for 6-8 days in suspension together with the nicotinamide e.g., between 0.01-100 mM, 0.1-100 mM, 0.1-50 mM, 5-50 mM, 5-20 mM, e.g., 10 mM (and in the absence of activin A).

According to some embodiments, when the cells are cultured on the non-adherent substrate e.g., cell culture plates, the atmospheric oxygen conditions are 20%. However, manipulation of the atmospheric oxygen conditions is also contemplated such that the atmospheric oxygen percent is less than about 20%, 15%, 10%, 9%, 8%, 7%, 6% or even less than about 5% (e.g., between 1%-20%, 1%-10% or 0-5%). According to other embodiments, the cells are cultured on the non-adherent substrate initially under normal atmospheric oxygen conditions and then lowered to less than normal atmospheric oxygen conditions. In some embodiments, the cells are cultured under lower oxygen levels during early differentiation and then under higher oxygen levels during late differentiation.

Examples of non-adherent cell culture plates include those manufactured by Nunc (e.g., Hydrocell Cat No. 174912), etc.

The clusters can comprise at least 50-500,000, 50-100,000, 50-50,000, 50-10,000, 50-5000, 50-1000 cells. According to one embodiment, the cells in the clusters are not organized into layers and form irregular shapes. In one embodiment, the clusters are devoid of pluripotent embryonic stem cells. In another embodiment, the clusters comprise small amounts of pluripotent embryonic stem cells (e.g. no more than 5%, or no more than 3% (e.g. 0.01-2.7%) cells that co-express OCT4 and TRA-1-60 at the protein level). Typically, the clusters comprise cells that have been partially differentiated under the influence of nicotinamide. Such cells primarily express neural and retinal precursor markers such as PAX6, Rax, Six3 and/or CHX10.

The clusters may be dissociated using enzymatic or non-enzymatic methods (e.g., mechanical) known in the art. According to some embodiments, the cells are dissociated such that they are no longer in clusters—e.g. aggregates or clumps of 2-100,000 cells, 2-50,000 cells, 2-10,000 cells, 2-5000 cells, 2-1000 cells, 2-500 cells, 2-100 cells, 2-50 cells. According to a particular embodiment, the cells are in a single cell suspension.

The cells (e.g., dissociated cells) can then be plated on an adherent substrate and cultured in the presence of nicotinamide e.g. between 0.01-100 mM, 0.1-100 mM, 0.1-50 mM, 5-50 mM, 5-20 mM, e.g., 10 mM (and the absence of activin A). This stage may be effected for a minimum of 1 day, more preferably two days, three days, 1 week or even 14 days. Preferably, the cells are not cultured for more than 3 weeks in the presence of nicotinamide (and in the absence of activin). In an exemplary embodiment, this stage is effected for 6-7 days.

According to other embodiments, when the cells are cultured on the adherent substrate e.g., laminin, the atmospheric oxygen conditions are 20%. They may be manipulated such that the percentage is less than about 20%, 15%, 10%, more preferably less than about 9%, less than about 8%, less than about 7%, less than about 6% and more preferably about 5% (e.g., between 1%-20%, 1%-10% or 0-5%).

According to some embodiments, the cells are cultured on the adherent substrate initially under normal atmospheric oxygen conditions and subsequently the oxygen is lowered to less than normal atmospheric oxygen conditions. According to other embodiments, the cells are cultured on the adherent substrate initially under lower than normal atmospheric oxygen conditions and subsequently the oxygen is raised to normal atmospheric oxygen conditions.

Examples of adherent substrates or a mixture of substances could include but are not limited to fibronectin, laminin, polyD-lysine, collagen and gelatin.

Step (b): Following the first stage of directed differentiation, (step a; i.e. culture in the presence of nicotinamide (e.g., between 0.01-100 mM, 0.1-100 mM, 0.1-50 mM, 5-50 mM, 5-20 mM, e.g., 10 mM), the partially-differentiated cells are then subjected to a further stage of differentiation on an adherent substrate—culturing in the presence of activin A (e.g., 0.01-1000 ng/ml, 0.1-200 ng/ml, 1-200 ng/ml—for example 140 ng/ml, 150 ng/ml, 160 ng/ml or 180 ng/ml). Thus, activin A may be added at a final molarity of 0.1 pM-10 nM, 10 pM-10 nM, 0.1 nM-10 nM, 1 nM-10 nM, for example 5.4 nM.

Nicotinamide may be added at this stage too (e.g., between 0.01-100 mM, 0.1-100 mM, 0.1-50 mM, 5-50 mM, 5-20 mM, e.g., 10 mM). This stage may be effected for 1 day to 10 weeks, 3 days to 10 weeks, 1 week to 10 weeks, one week to eight weeks, one week to four weeks, for example for at least one day, at least two days, at least three days, at least 5 days, at least one week, at least 9 days, at least 10 days, at least two weeks, at least three weeks, at least four weeks, at least five weeks, at least six weeks, at least seven weeks, at least eight weeks, at least nine weeks, at least ten weeks.

According to some embodiments, this stage is effected for about eight days to about two weeks. This stage of differentiation may be effected at low or normal atmospheric oxygen conditions, as detailed herein above.

Step (b*): Following the second stage of directed differentiation (i.e., culture in the presence of nicotinamide and activin A on an adherent substrate; step (b), the further differentiated cells are optionally subjected to a subsequent stage of differentiation on the adherent substrate—culturing in the presence of nicotinamide (e.g., between 0.01-100 mM, 0.1-100 mM, 0.1-50 mM, 5-50 mM, 5-20 mM, e.g., 10 mM), in the absence of activin A. This stage may be effected for at least one day, 2, days, 5 days, at least one week, at least two weeks, at least three weeks or even four weeks. This stage of differentiation may also be carried out at low or normal atmospheric oxygen conditions, as detailed herein above.

The basic medium in which the ESCs are differentiated is any known cell culture medium known in the art for supporting cells growth in vitro, typically, a medium comprising a defined base solution, which includes salts, sugars, amino acids and any other nutrients required for the maintenance of the cells in the culture in a viable state. According to a specific embodiment, the basic medium is not a conditioned medium. Non-limiting examples of commercially available basic media that may be utilized in accordance with the invention comprise NUTRISTEM® (without bFGF and TGF for ESC differentiation, with bFGF and TGF for ESC expansion), NEUROBASAL™, KO-DMEM, DMEM, DMEM/F12, CELLGRO™ Stem Cell Growth Medium, or X-VIVO™. The basic medium may be supplemented with a variety of agents as known in the art dealing with cell cultures. The following is a non-limiting reference to various supplements that may be included in the culture to be used in accordance with the present disclosure: serum or with a serum replacement containing medium, such as, without being limited thereto, knock out serum replacement (KOSR), NUTRIDOMA-CS, TCH™, N2, N2 derivative, or B27 or a combination; an extracellular matrix (ECM) component, such as, without being limited thereto, fibronectin, laminin, collagen and gelatin. The ECM may then be used to carry the one or more members of the TGFβ superfamily of growth factors; an antibacterial agent, such as, without being limited thereto, penicillin and streptomycin; and non-essential amino acids (NEAA), neurotrophins which are known to play a role in promoting the survival of SCs in culture, such as, without being limited thereto, BDNF, NT3, NT4.

According to some embodiments, the medium used for differentiating the ESCs is NUTRISTEM® medium (Biological Industries, 06-5102-01-IA).

According to some embodiments, differentiation and expansion of ESCs are performed under xeno free conditions.

According to other embodiments, the proliferation/growth medium is devoid of xeno contaminants i.e., free of animal derived components such as serum, animal derived growth factors and albumin. Thus, according these embodiments, the culturing is performed in the absence of xeno contaminants.

Other methods for culturing ESCs under xeno free conditions are provided in U.S. Patent Application No. 20130196369, the contents of which are incorporated herein by reference in its entirety.

The preparations comprising RPE cells may be prepared in accordance with Good Manufacturing Practices (GMP) (e.g., the preparations are GMP-compliant) and/or current Good Tissue Practices (GTP) (e.g., the preparations may be GTP-compliant).

During differentiation steps, the embryonic stem cells may be monitored for their differentiation state. Cell differentiation can be determined upon examination of cell or tissue-specific markers which are known to be indicative of differentiation.

Tissue/cell specific markers can be detected using immunological techniques well known in the art [Thomson J A et al., (1998). Science 282: 1145-7]. Examples include, but are not limited to, flow cytometry for membrane-bound or intracellular markers, immunohistochemistry for extracellular and intracellular markers and enzymatic immunoassay, for secreted molecular markers.

Following the stages of differentiation described herein above, a mixed cell population can be obtained comprising both pigmented and non-pigmented cells.

According to this aspect, the cells of the mixed cell population are removed from the plate. In some embodiments, this is effected enzymatically (e.g., using trypsin, (TrypLE Select); see for example, international patent application publication No. WO 2017/021973, incorporated by reference herein in its entirety). According to this aspect of the present invention, at least 10%, 20%, 30%, at least 40%, at least 50%, at least 60%, at least 70% of the cells which are removed from the culture (and subsequently expanded) are non-pigmented cells. In other embodiments, this is effected mechanically—e.g., using a cell scraper. In yet other embodiments, this is effected chemically (e.g., EDTA). Combinations of enzymatic and chemical treatment are also contemplated. For example, EDTA and enzymatic treatments can be used.

Furthermore, at least 10%, 20% or even 30% of the cells which are removed from the culture (and subsequently expanded) are pigmented cells.

According to this aspect of the present disclosure, at least 50%, 60%, 70%, 80%, 90%, 95%, 100% of all the cells in the culture are removed (and subsequently expanded).

Expansion of the mixed population of cells may be effected on an extra cellular matrix, e.g., gelatin, collagen I, collagen IV, laminin (e.g., laminin 521), fibronectin and poly-D-lysine. For expansion, the cells may be cultured in serum-free KOM, serum comprising medium (e.g., DMEM with 20% human serum) or NUTRISTEM® medium (06-5102-01-IA, Biological Industries). Under these culture conditions, after passaging under suitable conditions, the ratio of pigmented cells to non-pigmented cells increases such that a population of purified RPE cells is obtained. Such cells show the characteristic polygonal shape morphology and pigmentation of RPE cells.

In one embodiment, the expanding is effected in the presence of nicotinamide (e.g., between 0.01-100 mM, 0.1-100 mM, 0.1-50 mM, 5-50 mM, 5-20 mM, e.g., 10 mM), and in the absence of activin A.

The mixed population of cells may be expanded in suspension (with or without a micro-carrier) or in a monolayer. The expansion of the mixed population of cells in monolayer cultures or in suspension culture may be modified to large scale expansion in bioreactors or multi/hyper stacks by methods well known to those versed in the art.

According to some embodiments, the expansion phase is effected for at least one 20 weeks, at least 2 weeks, at least 3 weeks, at least 4 weeks, at least 5 weeks, at least 6 weeks, at least 7 weeks, at least 8 weeks, at least 9 weeks or even 10 weeks. Preferably, the expansion phase is effected for 1 week-10 weeks, more preferably 2 weeks-10 weeks, more preferably, 3 weeks-10 weeks, more preferably 4 weeks-10 weeks, or 4 weeks-8 weeks.

According to still other embodiments, the mixed population of cells are passaged at least 1 time during the expansion phase, at least twice during the expansion phase, at least three times during the expansion phase, at least four times during the expansion phase, at least five times during the expansion phase, or at least six times during the expansion phase.

The present inventors have shown that when cells are collected enzymatically, it is possible to continue the expansion for more than 8 passages, more than 9 passages and even more than 10 passages (e.g., 11-15 passages). The number of total cell doublings can be increased to greater than 30, e.g., 31, 32, 33, 34 or more. (See international patent application publication number WO 2017/021973, incorporated herein by reference in its entirety).

The population of RPE cells generated according to the methods described herein may be characterized according to a number of different parameters. Thus, for example, the RPE cells obtained may be polygonal in shape and pigmented.

It will be appreciated that the cell populations disclosed herein are generally devoid of undifferentiated human embryonic stem cells. According to some embodiments, less than 1:250,000 cells are Oct4+TRA-1-60+ cells, as measured for example by FACS. The cells may also have down regulated (by more than 5,000 fold) expression of GDF3 or TDGF as measured by PCR. The RPE cells of this aspect, do not express embryonic stem cell markers. Said one or more embryonic stem cell markers may comprise OCT-4, NANOG, Rex-1, alkaline phosphatase, Sox2, TDGF-beta, SSEA-3, SSEA-4, TRA-1-60, and/or TRA-1-81.

The therapeutic RPE cell preparations may be substantially purified, with respect to non-RPE cells, comprising at least about 75%, 80%, 85%, 90%, 91%, 92%, 93%, 94%, 95%, 96%, 97%, 98%, 99%, or 100% RPE cells. The therapeutic RPE cell preparation may be essentially free of non-RPE cells or consist of RPE cells. For example, the substantially purified preparation of RPE cells may comprise less than about 25%, 20%, 15%, 10%, 9%, 8%, 7%, 6%, 5%, 4%, 3%, 2%, or 1% non-RPE cell type. For example, the RPE cell preparation may comprise less than about 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% non-RPE cells.

The RPE cell preparations may be substantially pure, both with respect to non-RPE cells and with respect to RPE cells of other levels of maturity. The preparations may be substantially purified, with respect to non-RPE cells, and enriched for mature RPE cells. For example, in RPE cell preparations enriched for mature RPE cells, at least about 30%, 40%, 45%, 50%, 55%, 60%, 65%, 70%, 75%, 80%, 85%, 90%, 91%, 92%, 93%, 94%, 95%, 96%, 97%, 98%, 99%, 99%, or 100% of the RPE cells are mature RPE cells. The preparations may be substantially purified, with respect to non-RPE cells, and enriched for differentiated RPE cells rather than mature RPE cells. For example, at least about 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the RPE cells may be differentiated RPE cells rather than mature RPE cells.

The preparations described herein may be substantially free of bacterial, viral, or fungal contamination or infection, including but not limited to the presence of HIV I, HIV 2, HBV, HCV, HAV, CMV, HTLV 1, HTLV 2, parvovirus B19, Epstein-Barr virus, or herpesvirus 1 and 2, SV40, HHV5, 6, 7, 8, CMV, polyoma virus, HPV, Enterovirus. The preparations described herein may be substantially free of *mycoplasma* contamination or infection.

Another way of characterizing the cell populations disclosed herein is by marker expression. Thus, for example, at least 50%, 60% 70%, 80%, 85%, 90%, 95% or 100% of the cells may express Bestrophin 1, as measured by immunostaining. According to one embodiment, between 80-100% of the cells express bestrophin 1.

According to other embodiments, at least 80%, 85%, 87%, 89%, 90%, 95%, 97% or 100% of the cells express Microphthalmia-associated transcription factor (MITF), as measured by immunostaining. For example, between 80-100% of the cells express MITF.

According to other embodiments, at least 50%, 60% 70%, 80%, 85%, 87%, 89%, 90%, 95%, 97% or 100% of the cells express both Microphthalmia-associated transcription factor (MITF) and bestrophin 1, as measured by immunostaining. For example, between 80-100% of the cells co-express MITF and bestrophin 1.

According to other embodiments, at least 80%, 85%, 87%, 89%, 90%, 95%, 97% or 100% of the cells express both Microphthalmia-associated transcription factor (MITF) and Z0-1, as measured by immunostaining. For example, between 80-100% of the cells co-express MITF and Z0-1.

According to other embodiments, at least 50%, 60% 70%, 80%, 85%, 87%, 89%, 90%, 95%, 97% or 100% of the cells express both Z0-1 and bestrophin 1, as measured by immunostaining. For example, between 80-100% of the cells co-express Z0-1 and bestrophin 1.

According to another embodiment, at least 50%, 60% 70% 80%, 85%, 87%, 89%, 90%, 95%, 97% or 100% of the cells express paired box gene 6 (PAX-6) as measured by immunostaining or FACS.

According to another embodiment, at least 50%, 60% 70%, 80%, 85%, 87%, 89%, 90%, 95%, 97% or 100% of the cells express cellular retinaldehyde binding protein (CRALBP), as measured by immunostaining. For example, between 85-100% of the cells express CRALBP.

According to another embodiment, at least 50%, 60% 70%, 80%, 85%, 87%, 89%, 90%, 95%, 97% or 100% of the cells express cellular Melanocytes Lineage-Specific Antigen GP100 (PMEL17), as measured by immunostaining. For example, between 85-100% of the cells express PMEL17.

The RPE cells typically co-express markers indicative of terminal differentiation, e.g. bestrophin 1, CRALBP and/or RPE65. In addition, the RPE cells described herein may express markers for RPE primary cilia, such as ARL13B and GT335.

Following the expansion phase, cell populations comprising RPE cells are obtained whereby at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% thereof are CRALBP+PMEL1 7+.

In certain embodiments, RPE cell compositions may be produced according to the following methods: (1) culturing hESCs on hUCFs in center well (CW) plates for 2 weeks in NUT+ with human serum albumin (HSA), (2) mechanical passaging to expand the hESCs on hUCFs in CW plates for between four to five weeks (or until desired amount of cells) in NUT+ with HSA, (3) continue to expand hESC colonies (using for example, collagenase) on hUCFs in 6 cm plates for an additional week in NUT+ with HSA, (4) prepare spheroid bodies (SB) by transferring colonies from about five 6 cm plates into 1 HydroCell for about one week in NUT− with nicotinamide (NIC), (5) flattening of SBs on Lam511 may be carried out by transferring the SBs to 2-3 wells of a 6-well plate for about one week in NUT− with NIC, (6) culture adherent cells on Lam511 in NUT− with NIC and Activin for about one to two weeks and replace media with NUT− with NIC and culture for between one and three weeks, (7) enrich for pigmented cells using enzymes, such as TrypLE Select for example, (8) expand RPE cells on gelatin in flasks for between about two to nine weeks (replacing media) in 20% human serum and NUT−, and (9) harvest RPE cells.

Harvesting of the expanded population of RPE cells may be carried out using methods known in the art (e.g. using an enzyme such as trypsin, or chemically using EDTA, etc). In some embodiments, the RPE cells may be washed using an appropriate solution, such as PBS or BSS plus. In some embodiments, an enzyme neutralizing solution may be used subsequent to harvesting or enriching for RPE cells. The neutralizing solution may comprise for example, medium with or without human serum or human serum albumin. In some embodiments, prolonged incubation in enzyme neutralizing solution with or without HS or HAS has no effect on cell viability or cell recovery.

In other embodiments, the RPE cells may be filtered prior to formulation of the RPE cells for cryopreservation and administration to a subject directly after thawing. In some embodiments, the percent viability of post-filtered cells is at least about 75%, 80%, 85%, 90%, 91%, 92%, 93%, 94%, 95%, 96%, 97%, 98%, 99%, or 100%. In some embodiments, the percent viability of post-filtered cells stored in a neutralization solution for between about 0 to about 8 hours is at least about 75%, 80%, 85%, 90%, 91%, 92%, 93%, 94%, 95%, 96%, 97%, 98%, 99%, or 100%.

Following harvesting, the expanded population of RPE cells can be formulated at a specific therapeutic dose (e.g., number of cells) and cryopreserved for shipping to the clinic. The ready to administer (RTA) RPE cell therapy composition can then be administered directly after thawing without further processing. Examples of media suitable for cryopreservation include but are not limited to 90% Human Serum/10% DMSO, Media 3 10% (CS10), Media 2 5% (CS5) and Media 1 2% (CS2), Stem Cell Banker, PRIME XV® FREEZIS, HYPOTHERMASOL®, CSB, Trehalose, etc.

In some embodiments, the percent viability of post-filtered cells stored in a cryopreservation medium for between about 0 to about 8 hours is at least about 75%, 80%, 85%, 90%, 91%, 92%, 93%, 94%, 95%, 96%, 97%, 98%, 99%, or 100%. In other embodiments, the percent recovery of post-filtered cells stored in a cryopreservation medium for between about 0 to about 8 hours is at least about 75%, 80%, 85%, 90%, 91%, 92%, 93%, 94%, 95%, 96%, 97%, 98%, 99%, or 100%.

In further embodiments, the percent viability of post-filtered cells stored in a neutralization medium for between about 0 to about 8 hours followed by storage in cryopreservation medium for between about 0 to about 8 hours is at least about 75%, 80%, 85%, 90%, 91%, 92%, 93%, 94%, 95%, 96%, 97%, 98%, 99%, or 100%. In other embodiments, the percent recovery of post-filtered cells stored in a neutralization medium for between about 0 to about 8 hours followed by storage in cryopreservation medium for between about 0 to about 8 hours is at least about 70%, 75%, 80%, 85%, 90%, 91%, 92%, 93%, 94%, 95%, 96%, 97%, 98%, 99%, or 100%.

In yet other embodiments, the percent viability of post-filtered cells stored in a neutralization medium for between about 0 to about 8 hours followed by storage in cryopreservation medium for between about 0 to about 8 hours, post-thawing of the cryopreserved composition, is at least about 75%, 80%, 85%, 90%, 91%, 92%, 93%, 94%, 95%, 96%, 97%, 98%, 99%, or 100%. In still other embodiments, the percent recovery of post-filtered cells stored in a neutralization medium for between about 0 to about 8 hours followed by storage in cryopreservation medium for between about 0 to about 8 hours, post-thawing of the cryopreserved composition, is at least about, 70%, 75%, 80%, 85%, 90%, 91%, 92%, 93%, 94%, 95%, 96%, 97%, 98%, 99%, or 100%.

In some embodiments, post-filtered RPE cells stored in a neutralization medium for between about 0 to about 8 hours followed by storage in cryopreservation medium for between about 0 to about 8 hours, post-thawing of the cryopreserved composition are capable of secreting PEDF at between about 1,500 ng/ml/day to about 4,500 ng/ml/day, about 2,000 ng/ml/day to about 3,000 ng/ml/day. In other embodiments, post-filtered RPE cells stored in a neutralization medium for between about 0 to about 8 hours followed by storage in cryopreservation medium for between about 0 to about 8 hours, post-thawing of the cryopreserved composition are capable of being expanded to at least between about $1.2\times10^6$ and $5\times10^6$, or about $2.5\times\times10^6$ to about $4\times10^6$ cells in 14 days.

In some embodiments, the percent viability of post-filtered RPE cells stored in a neutralization medium for between about 0 to about 8 hours at room temperature is at least about, 70%, 75%, 80%, 85%, 90%, 91%, 92%, 93%, 94%, 95%, 96%, 97%, 98%, 99%, or 100%. In some embodiments, the percent viability of post-filtered RPE cells stored in a cryopreservation medium for between about 0 to about 8 hours at room temperature is at least about, 70%, 75%, 80%, 85%, 90%, 91%, 92%, 93%, 94%, 95%, 96%, 97%, 98%, 99%, or 100%. In further embodiments, the percent viability of post-filtered cells stored in a neutralization solution at room temperature for between about 0 to about 8 hours followed by storage in cryopreservation medium for between about 0 to about 8 hours at room temperature is at least about 75%, 80%, 85%, 90%, 91%, 92%, 93%, 94%, 95%, 96%, 97%, 98%, 99%, or 100%. In still further embodiments, the percent recovery of post-filtered cells stored in a neutralization solution at room temperature for between about 0 to about 8 hours followed by storage in cryopreservation medium for between about 0 to about 8 hours at room temperature is at least about 75%, 80%, 85%, 90%, 91%, 92%, 93%, 94%, 95%, 96%, 97%, 98%, 99%, 100%, 105%, 110%, 115%, 120%, 125%, 130%, 140%, 150%.

RPE cells formulated in cryopreservation media appropriate for post thaw ready to administer (RTA) applications may comprise RPE cells suspended in adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water. An example of this cryopreservation media is available commercially under the tradename, CRYOSTOR® and is manufactured by BioLife Solutions, Inc.

DMSO can be used as a cryoprotective agent to prevent the formation of ice crystals, which can kill cells during the cryopreservation process. In some embodiments, the cryopreservable RPE cell therapy composition comprises between about 0.1% and about 2% DMSO (v/v). In some embodiments, the RTA RPE cell therapy composition comprises between about 1% and about 20% DMSO. In some embodiments, the RTA RPE cell therapy composition comprises about 2% DMSO. In some embodiments, the RTA RPE cell therapy composition comprises about 5% DMSO.

In some embodiments, RPE cell therapies formulated in cryopreservation media appropriate for post thaw ready to administer (RTA) applications may comprise RPE cells suspended in cryopreservation media that does not contain DMSO. For example, RTA RPE therapeutic cell compositions may comprise RPE cells suspended in Trolox, Na+, K+, Ca2+, Mg2+, c1−, H2P04−, HEPES, lactobionate, sucrose, mannitol, glucose, dextran-40, adenosine, glutathione without DMSO (dimethyl sulfoxide, $(CH_3)_2SO$) or any other dipolar aprotic solvents. An example of this cryopreservation media is available commercially under the tradename, HYPOTHERMOSOL® or HYPOTHERMOSOL®-FRS and is also manufactured by BioLife Solutions, Inc. In other embodiments, RPE cell compositions formulated in cryopreservation media appropriate for post thaw ready to administer applications may comprise RPE cells suspended in Trehalose.

The RTA RPE cell therapy composition may optionally comprise additional factors that support RPE engraftment, integration, survival, potency, etc. In some embodiments, the RTA RPE cell therapy composition comprises activators of function of the RPE cell preparations described herein. In some embodiments, the RTA RPE cell therapy composition comprises nicotinamide. In some embodiments, the RTA RPE cell therapy composition comprises nicotinamide at a concentration of between about 0.01-100 mM, 0.1-100 mM, 0.1-50 mM, 5-50 mM, 5-20 mM, e.g., 10 mM. In other embodiments, the RTA RPE cell therapy composition comprises retinoic acid. In some embodiments, the RTA RPE cell therapy composition comprises retinoic acid at a concentration of between about 0.01-100 mM, 0.1-100 mM, 0.1-50 mM, 5-50 mM, 5-20 mM, e.g., 10 mM.

In some embodiments, the RTA RPE cell therapy composition may be formulated to include activators of various integrins that have been shown to increase the adherence of the RPE cell preparations, such as those described herein, to the Brunch's membrane. For example, in some embodiments, the RTA RPE cell therapy composition comprises extracellular manganese (Mn2+) at a concentration of between about 5 μM and 1,000 μM. In other embodiments, the RTA RPE cell therapy composition comprises the conformation-specific monoclonal antibody, TS2/16.

In other embodiments, the RTA RPE cell therapy composition may also be formulated to include activators of RPE cell immune regulatory activity.

In some embodiments, the RTA RPE cell therapy composition may include a ROCK inhibitor.

In some embodiments, the RTA RPE cell therapy composition may be formulated in a medium comprising components that decrease the molecular cell stress during freezing and thawing processes by scavenging of free radicals, pH buffering, oncotic/osmotic support and maintenance of the ionic concentration balance.

In some embodiments, RPE cell therapies formulated in cryopreservation media appropriate for post thaw ready to administer applications may comprise one or more immunosuppressive compounds. In certain embodiments, RPE cell therapies formulated in cryopreservation media appropriate for post thaw ready to administer applications may comprise one or more immunosuppressive compounds that are formulated for slow release of the one or more immunosuppressive compounds.

Immunosuppressive compounds for use with the formulations described herein may belong to the following classes of immunosuppressive drugs: Glucocorticoids, Cytostatics (e.g. alkylating agent or antimetabolite), antibodies (polyclonal or monoclonal), drugs acting on immunophilins (e.g., cyclosporin, Tacrolimus or Sirolimus). Additional drugs include interferons, opioids, TNF binding proteins, mycophenolate and small biological agents. Examples of immunosuppressive drugs include: mesenchymal stem cells, anti-lymphocyte globulin (ALG) polyclonal antibody, anti-thymocyte globulin (ATG) polyclonal antibody, azathioprine, BAS 1LI X IMAB® (anti-I L-2Ra receptor antibody), cyclosporin (cyclosporin A), DACLIZUMAB® (anti-I L-2Ra receptor antibody), everolimus, mycophenolic acid, RITUX IMAB® (anti-CD20 antibody), sirolimus, tacrolimus, Tacrolimus and or Mycophenolate mofetil.

The number of viable cells that may be administered to the subject are typically between at least about 50,000 and about $5\times10^6$ per dose. In some embodiments, the RTA RPE cell therapy composition comprises at least 100,000 viable cells. In some embodiments, the RTA RPE cell therapy composition comprises at least 150,000 viable cells. In some embodiments, the RTA RPE cell therapy composition comprises at least 200,000 viable cells. In some embodiments, the RTA RPE cell therapy composition comprises at least 250,000 viable cells. In some embodiments, the RTA RPE cell therapy composition comprises at least 300,000 viable cells. In some embodiments, the RTA RPE cell therapy composition comprises at least 350,000 viable cells. In some embodiments, the RTA RPE cell therapy composition comprises at least 400,000 viable cells. In some embodiments, the RTA RPE cell therapy composition comprises at least 450,000 viable cells. In some embodiments, the RTA RPE cell therapy composition comprises at least 500,000 viable cells. In some embodiments, the RTA RPE cell therapy composition comprises at least 600,000, at least 700,000, at least 800,000, at least 900,000, at least 1,000,000, at least, 2,000,000, at least 3,000,000, at least, 4,000,000, at least 5,000,000 at least 6,000,000, at least 7,000,000, at least 8,000,000, at least 9,000,000, at least 10,000,000, at least 11,000,000, or at least 12,000,000 viable cells.

In some embodiments, the volume of the RTA RPE formulation administered to the subject is between about 50 μl to about 100 μl, about 25 μl to about 100 μl, about 100 μl to about 150 μl, or about 10 μl to about 200 μl. In certain embodiments, two doses of between 10 μl and 200 μl of the RTA RPE formulation can be administered. In certain embodiments, the volume of RTA RPE formulation is administered to the subretinal space of a subject's eye. In certain embodiments, the subretinal delivery method can be transvitreal or suprachoroidal. In some embodiments, the volume of RTA RPE formulation can be injected into the subject's eye.

In certain embodiments, the RTA RPE therapeutic cell compositions may be formulated at a cell concentration of between about 100,000 cells/ml to about 1,000,000 cells/ml. In certain embodiments, the RTA RPE cell therapy may be formulated at a cell concentration of about 1,000,000 cells/ml, about 2,000,000 cells/ml, about 3,000,000 cells/ml, about 4,000,000 cells/ml, about 5,000,000 cells/ml, 6,000,000 cells/ml, 7,000,000 cells/ml, 8,000,000 cells/ml, about 9,000,000 cells/ml, about 10,000,000 cells/ml, about 11,000,000 cells/ml, about 12,000,000 cells/ml, 13,000,000 cells/ml, 14,000,000 cells/ml, 15,000,000 cells/ml, 16,000,000 cells/ml, about 17,000,000 cells/ml, about 18,000,000 cells/ml, about 19,000,000 cells/ml, or about 20,000,000 cells/ml.

In some embodiments, the RTA RPE cell therapy composition may be cryopreserved and stored at a temperature of between about −4° C. to about −200° C. In some embodiments, the RTA RPE cell therapy composition may be cryopreserved and stored at a temperature of between about −20° C. to about −200° C. In some embodiments, the RTA RPE cell therapy composition may be cryopreserved and stored at a temperature of between about −70° C. to about −196° C. In some embodiments, the temperature adequate for cryopreservation or a cryopreservation temperature, comprises a temperature of between about −4° C. to about −200° C., or a temperature of between about −20° C. to about −200° C., −70° C. to about −196° C. In some embodiments, the RTA RPE cell therapy composition may be stored frozen for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In other embodiments, the RPE cells may be stored frozen for between about 1.5 to 48 months. In other embodiments, the RTA RPE cell therapy composition may be stored frozen for between about 1 to about 48 months without a decrease in percent viability or cell recovery. In some embodiments, the RTA RPE cell therapy composition may be stored for at least about 38 hours at 2-8° C., while maintaining stability.

In some embodiments, the RTA RPE cell therapy composition may be shipped frozen over 8,000 miles without a decrease in percent viability, percent cell recovery, or potency.

It would be well appreciated by those versed in the art that the derivation of RPE cells is of great benefit. They may be used as an in vitro model for the development of new drugs to promote their survival, regeneration and function. RPE cells may serve for high throughput screening for compounds that have a toxic or regenerative effect on RPE cells. They may be used to uncover mechanisms, new genes, soluble or membrane-bound factors that are important for the development, differentiation, maintenance, survival and function of photoreceptor cells.

The RPE described herein cells may also serve as an unlimited source of RPE cells for transplantation, replenishment and support of malfunctioning or degenerated RPE cells in retinal degenerations and other degenerative disorders. Furthermore, genetically modified RPE cells may serve as a vector to carry and express genes in the eye and retina after transplantation.

Eye conditions for which the RPE cells may serve as therapeutics include, but are not limited to retinal diseases or disorders generally associated with retinal dysfunction, retinal injury, and/or loss of retinal pigment epithelium. A non-limiting list of conditions which may be treated in accordance with the invention comprises retinitis pigmentosa, lebers congenital amaurosis, hereditary or acquired macular degeneration, age related macular degeneration (AMD), non-exudative (dry) AMD, Geographic Atrophy (GA), Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neo vascular or traumatic injury.

Exemplary degenerative disorders that may be treated using the cells of this aspect of the present invention include neurodegenerative disorders including but not limited to Parkinson's, ALS, Multiple Sclerosis, Huntingdon's disease, autoimmune encephalomyelitis, diabetic neuropathy, Alzheimer's and epilepsy.

Subjects which may be treated include primate (including humans), canine, feline, ungulate (e.g., equine, bovine, swine (e.g., pig)), avian, and other subjects. Humans and non-human animals having commercial importance (e.g., livestock and domesticated animals) are of particular interest. Exemplary mammals which may be treated include, canines; felines; equines; bovines; ovines; rodentia, etc. and primates, particularly humans. Non-human animal models, particularly mammals, e.g. primate, murine, lagomorpha, etc. may be used for experimental investigations.

The RPE cells generated as described herein may be transplanted to various target sites within a subject's eye or other locations (for example in the brain). In accordance with one embodiment, the transplantation of the RPE cells is to the subretinal space of the eye, which is the normal anatomical location of the RPE (between the photoreceptor outer segments and the choroid). In addition, dependent upon migratory ability and/or positive paracrine effects of the cells, transplantation into additional ocular compartments can be considered including but not limited to the vitreal space, inner or outer retina, the retinal periphery and within the choroids.

The transplantation may be performed by various techniques known in the art. Methods for performing RPE transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Ophthalmology April 2000; 107 (4): 719-24; and Jpn J Ophthalmol November-December 1999; 43(6): 502-8. If mainly paracrine effects are to be utilized, cells may also be delivered and maintained in the eye encapsulated within a semi-permeable container, which will also decrease exposure of the cells to the host immune system (Neurotech USA CNTF delivery system; PNAS Mar. 7, 2006 vol. 103(10) 3896-3901).

The step of administering may comprise intraocular administration of the RPE cells into an eye in need thereof. The intraocular administration may comprise injection of the RPE cells into the subretinal space.

In accordance with one embodiment, transplantation is performed via pars plana vitrectomy surgery followed by delivery of the cells through a small retinal opening into the sub-retinal space or by direct injection.

In certain embodiments, administration may comprise a vitrectomy followed by delivery of the RTA therapeutic cell composition into the subretinal space in the macular area via a cannula through a small retinotomy. A total volume of 50-100 μL cell suspension, depending on the cell dose can be implanted in areas at potential risk for GA expansion.

In some embodiments, a single surgical procedure is performed in which the RTA therapeutic cell composition is delivered through a small retinotomy, following vitrectomy, into a subretinal space created in the macular area, along the border between areas of GA, if present, and the better preserved extra-foveal retina and RPE layer. After the placement of a lid speculum, a standard 3-port vitrectomy can be performed. This may include the placement of a 23G or 25G infusion cannula and two 23G or 25/23G ports (trocars). A core vitrectomy can then be performed with 23G or 25G instruments, followed by detachment of the posterior vitreous face. The RTA therapeutic cell composition may be injected into the subretinal space at a predetermined site within the posterior pole, preferably penetrating the retina in an area that is still relatively preserved close to the border of GA, if present.

In some embodiments, the cell composition is administered by a suprachoroidal injection.

The RPE cells may be transplanted in various forms. For example, the RPE cells may be introduced into the target site in the form of single cell suspension, with matrix or adhered onto a matrix or a membrane, extracellular matrix or substrate such as a biodegradable polymer or a combination. The RPE cells may also be printed onto a matrix or scaffold. The RPE cells may also be transplanted together (co-transplantation) with other retinal cells, such as with photoreceptors. The effectiveness of treatment may be assessed by different measures of visual and ocular function and structure, including, among others, best corrected visual acuity (BCVA), retinal sensitivity to light as measured by perimetry or microperimetry in the dark and light-adapted states, full-field, multi-focal, focal or pattern electroretinography 5 ERG), contrast sensitivity, reading speed, color vision, clinical biomicroscopic examination, fundus photography, optical coherence tomography (OCT), fundus autofluorescence (FAF), infrared and multicolor imaging, fluorescein or ICG angiography, adoptive optics and additional means used to evaluate visual function and ocular structure.

The subject may be administered corticosteroids prior to or concurrently with the administration of the RPE cells, such as prednisolone or methylprednisolone, Predforte. According to another embodiment, the subject 1s not administered corticosteroids prior to or concurrently with the administration of the RPE cells, such as prednisolone or methylprednisolone, Predforte.

Immunosuppressive drugs may be administered to the subject prior to, concurrently with and/or following treatment. The immunosuppressive drug may belong to the following classes: Glucocorticoids, Cytostatics (e.g. alkylating agent or antimetabolite), antibodies (polyclonal or monoclonal), drugs acting on immunophilins (e.g. cyclosporin, Tacrolimus or Sirolimus). Additional drugs include interferons, opioids, TNF binding proteins, mycophenolate and small biological agents. Examples of immunosuppressive drugs include: mesenchymal stem cells, anti-lymphocyte globulin (ALG) polyclonal antibody, anti-thymocyte globulin (ATG) polyclonal antibody, azathioprine, BAS 1 LI X IMAB® (anti-I L-2Ra receptor antibody), cyclosporin (cyclosporin A), DACLIZUMAB® (anti-I L-2Ra receptor antibody), everolimus, mycophenolic acid, RITUX IMAB® (anti-CD20 antibody), sirolimus, tacrolimus, Tacrolimus and or Mycophenolate mofetil.

Alternatively, the RTA RPE cell therapy composition may be administered without the use of immunosuppressive drugs.

Antibiotics may be administered to the subject prior to, concurrently with and/or following treatment. Examples of antibiotics include Oflox, Gentamicin, Chloramphenicol, Tobrex, Vigamox or any other topical antibiotic preparation authorized for ocular use.

RTA RPE cell therapies formulated according to the present disclosure do not require the use of GMP facilities for preparation of the final dose formulation prior to injection into a subject's eye. The RTA RPE cell therapy formulations described herein may be cryopreserved in a non-toxic cryosolution that comprises the final dose formulation which can be shipped directly to the clinical site. When needed, the formulation can be thawed and administered into the subject's eye without having to perform any intermediate preparation steps.

Figure 15:
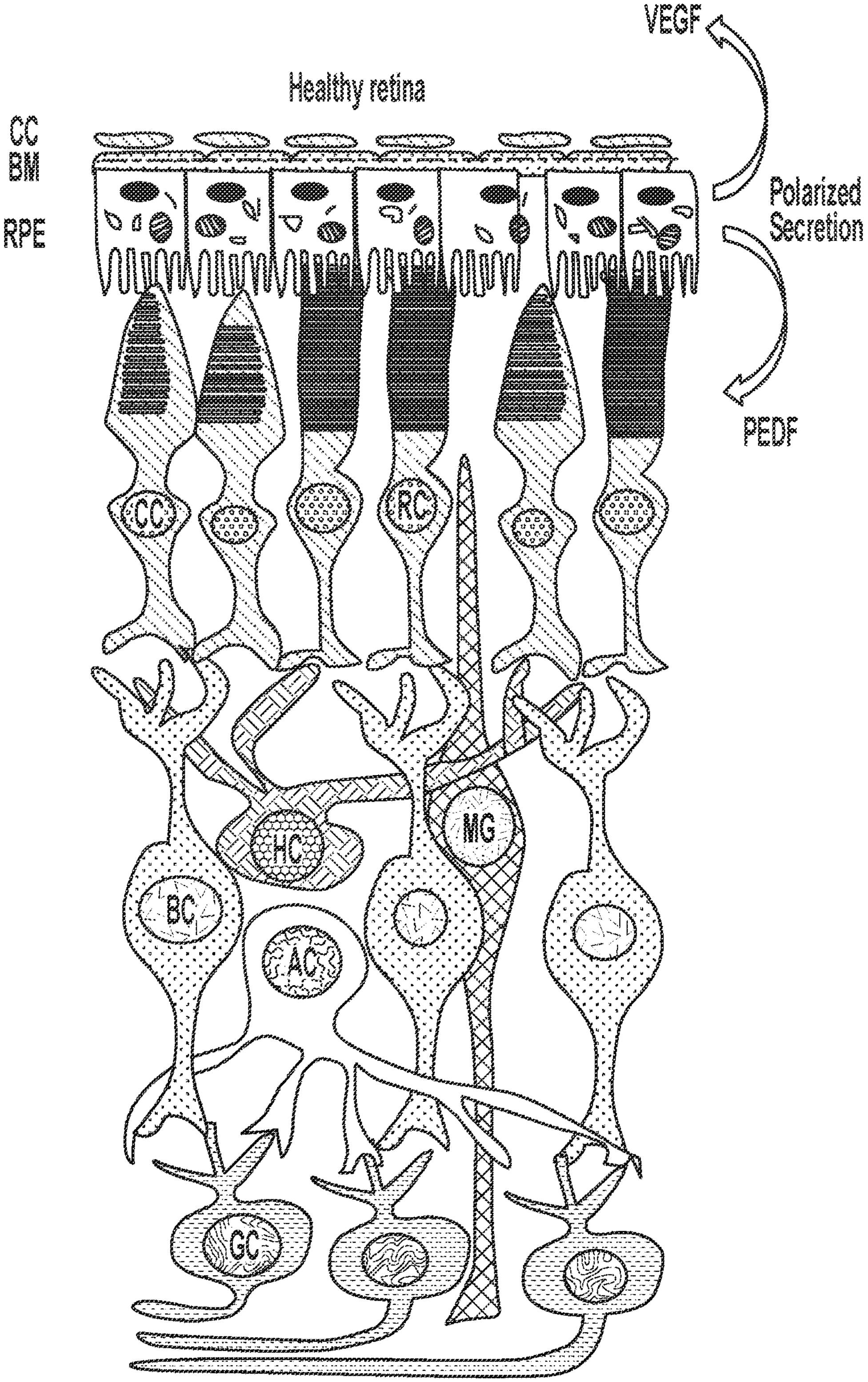
FIG. 15 is an illustration of the RPE and adjacent cells.

RPE cells are involved in many processes critical for photoreceptor survival, including nutrient, water, and ion transport, light absorption, phagocytosis of shed photoreceptor outer segments (POS), re-isomerization of all-trans-retinal into 11-cis-retinal, which is crucial for the visual cycle, immune regulation, secretion of essential factors, and formation of the blood-retinal barrier. As shown in FIG. 15, the RPE monolayer acts as a polarized metabolic gatekeeper between the PRs and the choroicapillaries (CC). The RPE has an apical to basolateral structural and functional polarity. On the apical side, RPE cells form multiple villi enabling direct contact with the POS and transport molecules such as glucose and vitamin A from the choroicapillaries to PRs. On the basal side, RPE cells transport metabolites such as CO2, lactate and water to the choroicapillaries and generate the underlying basal Bruch's membrane (BM) that separates the RPE from the choroid generating the blood-retinal barrier. On the lateral walls, adjoining RPE cells form tight junctions. Barrier function can be used to determine the potency of RPE cell cultures by measuring the tight junctions formed between the cells. RPE tight junctions limit paracellular movement of ions and water across the RPE monolayer and maintain the correct apico-basal distribution of RPE transporters. The RPE cell compositions disclosed herein display barrier function determined by the ability to generate Trans Epithelial Electrical Resistance (TEER) above 100Ω.

In addition, RPE cells secrete a variety of neurotrophic factors, such as fibroblast growth factors (bFGF and aFGF), ciliary neurotrophic factor (CNTF), pigment epithelium-derived factor (PEDF), brain-derived neurotrophic factor (BDNF), vascular endothelial growth factor (VEGF) and others, that help to maintain the structural integrity of choriocapillaris endothelium and photoreceptors. RPE cells also secrete anti-inflammatory cytokines such as transforming growth factor (TGF)-β, important in establishing the immune privileged properties of the eye. The RPE cells used in the RTA therapeutic cell compositions described herein are capable of secreting neurotrophic factors. The RPE cell compositions disclosed herein also demonstrate polarized PEDF and VEGF secretion which enhances RPE growth and blood vessel formation, respectively.

Different cell culture media can have an effect on the expansion efficiency of cells. However, the RPE cell compositions disclosed herein demonstrate the ability to expand after being suspended in media formulations comprising DMSO.

The RPE cell compositions disclosed herein also display a percentage of viable post thawed cells that allows the formulations to be used as a ready to inject cell therapy, without the need to remove dead cells. The percent yield of the RPE cell compositions disclosed herein, as measured by cells per milliliter, is characteristic of formulations that are optimized to meet large scale clinical use requirements.

Example 1

Used herein are cell suspensions of RPE cells, derived from human embryonic stem cells (hESCs) through a process of directed differentiation under xeno-free, GMP manufacturing conditions. These cells were expanded on irradiated human umbilical cord fibroblast feeders (hUCFs). The expanded hESCs were then differentiated into retinal pigment epithelium (RPE) cells using Nicotinamide and Activin A. The RPE cells were then expanded and cryopreserved in cryopreservation medium.

Xeno-free GMP grade HAD-C 102 hESCs were expanded as colonies on irradiated xeno-free GMP-grade CRD008 hUCFs that were seeded on recombinant human vitronectin (rhVTN) or on recombinant human Gelatin (rhGelatin). hESC expansion was carried out in the presence of NUTRISTEM® medium that contains human serum albumin in addition to the growth factors basic FGF and TGF beta (Biological Industries). Expanded hESCs were then transferred to a suspension culture to initiate differentiation in a directed manner under normal (atmospheric) $O_2$ conditions.

Spheroid bodies (SBs) were formed and then plated as an adherent cell culture under continued directed differentiation conditions towards a neural fate and subsequently towards an RPE cell fate.

At the end of the differentiation phase, cells were harvested using the following two techniques and expanded 1) Non-pigmented areas were manually excised and removed and the remaining pigmented cell areas were enzymatically collected, and 2) Cells (pigmented and non-pigmented) were collected enzymatically. Cells were then seeded and expanded for 3 passages on top of rhGelatin covered cell culture plates according to manufacturing instructions in the presence and absence of nicotinamide or on top of Laminin 521, Fibronectin, Collagen I or Collagen IV. Cells were harvested and cryopreserved at passage 2 (P2) in cryomedium comprised of 90% human serum and 10% DMSO, and in serum free xeno-free GMP grade cryomedia (Media 2 (CS5) and Media 1 (CS2), BioLife Solutions).

Example 2

Post thaw vitality and viability were assessed for therapeutic RPE cells cryopreserved in cryopreservation media with 5% dimethyl sulfoxide (DMSO) (Media 2, CS5) at cell densities of $1.5\times10^6$ and $5\times10^6$. Results were compared to the results of cells that were cryopreserved in 90% human serum (HS) with 10% DMSO using a controlled freezing machine (e.g., an isopropanol containing slow cooling apparatus). After thawing of 3 vials of each composition frozen in each cryopreservation media, viability was tested using a cell counter. Cells of each vial were then seeded in a 12-well plate, at a density of $0.5\times10^6$ viable cells/well in a final volume of 2 mL DMEM containing 20% human serum per well, for 24 hours at 37° C. and 5% $CO_2$. At the end of the incubation period, cultures were washed with PBS. Following TrypLE Select treatment, cells were enumerated using a cell counter. Percent vitality was then calculated by dividing the average number of viable adhered cells with the total number of seeded cells per well and multiplying the result by 100.

As shown in FIG. 1, the results demonstrate that RPE cells that were cryopreserved in the media used herein had similar post thaw viability and better post thaw vitality (better % cell adherence 24 hours post thawing) when compared to the cryopreservation medium comprised of 90% human serum and 10% DMSO (HS/DMSO).

Example 3

Therapeutic RPE cell compositions were formulated using xeno-free GMP-grade reagents, xeno-free GMP-grade cells (HAD-C 102-hESCs grown on irradiated CRD008), as described in Example 1.

Assessment of $CRALBP^+PMEL17^+$ cells for measurement of RPE purity was performed at the end of the differentiation phase. As shown in Table 1a and Table 1 b, purity of RPE cells was at least 98.76% or greater for all RTA RPE cell therapy compositions formulated with CS2 (Media 1) or CS5 (Media 2).

Tight junctions generated between RPE cells enable the generation of the blood-retinal barrier and a polarized PEDF and VEGF secretion. PEDF is secreted to the apical side where it acts as an anti-angiogenic and neurotropic growth factor. VEGF is mainly secreted to the basal side, where it acts as a proangiogenic growth factor on the choroidal endothelium. RPE polarization (barrier function and polarized PEDF and VEGF secretion) was measured in a transwell system in cells at the end of the production process. As shown in Table 1a and 1 b, barrier function/trans-epithelial electrical resistance (TEER) was demonstrated as well as polarized secretion of PEDF and VEGF.

Control samples (Ctrl) were cryopreserved in 10% DMSO and 90% human serum.

TABLE 1a

Characterization of Therapeutic RPE Cells Cryopreserved in Media 1 (CS2) and Media 2 (CS5) for Production Runs (PR) 1 and 2

| | Therapeutic RPE PR 1 Mean ± SD (n) | | | Therapeutic RPE PR 2 Mean ± SD (n) | | |
|---|---|---|---|---|---|---|
| Test (Method) | Ctrl | CS2 | CS5 | Ctrl | CS2 | CS5 |
| % Viability (Cell Counter) | 85 ± 3 (n = 3) | 87 ± 1 (n = 3) | 89 ± 3 (n = 3) | 84 (n = 2) | 84 (n = 2) | 92 (n = 2) |
| Purity (FACS): % $CRALBP^+PMEL17^+$ Cells | 99.78 | 99.54 | 99.57 | 98.74 | 99.50 | 99.87 |
| Potency: | | | | | | |
| Transepithelial Electrical Resistance (TEER) | 274 | 175 | 225 | 663 | 739 | 753 |
| Polarized PEDF Secretion (Apical to Basal Ratio) | 3.6 | 3.2 | 4.1 | 4.0 | 6.6 | 6.1 |
| Polarized VEGF Secretion (Basal to Apical Ratio) | 1.4 | 1.5 | 1.7 | 3.7 | 2.3 | 2.2 |

TABLE 1b

Characterization of Therapeutic RPE Cells Cryopreserved in Media 1 (CS2) and Media 2 (CS5) for Experiments (PR) 3 and 4

| | Therapeutic RPE ® PR 3 Mean ± SD (n) | | | Therapeutic RPE ® PR 4 Mean ± SD (n) | | |
|---|---|---|---|---|---|---|
| Test (Method) | Ctrl | CS2 | CS5 | Ctrl | CS2 | CS5 |
| % Viability (Cell Counter) | 87 ± 5 (n = 4) | 89 ± 5 (n = 4) | 90 ± 4 (n = 4) | 84 (n = 2) | 84 (n = 2) | 91 (n = 2) |
| Purity (FACS): % $CRALBP^+PMEL17^+$ Cells | 98.51 | 99.21 | 98.76 | 99.27 | 99.28 | 98.97 |
| Potency: | | | | | | |
| Transepithelial Electrical Resistance (TEER) | NA | 233 | 385 | 881 | 846 | 701 |
| Polarized PEDF Secretion (Apical to Basal Ratio) | NA | 5.6 | 11.5 | 8.3 | 7.4 | 6.1 |
| Polarized VEGF Secretion (Basal to Apical Ratio) | NA | 2.0 | 2.6 | 3.1 | 2.8 | 2.5 |

Example 4

Stability assays were performed on RTA RPE cell therapy compositions. Cells produced according to the methods in Example 1 were suspended in Media 1 containing 2% DMSO (CS2) or Media 2 containing 5% DMSO (CS5) for up to 3 hours prior to cryopreservation. Therapeutic RPE cells that were cryopreserved after 3 hours incubation in CS2 and CS5 showed similar post thaw viability, vitality and yield as those cells incubated for less than one hour prior to cryopreservation. The stability results are presented in Table 2.

TABLE 2

Stability of Therapeutic RPE Cells Post Thaw (Incubation in Media 1 (CS2) and Media 2 (CS5) Prior to Cryopreservation)

| Incubation Time (hrs) at 2-8° C. prior to | % Viability Post Thaw | | % Yield Post Thaw | | % Vitality 24 Hrs Post Thaw | | Fold Expansion at Day 14 of Culture | |
|---|---|---|---|---|---|---|---|---|
| preservation | CS2 | CS5 | CS2 | CS5 | CS2 | CS5 | CS2 | CS5 |
| 0 | 67 | 70 | 73 | 70 | 94 | 92 | 4.2 | 4.8 |
| 0.5 | 67 | 67 | 65 | 72 | 108 | 100 | 4.3 | 4.5 |
| 1 | 70 | 66 | 77 | 71 | 92 | 76 | 4.8 | 5.4 |
| 2 | 70 | 67 | 92 | 82 | 89 | 112 | 4.9 | 4.5 |
| 3 | 62 | 65 | 64 | 59 | 91 | 112 | 4.3 | 4.5 |

In addition, cells incubated in CS2 or CS5 for 3 hours prior to cryopreservation demonstrated the ability to generate barrier function (tight junctions between RPE cells), measured by the ability to generate Trans Epithelial Electrical Resistance (TEER) above 100Ω and secrete VEGF and PEDF in a polarized manner, as shown in Table 3. (See also FIG. 15).

TABLE 3

TEER and Polarized Secretion of PEDF and VEGF of Therapeutic RPE ® Cells in Media 1 (CS2) and Media 2 (CS5) Post Thaw (Incubation in Media Prior to Cryopreservation)

| | | | Polarized Secretion of PEDF and VEGF | | | |
|---|---|---|---|---|---|---|
| Incubation Time (hrs) | Barrier Function TEER (Ω) | | PEDF Upper to Lower Ratio | | VEGF Lower to Upper Ratio | |
| at 2-8° C. | CS2 | CS5 | CS2 | CS5 | CS2 | CS5 |
| 0 | 188 | 392 | 7.1 | 7.6 | 1.4 | 1.8 |
| 0.5 | 211 | 318 | 5.5 | 6.2 | 1.4 | 1.9 |
| 1 | 253 | 347 | 9.4 | 9.4 | 1.5 | 1.2 |
| 2 | 107 | 241 | 5.1 | 3.5 | 1.2 | 2.7 |
| 3 | 402 | 715 | 5.1 | 5.7 | 1.7 | 1.6 |

Post thawing stability was assessed for RPE cell therapy compositions described above. RPE cell compositions were formulated in Media 1 containing 2% DMSO (CS2) or Media 2 containing 5% DMSO (CS5) and incubated for up to 3 hours prior to cryopreservation. Viability, live cell yield, and potency were determined as described above at time points 0 hours, 1 hour, 2 hours, 3 hours, 5 hours, 6 hours and 24 hours post cryopreservation at between approximately 2 to 8° C.

RPE cells were found to be stable in Media 1 containing 2% DMSO (CS2) or Media 2 containing 5% DMSO (CS5) for at least about 3 hours prior to cryopreservation and at least about 1 hour post cryopreservation or at least about 2 hours prior to cryopreservation and at least about 5 hours post cryopreservation.

Example 5

The safety of three cryopreservation solutions for use with ready to administer (RTA) RPE cell therapy composition formulations was assessed following sub-retinal injection into Balb/c mice.

A total of 36 Balb/c mice were utilized and divided into four (4) groups of nine (9) in each group (n=3 for each of the termination time points; 1, 3 and 10 days post administration). These groups contained one vehicle (BSS PLUS, Alcon Laboratories) control group and three treated groups that received the Test Items (CS5, CS2 and CS2 diluted 1:1 v/v with BSS PLUS). All animals were administered with the various treatments via sub-retinal injection into the left eye. The procedure was performed under anesthesia using ketamine/Medetomidine at 75 mg/kg, which was given IP two minutes before injection.

During the study, morbidity and mortality, body weight, and general clinical observation as well external and internal eye examinations were performed. Eye evaluation was performed by veterinary ophthalmologist once during acclimation (baseline measurement prior to dosing) and on each termination day thereafter. The eye evaluation included: examination of the anterior segment and lens using slit lamp biomicroscopy and examination of the fundus using indirect ophthalmoscopy. The animals were sacrificed on days 1, 3 and 10 post dosing and histopathology examination was performed on the injected eyes.

Clinical, ophthalmologic and histopathological examinations, carried out by a veterinary ophthalmologist and a board of certified veterinary pathologists, demonstrated no major treatment-related or toxicologically significant effects, following sub-retinal administration of RTA RPE formulations in a 10-day follow-up. Histopathological evaluations of inflammation were based on the presence of neutrophils, lymphocytes, macrophages, and mast cells according to the following criteria: no inflammation as indicated by the absence of inflammatory cells, mild inflammation as indicated by up to 10 cells per ×10 magnification field, moderate inflammation as indicated by between about 10 to 20 cells per ×10 magnification field and, strong inflammation as indicated by greater than 20 cells per ×10 magnification field.

Figure 2:
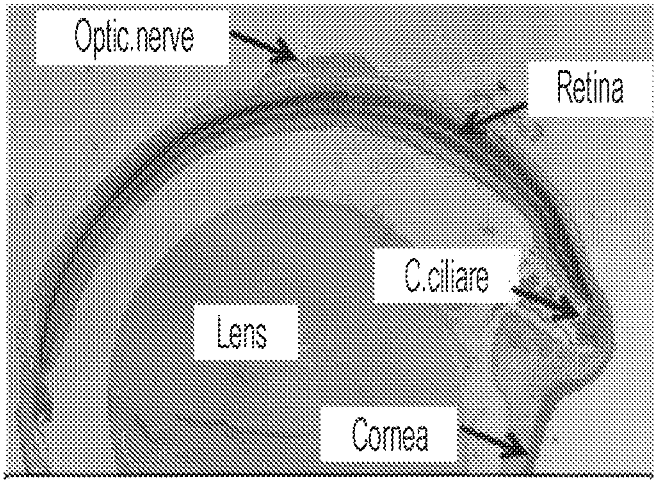
FIG. 2 is a histological image of the eye of a naive animal (untreated animal) showing no pathology (H&E stained at ×4 magnification field).
Figure 3:
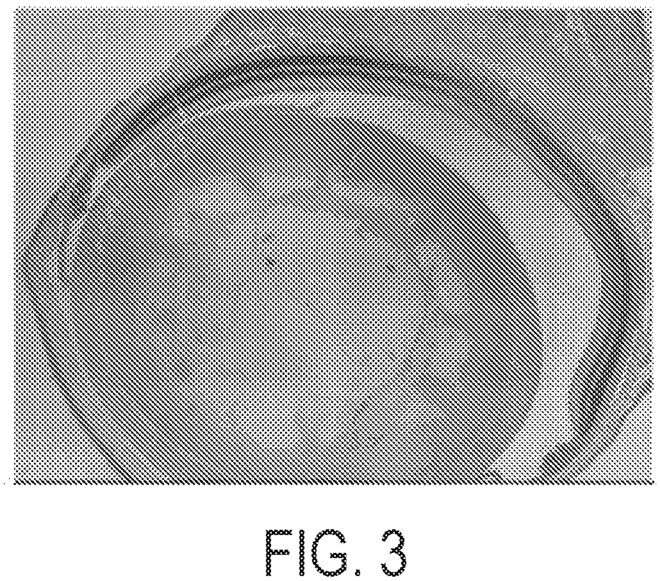
FIG. 3 is a histological image of the right eye (non-treated/control eye) of an animal in the control group showing no pathological changes. (H&E stained at ×4 magnification field).

Histopathological evaluation of the native eye of an untreated animal and the nontreated right eyes of animals in the control groups revealed no pathological changes at all, as shown in FIG. 2 and FIG. 3.

Figure 4A:
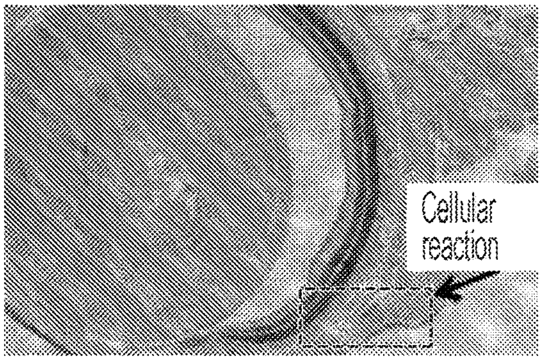
FIG. 4A is a histological image of the left eye (treated eye) taken from an animal treated with BSS Plus and sacrificed on day 1 of the study, showing mild inflammation with mild infiltration of the sclera. (H&E stained at ×4 magnification field).
Figure 4B:
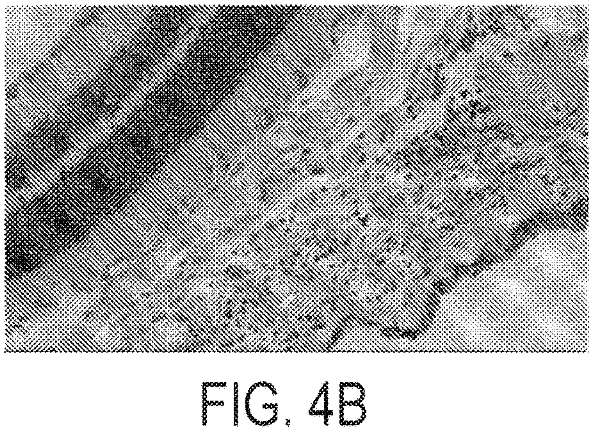
FIG. 4B is a histological image of the left eye (treated eye) taken from an animal treated with BSS Plus and sacrificed on day 1 of the study, showing mild inflammation and a few lose macrophages and lymphocytes. (H&E stained at ×20 magnification field).
Figure 5A:
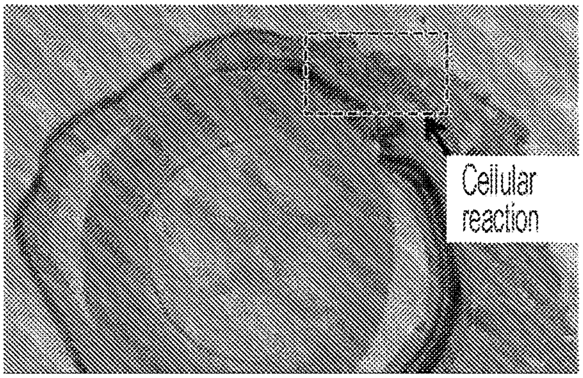
FIG. 5A is a histological image of the left eye (treated eye) taken from an animal treated with CS5 and sacrificed on day 1 of the study, showing moderate inflammation and infiltration of the sclera. (H&E stained at ×4 magnification field).
Figure 5B:
FIG. 5B is a histological image of the left eye (treated eye) taken from an animal treated with CS5 and sacrificed on day 1 of the study, showing moderate inflammation with some macrophages and few neutrophils. (H&E stained at ×20 magnification field).
Figure 6A:
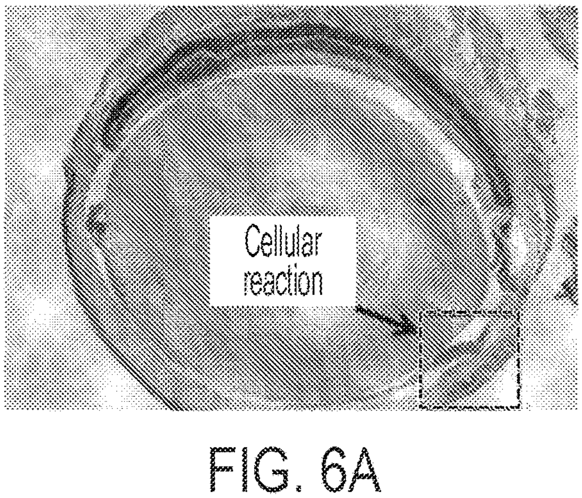
FIG. 6A is a histological image of the left eye (treated eye) taken from an animal treated with CS2 and sacrificed on day 1 of the study, showing moderate inflammation with macrophages and neutrophils in the cornea. (H&E stained at ×4 magnification field).
Figure 6B:
FIG. 6B is a histological image of the left eye (treated eye) taken from an animal treated with CS2 and sacrificed on day 1 of the study, showing moderate inflammation with macrophages and neutrophils. (H&E stained at ×20 magnification field).

Histopathological evaluation of the treated eyes (left eyes) revealed that on termination Day 1, only the animals in the group treated with BSS PLUS:CS2 (1:1 v/v) showed signs of strong inflammation. All other animals treated with either BSS PLUS, CS5 or CS2 showed either mild to moderate inflammation. Images of histopathological slides of the treated eye taken from an animal treated with BSS Plus and sacrificed on day 1 of the study are shown in FIG. 4A and FIG. 4B. These slides show mild inflammation with mild infiltration of the sclera and a few lose macrophages and lymphocytes. (H&E stained at ×4 and ×20 magnification field, respectively). FIG. 5A and FIG. 5B show images of histopathological slides of the treated eye taken from an animal treated with CS5 and sacrificed on day 1. These slides show moderate inflammation with infiltration of the sclera, some macrophages and few neutrophils. (H&E stained at ×4 and ×20 magnification field, respectively). Images of histopathological slides of the treated eye taken from an animal treated with CS2 and sacrificed on day 1 of the study are shown in FIG. 6A and FIG. 6B. These slides show moderate inflammation with macrophages and neutrophils in the cornea. (H&E stained at ×4 and ×20 magnification field, respectively).

Figure 7A:
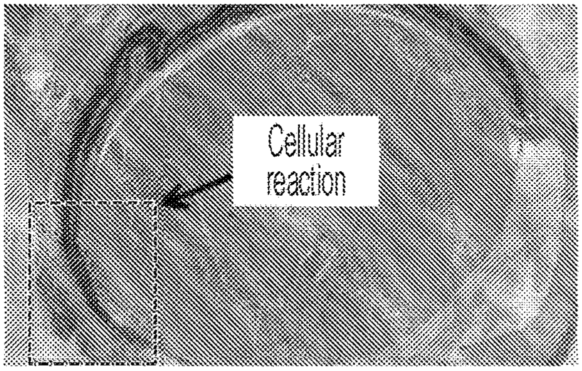
FIG. 7A is a histological image of the left eye (treated eye) taken from an animal treated with BSS PLUS:CS2 and sacrificed on day 1 of the study, showing strong inflammation with moderate infiltration of the sclera. (H&E stained at ×4 magnification field).

Although most animals treated with either CS2 or BSS PLUS:CS2 displayed minimal fibrin deposition in the anterior chamber at termination Day 1, these acute changes demonstrate a short-term reaction. FIG. 7A shows an image of a histopathological slide of the treated eye taken from an animal treated with BSS PLUS:CS2 and sacrificed on day 1 of the study, showing strong inflammation with moderate infiltration of the sclera. (H&E stained at ×4 magnification field).

Figure 7B:
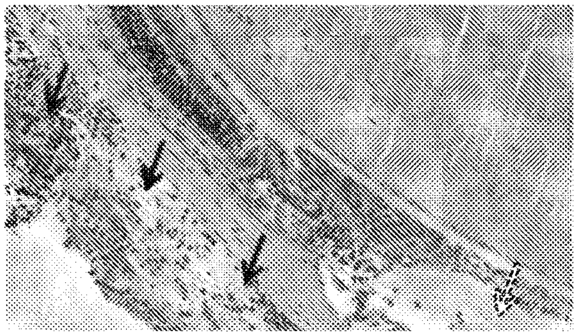
FIG. 7B is a histological image of the left eye (treated eye) taken from an animal treated with BSS PLUS:CS2 and sacrificed on day 1 of the study, showing strong inflammation with fibrin shown at the lower right corner next to the lymphocytes in the sclera. (H&E stained at ×20 magnification field).

FIG. 7B shows fibrin deposition at the lower right corner next to the lymphocytes in the sclera. (H&E stained at ×20 magnification field).

On termination Day 3, all animals treated with either CS5 or CS2 showed a focal scleral granulomatous reaction (mild to moderate inflammation) characterized by macrophages and dividing fibroblasts. Macrophages were also observed in animals treated with BSS PLUS, however, they showed a different pattern and concentration of cells with no fibroblast activation and were not related to the injected material. These results indicate a typical pattern of early stage reaction to foreign body in general. Consequently, on termination Day 10, all of the animals treated with either BSS PLUS, CS5, or CS2 showed no inflammation or mild inflammation and no fibrin deposition. In addition, only one animal treated with BSS PLUS:CS2 displayed moderate inflammation, while all other animals displayed mild inflammation.

Figure 8A:
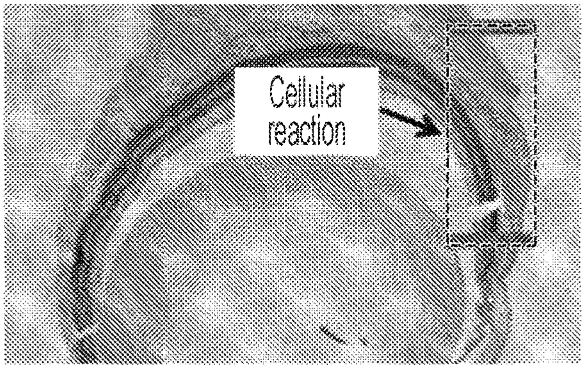
FIG. 8A is a histological image of the left eye (treated eye) taken from an animal treated with BSS PLUS and sacrificed on day 3 of the study, showing moderate inflammation with moderate infiltration of the sclera. (H&E stained at ×4 magnification field).
Figure 8B:
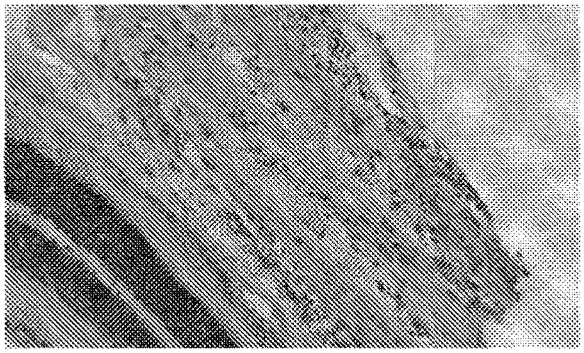
FIG. 8B is a histological image of the left eye (treated eye) taken from an animal treated with BSS PLUS and sacrificed on day 3 of the study, showing moderate inflammation with several macrophages. (H&E stained at ×20 magnification field).
Figure 9A:
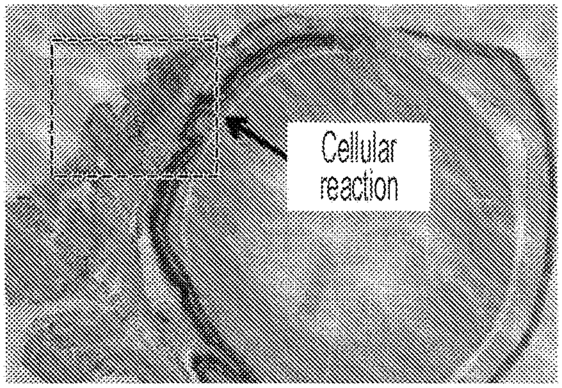
FIG. 9A is a histological image of the left eye (treated eye) taken from an animal treated with CS5 and sacrificed on day 3 of the study, showing strong inflammation with a focal granulation reaction. (H&E stained at ×4 magnification field).
Figure 9B:
FIG. 9B is a histological image of the left eye (treated eye) taken from an animal treated with CS5 and sacrificed on day 3 of the study, showing strong inflammation with several macrophages and fibroblasts, demonstrating an early stage, transitory foreign body reaction. (H&E stained at ×20 magnification field).
Figure 10A:
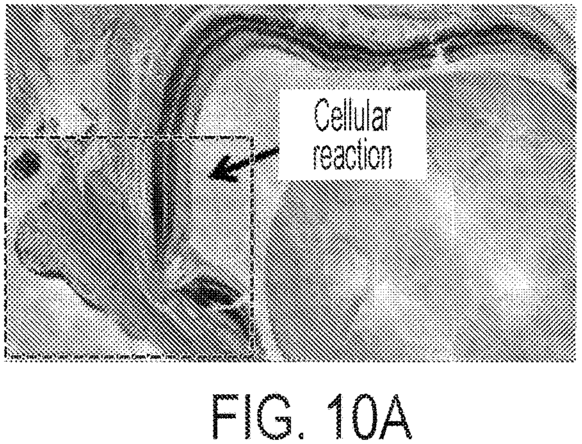
FIG. 10A is a histological image of the left eye (treated eye) taken from an animal treated with CS2 and sacrificed on day 3 of the study, showing strong inflammation with a focal granulation reaction. (H&E stained at ×4 magnification field).
Figure 10B:
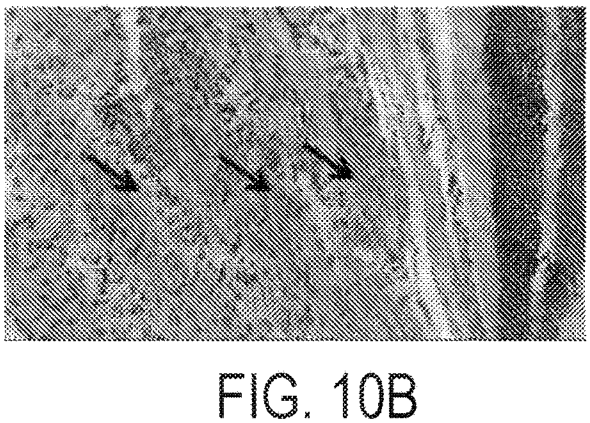
FIG. 10B is a histological image of the left eye (treated eye) taken from an animal treated with CS2 and sacrificed on day 3 of the study, showing strong inflammation with several macrophages and fibroblasts, demonstrating an early stage, transitory foreign body reaction. (H&E stained at ×20 magnification field).
Figure 11A:
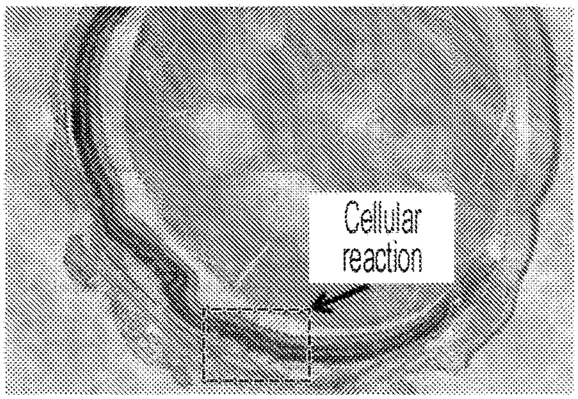
FIG. 11A is a histological image of the left eye (treated eye) taken from an animal treated with BSS PLUS:CS2 and sacrificed on day 3 of the study, showing mild inflammation with mild edema. (H&E stained at ×4 magnification field).
Figure 11B:
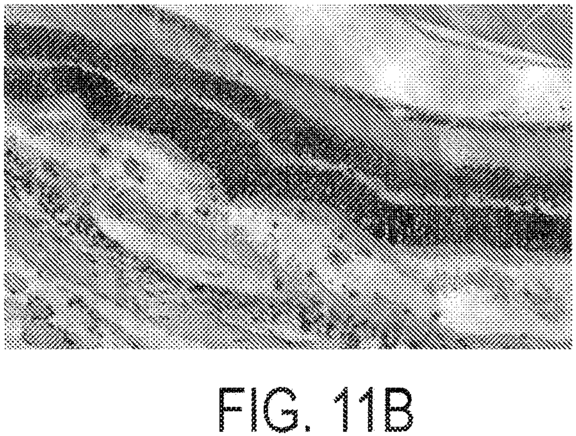
FIG. 11B is a histological image of the left eye (treated eye) taken from an animal treated with BSS PLUS:CS2 and sacrificed on day 3 of the study, showing mild inflammation and few macrophages. (H&E stained at ×20 magnification field).
Figure 12A:
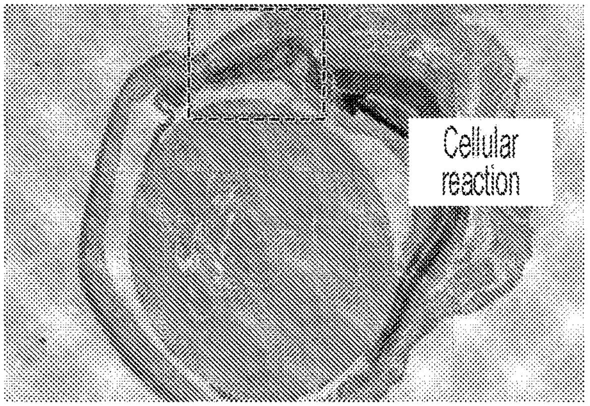
FIG. 12A is a histological image of the left eye (treated eye) taken from an animal treated with BSS PLUS and sacrificed on day 10 of the study, showing mild inflammation with few macrophages. (H&E stained at ×4 magnification field).
Figure 12B:
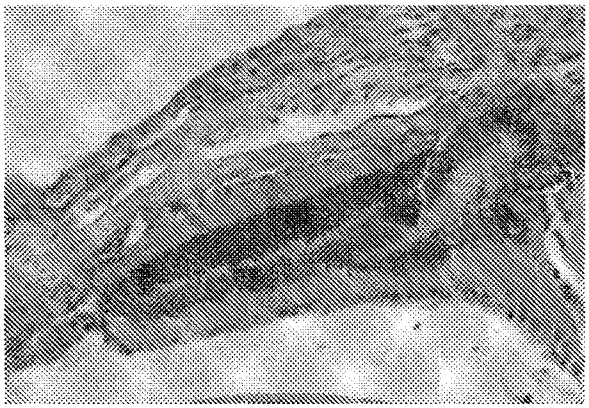
FIG. 12B is a histological image of the left eye (treated eye) taken from an animal treated with BSS PLUS and sacrificed on day 10 of the study, showing mild inflammation with few macrophages. (H&E stained at ×20 magnification field).
Figure 13A:
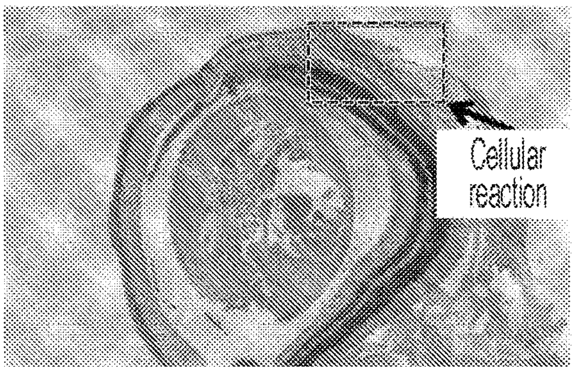
FIG. 13A is a histological image of the left eye (treated eye) taken from an animal treated with CS5 and sacrificed on day 10 of the study, showing mild inflammation with few macrophages. (H&E stained at ×4 magnification field).
Figure 13B:
FIG. 13B is a histological image of the left eye (treated eye) taken from an animal treated with CS5 and sacrificed on day 10 of the study, showing mild inflammation with few macrophages. (H&E stained at ×20 magnification field).
Figure 14A:
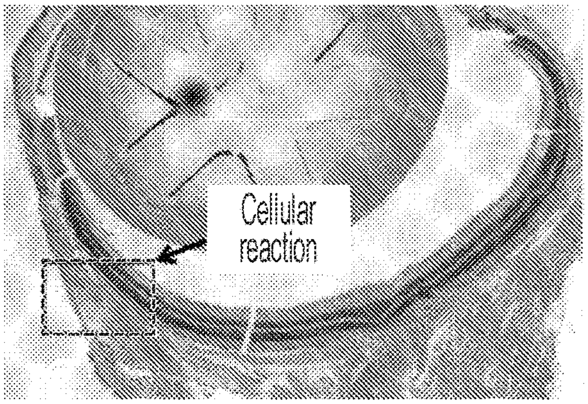
FIG. 14A is a histological image of the left eye (treated eye) taken from an animal treated with CS2 and sacrificed on day 10 of the study, showing mild inflammation with few macrophages. (H&E stained at ×4 magnification field).
Figure 14B:
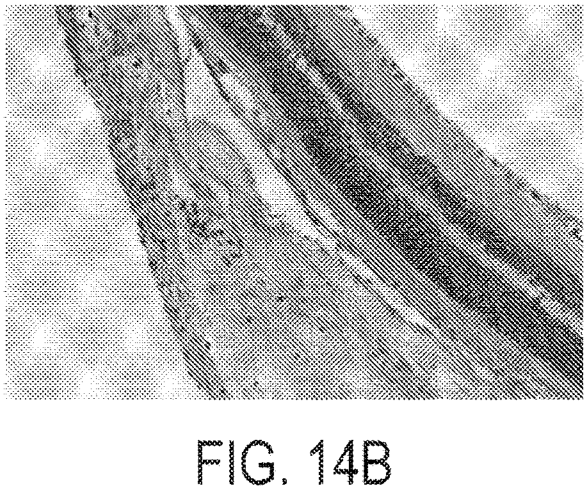
FIG. 14B is a histological image of the left eye (treated eye) taken from an animal treated with CS2 and sacrificed on day 10 of the study, showing mild inflammation with few macrophages. (H&E stained at ×20 magnification field).

Histopathological images demonstrating moderate inflammation with moderate infiltration of the sclera and several macrophages in an animal treated with BSS PLUS and sacrificed on day 3 of the study are shown in FIG. 8A and FIG. 8B. FIG. 9A and FIG. 9B show histopathological images of strong inflammation with a focal granulation reaction and several macrophages and fibroblasts, which illustrates an early stage, transitory foreign body reaction, in an animal treated with CS5 and sacrificed on day 3 of the study. FIG. 10A and FIG. 10B are histopathological images from an animal treated with CS2 and sacrificed on day 3 of the study, showing strong inflammation with several macrophages and fibroblasts, also demonstrating an early stage, transitory foreign body reaction. Histopathological images from an animal treated with BSS PLUS:CS2 and sacrificed on day 3 of the study, with mild inflammation and mild edema are shown in FIG. 11A and FIG. 11B. FIG. 12A and FIG. 12B show histopathological images from an animal treated with BSS PLUS and sacrificed on day 10 of the study, illustrating mild inflammation with few macrophages. FIG. 13A and FIG. 13B show histopathological images from an animal treated with CS5 and sacrificed on day 10 of the study, illustrating mild inflammation with few macrophages. FIG. 14A and FIG. 14B show histopathological images from an animal treated with CS2 and sacrificed on day 10 of the study, illustrating mild inflammation with few macrophages.

The histopathological evaluation results demonstrate that that there were no major treatment-related and/or toxicologically significant effects following the sub-retinal administration of BSS PLUS, CS5, CS2, or BSS PLUS:CS2 as compared to the control after 10 days follow-up. Histopathological evaluation of the treated eyes revealed a typical early stage reaction to a foreign body on termination Day 3 in groups treated with BSS Plus, CS5 and CS2. However, this reaction was transient and subsided by Day 10 leaving a very minor macrophage infiltration in the injected site. Necrosis was not present in any animals' retina or elsewhere.

Example 6

RTA RPE cell therapy compositions were formulated using enzymatic enrichment (isolation/harvest) of pigmented cells and enzyme neutralizing solutions comprising NUTS(−)+Human Serum Albumin (HSA) and NUTS(−) (without Human Serum (HS)) and were analyzed for stability before and after the addition of cryomedium.

Cells were seeded and expanded in T25, T75 and T175 flasks up to passage 4. Upon reaching a polygonality of greater than about 90%, cells were incubated in TrypLE Select (1×) for up to about 50 minutes at 37° C./5% $CO_2$. Cells were pooled and placed on ice. Flasks were washed once with equal volume of PBS (−) and the wash was added to the cell pool. The PBS (−) wash was replaced with NUTS (−) for improved enzyme-neutralizing and reduced cell stress.

The cell pool was then sampled (20 µl in 180 µl PBS (−)) and counted using a cell counter such as the NC-200 cell counter, for example. The cell pool was then aliquoted into the various quenching solutions for groups (G1, G2 and G3). Cells from each group were then counted, filtered and aliquoted for cell composition stability analysis at 4° C.

The enzyme neutralizing solution types that were analyzed included:

Group 1 (G1)—20% Human Serum (HS)/DMEM (HS positive control group)

Group 2 (G2)—Nutristem (−) with Human Serum Albumin (HSA)

Group 3 (G3)—Nutristem (−) (NUTS)

Each of the quenching groups, G1, G2, and G3, were passed through a tandem 500-200-40-micron sequential filtering system. Filtered cell solutions were kept at 4° C. and cell viability was tested at time points 0, 2 and 4 hours post-filtration.

At the end of each time point post-filtration, the cells were counted, centrifuged at about 220 g for about 5 minutes, the supernatant was discarded, and the pellet was resuspended in about 5-10 ml CS5, sampled and counted (20 µl in 180 µl 20% HS/DMEM). Based on count results, cells were diluted in CS5 to obtain a final concentration of $2\times10^6$ cells/ml. Cells were placed at 4° C. for different times (0, 2, 3, or 4 hours) for pre-cryopreservation stability analysis, after which the RPE cell+cryomedia compositions were aliquoted into cryovials. Three cryovials were randomly sampled, the cells were counted, and cryopreserved.

Vials were thawed in a 37° C. water bath for about 2.5 minutes. Cells were immediately sampled for counting (20 µl in 180 µl 20% HS/DMEM) and cell suspensions were diluted by drop-wise addition of warm 20% HS/DMEM culture media. Cells were then washed and placed on ice for additional analysis.

Recovery percentages were calculated based on a targeted final concentration of $2\times10^6$ cells/ml.

Following the sequential filtration, the filtered cell suspensions in the different enzyme neutralizing solutions, were kept at 4° C. and cell viability at 0, 2 and 4 hours post-filtration was evaluated.

TABLE 4

Cell Composition Viability Post-Filtration

| Group | Time pre-centrifuge | Avg. % Viability | SD Viability |
|---|---|---|---|
| G1 | 0 hrs. | 98 | NA |
| G2 | 0 hrs. | 99 | 1.2 |
| (n = 6) | 2 hrs. | 99 | 0.9 |
| | 4 hrs. | 99 | 0.6 |
| G3 | 0 hrs. | 99 | 0.5 |
| (n = 6) | 2 hrs. | 99 | 0.6 |
| | 4 hrs. | 98 | 1.0 |

Figure 16:
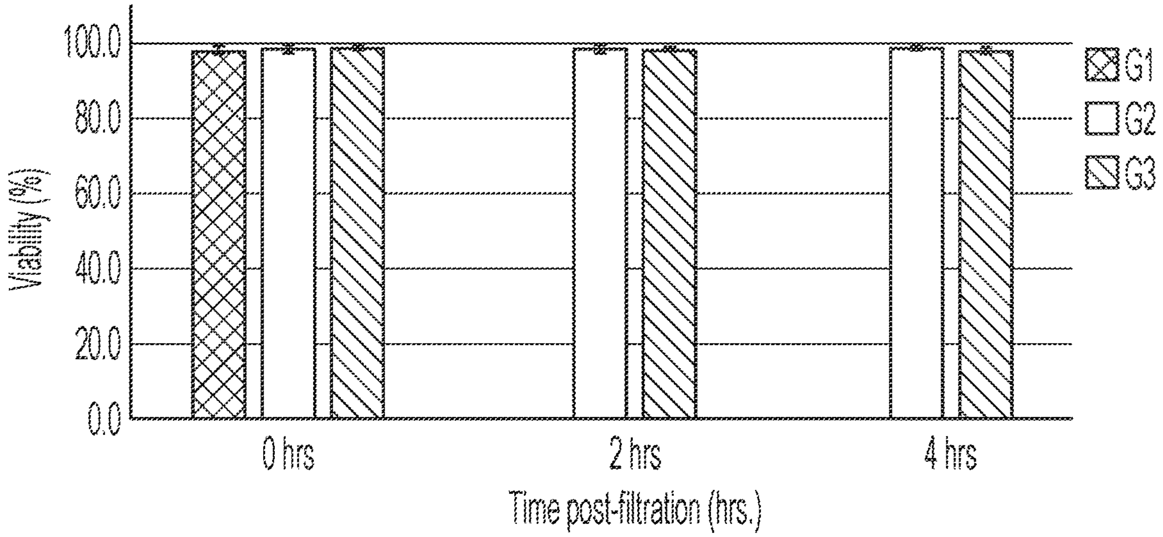
FIG. 16 is a graph of the viability of Group 2 (G2) (NUTS(−)+HSA) and Group 3 (G3) (NUTS(−)) at 4° C. over time post-filtration compared to the control group, G1. Filtered cell compositions were sampled and counted (n=3) at three-time points: 0 hours post-filtration, after 2 hours and after 4 hours.

Viability in all groups, at all time points remained at 98% or 99%, as shown in Table 4. No significant differences were found between the two neutralizing solution formulation groups G2 and G3, at different time points (0, 2 and 4 hours) compared to G1 (control group) time point 0 hours. FIG. 16 shows the viability of G2 (NUTS(−)+HSA) and G3 (NUTS (−)) groups at 4° C. over time post-filtration compared to the control group G1.

Cell recovery and viability were evaluated within cryopreservation solution prior to the freezing process (pre-cryopreservation). Cell therapy compositions (post filtration) were kept at 4° C. for time periods of 0, 2 and 4 hours. Each solution was then centrifuged and resuspended in cryopreservation solution, CS5, to a final concentration of $2\times10^6$ cells/ml. Next, the cells within the cryopreservation solutions (cryopreservation+cell therapy composition, pre-cryopreservation) were kept at 4° C. for 0, 2, 3 and 4 hours before being aliquoted into 1 ml cryovials. Three vials from each group were sampled and counted to evaluate viability and recovery percentages before vials were cryopreserved.

Cell viability and recovery, before the freezing process, of cell therapy compositions at incubation time 0 hours followed by incubation in cryomedia for 0, 2, 3, and 4 hours are summarized together in Table 4A. Tables 4B and 4C include cell compositions incubated for 0, 2, 4 hours followed by incubation for 0, 2, 3, 4 hours in cryopreservation solution (cells+CM). The control group (G1) was evaluated only for time point 0 hours for cell compositions and 0 hours for cells+CM, pre-cryopreservation.

TABLE 5A

Pre-cryopreservation viability and recovery of cell therapy compositions at 0 hours incubation in neutralizing solution followed by incubation for 0, 2, 3, and 4 hours in cryomedia (Cells + CM).

| Cells + CM | Cells at 0 hours incubation | | | | |
|---|---|---|---|---|---|
| pre-cryo time | Group | Avg. % Viability | SD | Avg. % Recovery | SD |
| 0 hrs. | G1 (n = 3) | 98 | 0.9 | 86 | 8.1 |
| | G2 (n = 6) | 98 | 0.8 | 87 | 12.5 |
| | G3 (n = 6) | 98 | 0.9 | 84 | 5.3 |
| 2 hrs. | G2 (n = 6) | 98 | 1.0 | 86 | 7.9 |
| | G3 (n = 6) | 97 | 1.3 | 86 | 12.0 |
| 3 hrs. | G2 (n = 6) | 98 | 0.6 | 86 | 9.5 |
| | G3 (n = 6) | 97 | 3.4 | 92 | 10.4 |
| 4 hrs. | G2 (n = 6) | 98 | 0.9 | 90 | 8.7 |
| | G3 (n = 6) | 95 | 3.3 | 92 | 7.8 |

Figure 17A:
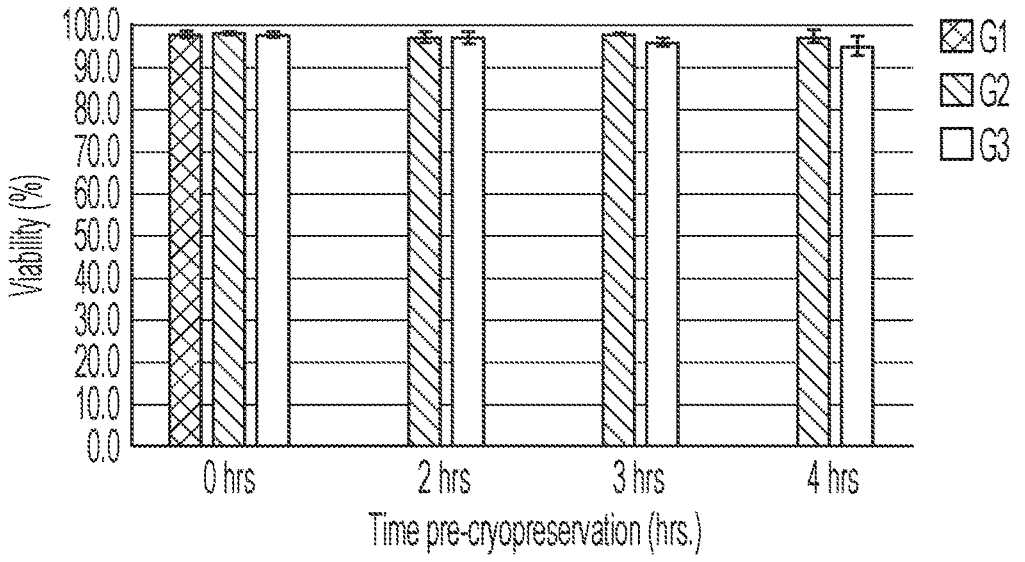
FIG. 17A is a graph showing the effect of 0 hours incubation of the therapeutic cell compositions post-filtration followed by 0, 2, 3, and 4 hours incubation of the therapeutic cell compositions in cryopreservation medium on cell viability, prior to cryopreservation.
Figure 17B:
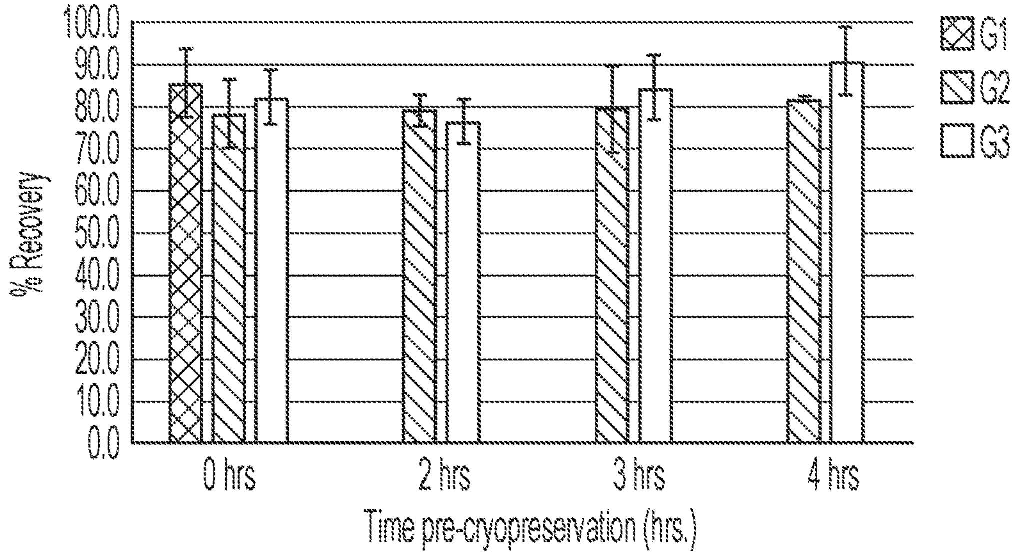
FIG. 17B is a graph showing the effect of 0 hours incubation of the therapeutic cell compositions post-filtration followed by 0, 2, 3, and 4 hours incubation of the therapeutic cell compositions in cryopreservation medium on cell recovery, prior to cryopreservation.
Figure 18A:
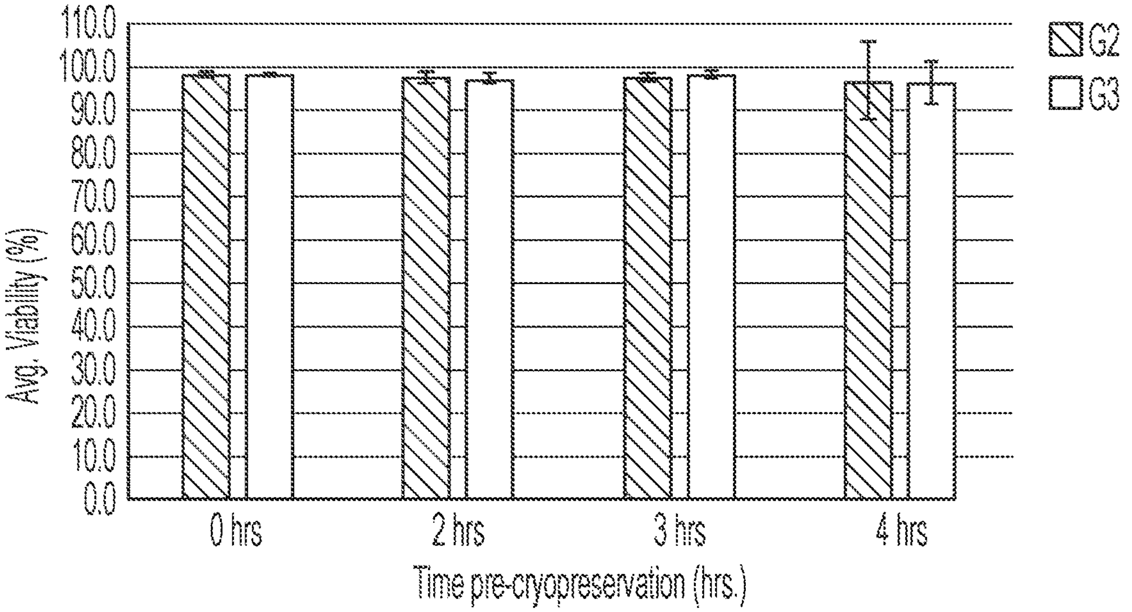
FIG. 18A is a graph showing the effect of 2 hours incubation of the therapeutic cell compositions post-filtration followed by 0, 2, 3, and 4 hours incubation of the therapeutic cell compositions in cryopreservation medium on cell viability, prior to cryopreservation.
Figure 18B:
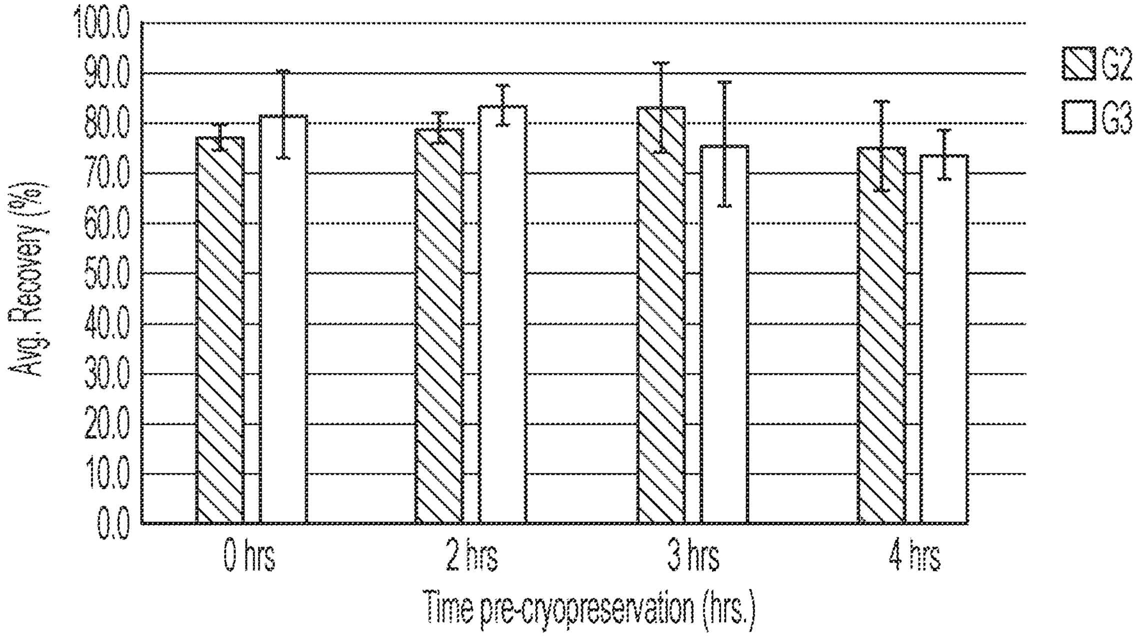
FIG. 18B is a graph showing the effect of 2 hours incubation of the therapeutic cell compositions post-filtration followed by 0, 2, 3, and 4 hours incubation of the therapeutic cell compositions in cryopreservation medium on cell recovery, prior to cryopreservation.
Figure 19A:
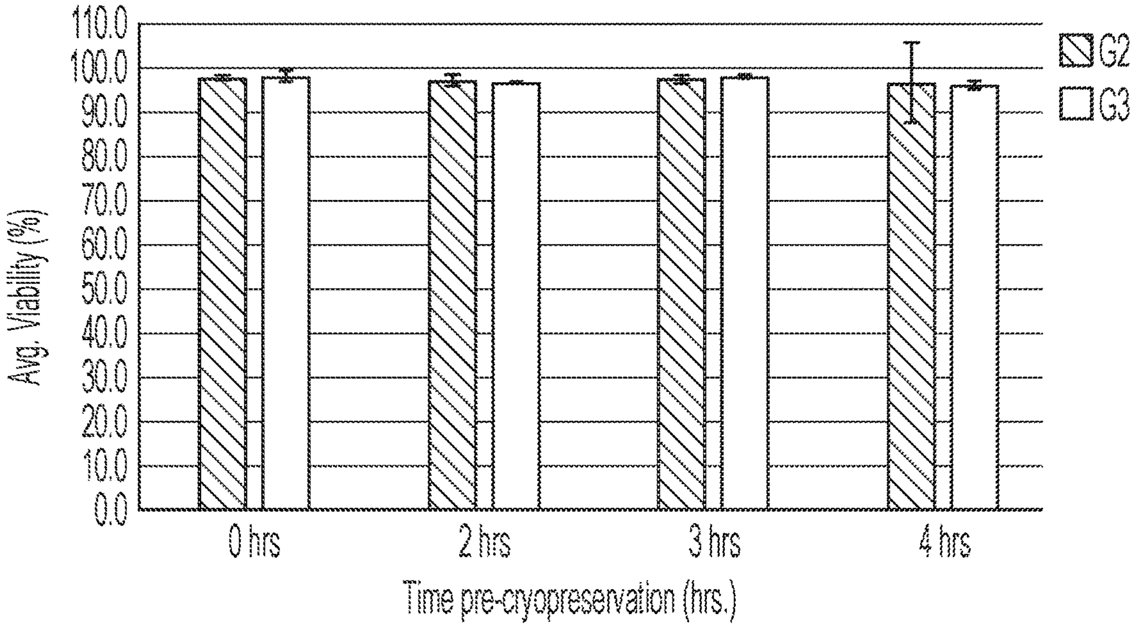
FIG. 19A is a graph showing the effect of 4 hours incubation of the therapeutic cell compositions post-filtration followed by 0, 2, 3, and 4 hours incubation of the therapeutic cell compositions in cryopreservation medium on cell viability, prior to cryopreservation.
Figure 19B:
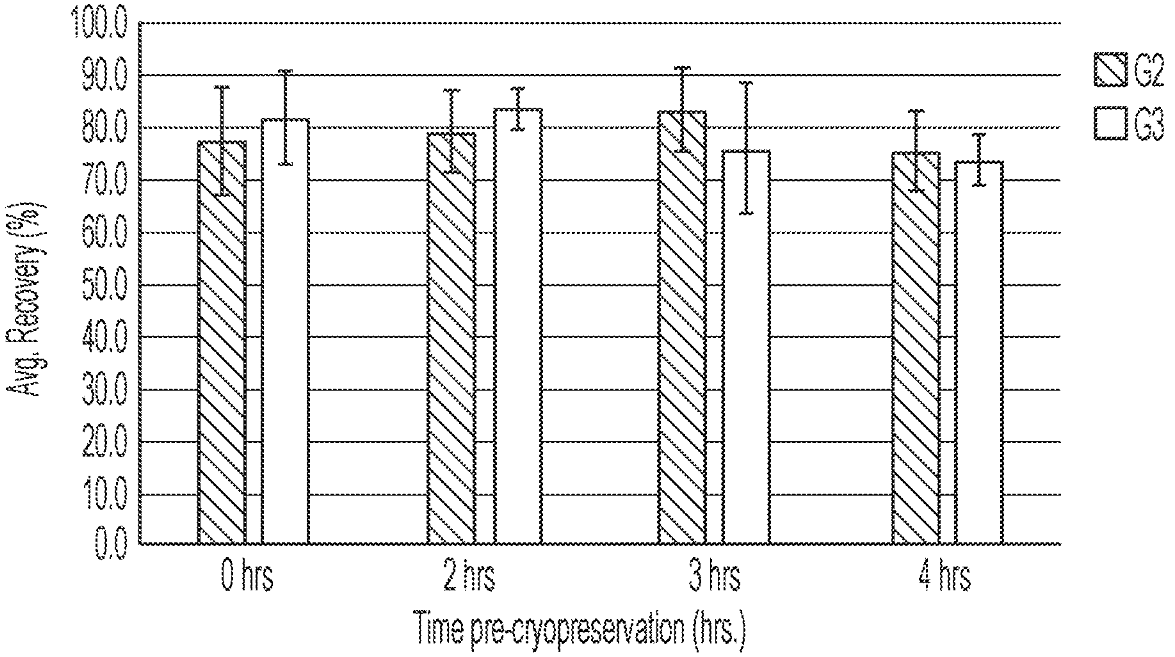
FIG. 19B is a graph showing the effect of 4 hours incubation of the therapeutic cell compositions post-filtration followed by 0, 2, 3, and 4 hours incubation of the therapeutic cell compositions in cryopreservation medium on cell recovery, prior to cryopreservation.

As shown in Table 5A, FIG. 17A, and FIG. 17B, at time point 0 hours therapeutic cell composition incubation followed by 0 hours incubation in cryomedia, pre-cryopreservation, no significant differences in viability and recovery were detected between both neutralizing groups, G2 and G3, compared to the G1 control group. Moreover, 0 hours therapeutic cell composition incubation in neutralizing solution followed by 2, 3, and 4 hours incubation in cryomedium, pre-cryopreservation, did not present a reduction in viability or recovery of the cells in both G2 and G3 groups compared to the G1 control group. Viability remained above 95% over time and no significant differences were observed among the three groups. Furthermore, recovery of all groups remained in the range of 75%-100%.

TABLE 5B

Pre-cryopreservation cell viability and cell recovery after 2 hours therapeutic cell composition incubation followed by 0, 2, 3 and 4 hours incubation in cryomedium, pre-cryopreservation.

| Cells + CM pre-cryo time | Group | Cells at 2 hours incubation Avg. % Viability | SD | Avg. % Recovery | SD |
|---|---|---|---|---|---|
| 0 hrs. | G2 (n = 3) | 98 | 0.5 | 77 | 2.5 |
| | G3 (n = 3) | 98 | 0.3 | 82 | 8.7 |
| 2 hrs. | G2 (n = 3) | 97 | 1.3 | 79 | 3.0 |
| | G3 (n = 3) | 97 | 1.0 | 84 | 3.9 |
| 3 hrs. | G2 (n = 3) | 97 | 0.9 | 83 | 8.8 |
| | G3 (n = 3) | 98 | 1.0 | 76 | 12.5 |
| 4 hrs. | G2 (n = 3) | 97 | 2.0 | 75 | 9.0 |
| | G3 (n = 3) | 96 | 0.7 | 74 | 4.9 |

TABLE 5C

Pre-cryopreservation cell viability and cell recovery after 4 hours therapeutic cell composition incubation followed by 0, 2, 3, 4 hours incubation in cryomedium, pre-cryopreservation.

| Cells + CM pre-cryo time | Group | Cells at 4 hours incubation Avg. % Viability | SD | Avg. % Recovery | SD |
|---|---|---|---|---|---|
| 0 hrs. | G2 (n = 3) | 98 | 0.4 | 86 | 10.4 |
| | G3 (n = 3) | 97 | 1.2 | 92 | 9.5 |
| 2 hrs. | G2 (n = 3) | 96 | 0.2 | 87 | 7.9 |
| | G3 (n = 3) | 98 | 0.2 | 86 | 6.4 |
| 3 hrs. | G2 (n = 3) | 98 | 2.4 | 82 | 8.3 |
| | G3 (n = 3) | 97 | 0.5 | 88 | 7.0 |
| 4 hrs. | G2 (n = 3) | 97 | 0.9 | 85 | 7.8 |
| | G3 (n = 3) | 97 | 1.0 | 92 | 8.1 |

Tables 5B and 5C and FIG. 18A, FIG. 18B, FIG. 19A, and FIG. 19B show that when RPE therapeutic cell compositions are incubated in neutralizing solution for 2 and 4 hours followed by 0-4 hours incubation in cryomedium, pre-cryopreservation, similar cell viability and recovery values for both groups G2 (cell compositions in Nutistem(−) with HSA) and G3 (cell compositions in Nutistem(−) (NUTS)) are seen. This assay demonstrated that there were no significant effects on cell viability or cell recovery given prolonged incubation in either of the neutralizing solutions or cryomedium, prior to cryopreservation.

Example 7

Cells can experience stress during cryopreservation which may lead to poor survival rates post-thawing. Additionally, stress on the cells during harvesting procedures may affect post thawing cell viability and recovery. Accordingly, cell viability and recovery of RTA therapeutic cell compositions were assessed post-thawing. Therapeutic cell compositions that were incubated for 0 hours in different neutralization solutions (G1, G2, and G3, as described above) followed by incubation in cryomedium for 0, 2, 3 and 4 hours pre-cryopreservation were assessed for viability and recovery post-cryopreservation.

Table 6 summarizes the viability and stability results obtained when therapeutic cell compositions were incubated in enzyme neutralizing solutions for 0 hours followed by incubation in cryomedium for 0, 2, 3, and 4 hours (pre-cryopreservation), cryopreserved and then thawed.

TABLE 6

Post thawing viability and recovery of 0 hours cells + neutralizing solution incubation followed by 0, 2, 3, and 4 hours incubation in cryomedium

| Group | Pre-Cryo-preservation time in CS5 | Avg. % Recovery | SD % Recovery | Avg. % Viability | SD % Viability | Group % Recovery | SD % Recovery | Group % Viability | SD % Viability |
|---|---|---|---|---|---|---|---|---|---|
| G1 (n = 4) | 0 hrs. | 92 | 7.9 | 97 | 1.1 | 92 | 7.9 | 97 | 1.1 |
| G3 (n = 4-6) | 0 hrs. | 91 | 8.8 | 98 | 1.0 | 91 | 10.0 | 97 | 1.3 |
| | 2 hrs. | 87 | 12.6 | 96 | 1.3 | | | | |
| | 3 hrs. | 94 | 8.0 | 96 | 0.9 | | | | |
| | 4 hrs. | 95 | 8.8 | 97 | 1.7 | | | | |
| G4 (n = 4-6) | 0 hrs. | 99 | 10.1 | 96 | 0.8 | 98 | 14.7 | 96 | 0.7 |
| | 2 hrs. | 104 | 18.9 | 97 | 0.4 | | | | |
| | 3 hrs. | 99 | 17.1 | 96 | 0.9 | | | | |
| | 4 hrs. | 89 | 6.3 | 96 | 0.7 | | | | |

Analysis of cell viability and recovery, prior to cryo-preservation with different incubation times in cryomedium, revealed that viability was maintained above about 90% in all groups at all time points and recovery was in the range of about 75%-100%.

Figure 20A:
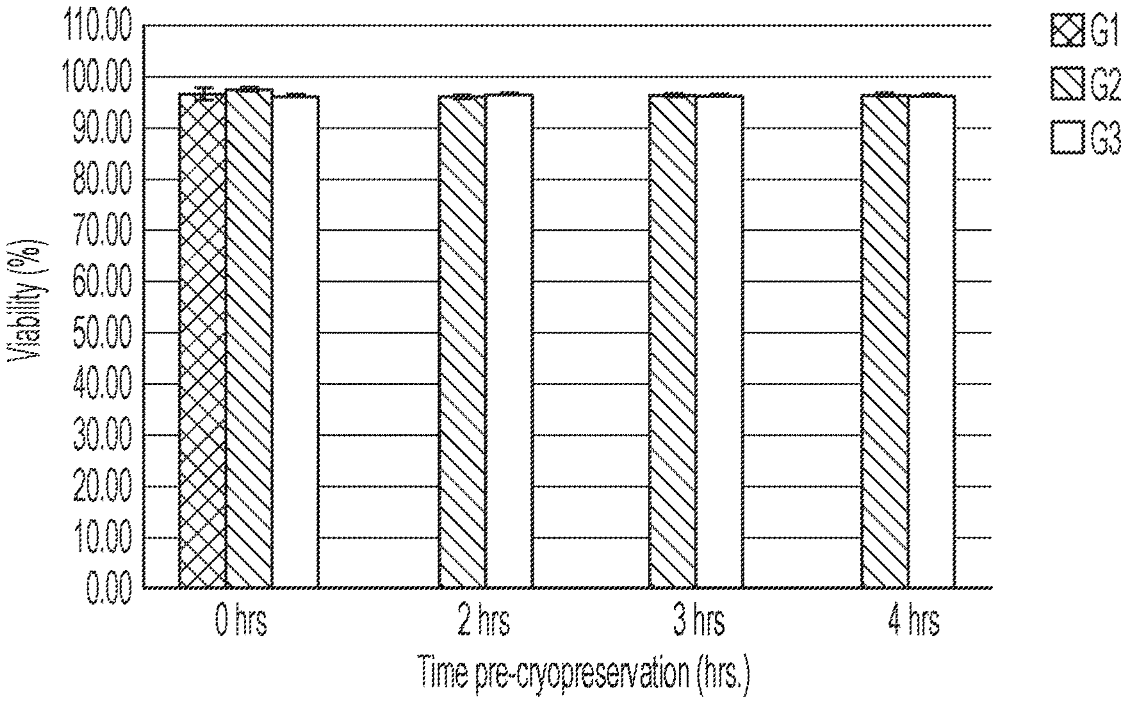
FIG. 20A is a graph showing the effect of prolonged pre-cryopreservation incubation of cell compositions in cryomedium for 0, 2, 3, and 4 on cell viability post-thawing.
Figure 20B:
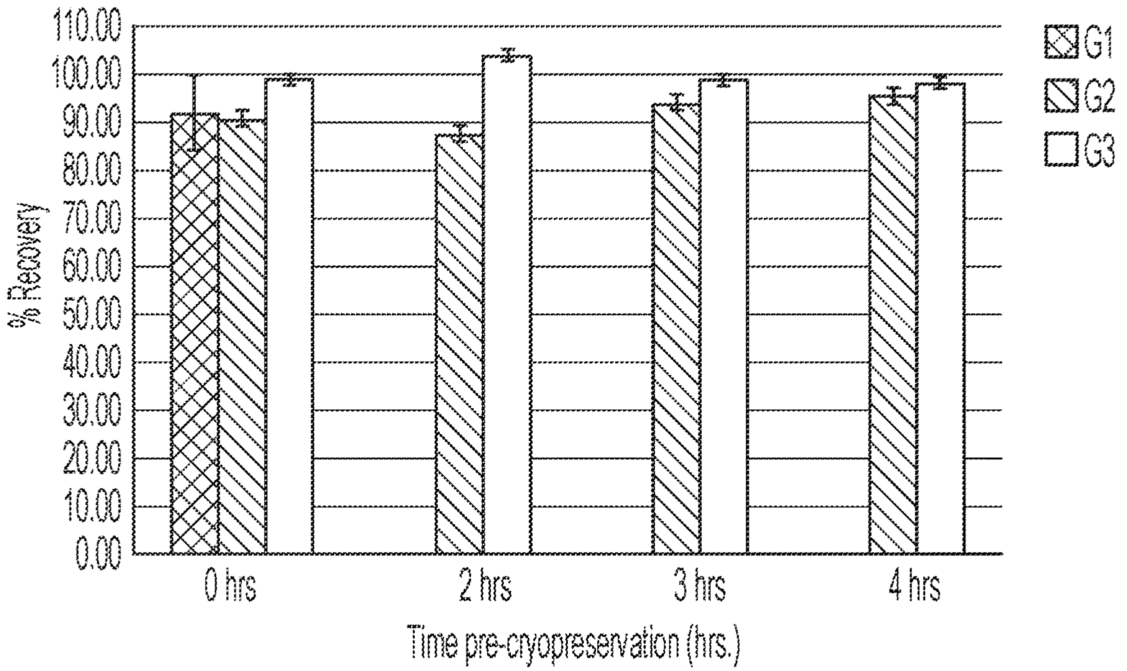
FIG. 20B is a graph showing the effect of prolonged pre-cryopreservation incubation of cell compositions in cryomedium for 0, 2, 3, and 4 on cell recovery post-thawing.
Figure 21A:
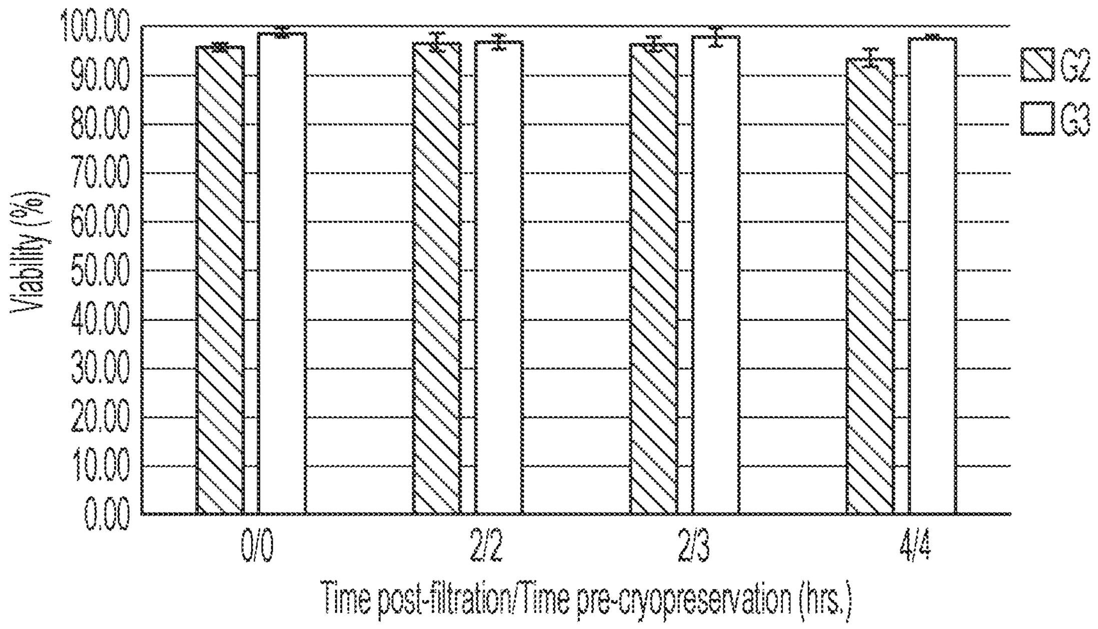
FIG. 21A is a graph showing the effect of therapeutic cell compositions incubated in enzyme neutralizing solution pre-cryopreservation followed by incubation in cryomedium pre-cryopreservation. Cells were then cryopreserved, thawed and analyzed for post-thaw viability.
Figure 21B:
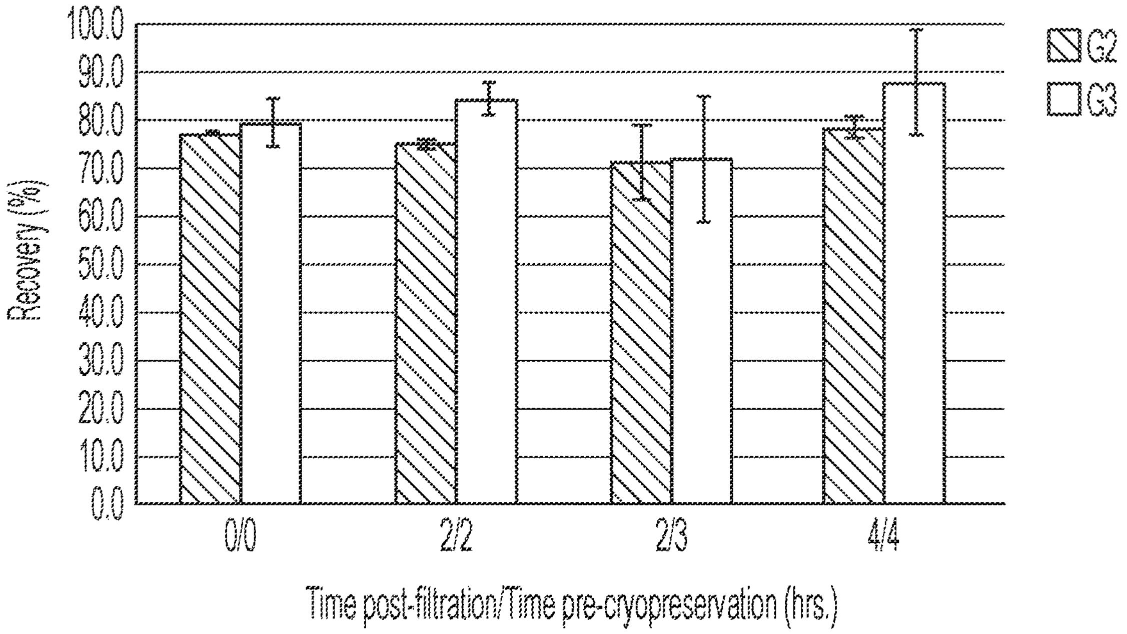
FIG. 21B is a graph showing the effect of therapeutic cell compositions incubated in enzyme neutralizing solution pre-cryopreservation followed by incubation in cryomedium pre-cryopreservation. Cells were then cryopreserved, thawed and analyzed for post-thaw recovery.

As shown in FIG. 20A, there were no significant differences in cell viability among the groups and viability remained above about 95% across the entire pre-cryopreservation time range and was comparable to the viability of G1 control group. Analysis of the recovery results, shown in FIG. 20B, revealed higher recovery values for group G4, which peaked at 2 hours pre-cryopreservation and then slightly decreased after 3 and 4 hours pre-cryopreservation. However, recovery remained in the range of about 80%-100%.

The post thawing results obtained when therapeutic cell compositions were incubated for 0, 2, and 4 hours in neutralization solution followed by incubation for 0, 2, 3, and 4 hours in cryomedium are presented in Table 7. These results demonstrate the relationship of post-thawing viability and recovery on prolonged exposure of the cells to CS5 pre-cryopreservation which, in turn, may be affected by prolonged incubation of the cells in the enzyme neutralizing solution.

TABLE 8

PEDF secretion and expansion ability of cells post harvesting and cryopreservation for RPE cell compositions with enzyme neutralizing solution (cells) and RTA RPE cell compositions (cells + CM) incubation time

| | Group | Time Cells – Cells + CM pre-cryo | LIVE cells day-14 | PEDF Day 14 ng/ml/day | % Recovery |
|---|---|---|---|---|---|
| Assay 1 | G1 | 0-0 | 3.77E+06 | 2171 | 7.54 |
| | G2 | 0-0 | 4.07E+06 | 2452 | 8.14 |
| | | 0-2 | 2.80E+06 | 2407 | 5.60 |
| | | 0-3 | 3.21E+06 | 2255 | 6.42 |
| | | 0-4 | ND | 2032 | ND |
| | G3 | 0-0 | ND | 2364 | ND |
| | | 0-2 | 2.73E+06 | 2181 | 5.46 |
| | | 0-3 | 3.48E+06 | 2739 | 6.96 |
| | | 0-4 | ND | 2310 | ND |
| | Test Production Run | | ND | 2413 | ND |
| Assay 2 | G2 | 0-0 | 3.54E+06 | 2051 | 7.08 |
| | | 2-2 | 2.62E+06 | 2030 | 5.24 |
| | | 2-3 | 2.60E+06 | 2305 | 5.20 |
| | | 4-4 | 3.70E+06 | 2381 | 7.40 |
| | G3 | 0-0 | 3.54E+06 | 2379 | 7.08 |

TABLE 7

Post thawing viability and recovery of cells incubated in enzyme neutralization solution for 0, 2, 4 hours followed by incubation in cryomedia (pre-cryopreservation) for 0, 2, 3, and 4 hours

| Group | Time DS/ DP pre-cryo | Avg. % Viability | SD % Viability | Avg. % Recovery | SD % Recovery | Grp % Recov | SD % Recov | Grp % Viab | SD % Viab |
|---|---|---|---|---|---|---|---|---|---|
| G2 | 0 hrs/0 hrs | 95 | 0.6 | 77 | 0.4 | 75 | 3.3 | 95 | 1.7 |
| (n = 2) | 2 hrs/2 hrs | 96 | 1.6 | 75 | 1.4 | | | | |
| | 2 hrs/3 hrs | 96 | 1.3 | 71 | 7.8 | | | | |
| | 4 hrs/4 hrs | 93 | 1.8 | 79 | 2.1 | | | | |
| G3 | 0 hrs/0 hrs | 98 | 1.1 | 80 | 5.0 | 81 | 7.1 | 97 | 1.3 |
| (n = 2) | 2 hrs/2 hrs | 96 | 1.4 | 85 | 3.5 | | | | |
| | 2 hrs/3 hrs | 98 | 1.8 | 72 | 13.1 | | | | |
| | 4 hrs/4 hrs | 97 | 0.1 | 88 | 11.0 | | | | |

The viability measured for both groups G2 and G3 was robust at above 93%, with no significant differences between groups G2 and G3 across all time points. Recovery of both groups showed no significant differences. Recovery for group G2 was 75%±3.3 and recovery for group G3 was 81%±7.1.

These results demonstrate that the neutralizing solutions (NUT(–) with HSA (group G2) and without HSA (group G3)) did not compromise cell recovery or cell viability. No significant differences were found between the two quenching groups with or without HSA (G2 & G3). The cell viability and cell recovery results for the enzyme neutralizing solutions without HS were comparable to the enzyme neutralizing solutions comprising HS (G1) both pre- and post-cryopreservation.

In addition, the cell harvesting procedure comprising enzyme neutralizing solutions without HS and a filtration step did not compromise the viability of the cells (Table 4). Pre-cryopreservation and post thawing analysis of cell recovery and viability showed no significant differences between the groups G2 and G3 compared to the control group (G1) (Tables 5-7). The greatest percent recovery and viability were found when cells were incubated in the enzyme neutralizing solutions for up to 2 hours followed by incubation in cryomedium for up to 3 hours. However, incubation times of at least 4 hours in either the enzyme neutralizing solution or the cryomedium did not result in a significant decrease in cell viability or cell recovery.

PEDF secretion and cell expansion capability was also measured after the cells were harvested, cryopreserved and thawed. The results are shown in Table 8.

TABLE 8-continued

PEDF secretion and expansion ability of cells post harvesting and cryopreservation for RPE cell compositions with enzyme neutralizing solution (cells) and RTA RPE cell compositions (cells + CM) incubation time

| | Group | Time Cells – Cells + CM pre-cryo | LIVE cells day-14 | PEDF Day 14 ng/ml/day | % Recovery |
|---|---|---|---|---|---|
| | | 2-2 | 2.90E+06 | 2063 | 5.80 |
| | | 2-3 | 3.80E+06 | 2289 | 7.60 |
| | | 4-4 | 3.15E+06 | 2382 | 6.30 |
| | Test Production Run | | 2.35E+06 | 2404 | 4.70 |

ND—No Data

As shown in Table 8, upon thawing, cells retained their functional ability to secrete PEDF and to expand. Results indicated no significant differences among the two enzyme neutralizing solution groups without HS (G2, G3), at all measured time points or between these groups and the enzyme neutralizing solution group with HS (G1).

Example 8

Therapeutic cell compositions were analyzed for stability (% viability and % recovery) post-filtration after incubation at room temperature (RT) and at temperatures between about 2-8° C., as shown in Table 9.

TABLE 9

| Incubation times | | | | | |
|---|---|---|---|---|---|
| | Group 1 | Group 2 | Group 3 | Group 4 | Group 5 |
| Cells | 2 hrs (~4° C.) | 2 hrs (~4° C.) | 2 hrs (~4° C.) | 2 hrs (~4° C.) | 2 hrs (RT) |
| Cells + CM | T = 0 (~4° C.) | 2 hrs (~4° C.) | 4 hrs (~4° C.) | 6 hrs (~4° C.) | 6 hrs (RT) |

Cells were harvested enzymatically (e.g., TrypLE Select). The enzyme was neutralized using Nutristem (−) (NUTS). Following sequential filtration, the filtered cell suspension (Cell Pool) was divided into 2 groups, the 1st group ("Cells 2-8° C.") was kept at about 2-8° C. and the 2nd group ("Cells RT") was kept at RT. The cell viability and cell concentration of the 2 groups were evaluated at Time 0 and after 2 hours incubation.

Figure 22:
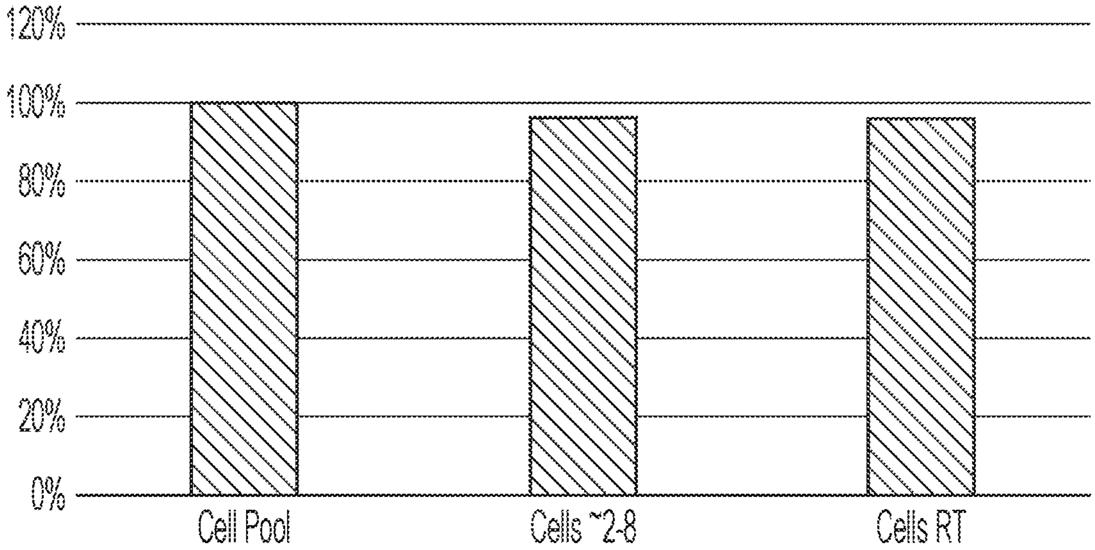
FIG. 22 is a graph showing the percent recovery of therapeutic cells post-filtration and incubation for 2 hours at about 2-8° C. and at RT.

As shown in Table 10, there were no significant differences in cell viability and cell concentration between the groups of cell compositions incubated pre-cryopreservation at about 2-8° C. or RT. Similarly, there were no significant differences in percent recovery between the groups, as shown in FIG. 22.

TABLE 10

| Cell viability and cell concentration after 2 hours incubation | | |
|---|---|---|
| Group | Cell concentration | Viability (n = 2) |
| Cell Pool | $1.30 \times 10^6$ | 98 |
| Cells at 2-8° C. | $1.26 \times 10^6$ | 98 |
| Cells at RT | $1.25 \times 10^6$ | 98 |

After 2 hours incubation, the two groups were centrifuged and resuspended in the cryopreservation solution, CS5, to a final concentration of $2\times10^6$ cells/ml. The "Cells 2-8° C." group was divided into 4 sub-groups (Cells+CM-groups 1-4), which were incubated at 2-8° C. Cells+CM-group 1 was counted at time point 0 hours for cell concentration and cell viability and cryopreserved (n=29 cryovials). Cells+CM-group 2 was counted after 2 hours incubation at 2-8° C., Cells+CM-group 3 was sampled after 4 hours and Cells+CM-group 4 was counted 6 hours after incubation for cell concentration and cell viability. At the various incubation time points, when counting was completed, the Cells+CM-groups 2-4 were cryopreserved by aliquoting 1 ml into each cryovial (n=30, 30 and 29 cryovials respectively). "Cells+CM RT" was sampled for viability and cell concentration at time points 2, 4, and 6 hours. After 6 hours incubation, this group was also cryopreserved (n=22 cryovials).

TABLE 11

| Therapeutic cell composition in cryomedium: cell concentration and cell viability at various time points. | | | | |
|---|---|---|---|---|
| Conditions | Group | Cell concentration | Viability (n = 2) | % Recovery |
| 4° C. | Cells + CM-group 1 (Time 0) | $2.0 \times 10^6$ | 97 | NA |
| | Cells + CM - group 2 (2 hrs) | $2.30 \times 10^6$ | 95 | 115 |
| | Cells + CM - group 3 (4 hrs) | $2.20 \times 10^6$ | 93 | 110 |

TABLE 11-continued

| Therapeutic cell composition in cryomedium: cell concentration and cell viability at various time points. | | | | |
|---|---|---|---|---|
| Conditions | Group | Cell concentration | Viability (n = 2) | % Recovery |
| | Cells + CM - group 4 (6 hrs) | $2.30 \times 10^6$ | 93 | 115 |
| Room Temperature (RT) | Cells + CM RT (Time 0) | $2.0 \times 10^6$ | 94 | NA |
| | Cells + CM RT (2 hrs) | $1.70 \times 10^6$ | 93 | 85 |
| | Cells + CM RT (4 hrs) | $1.78 \times 10^6$ | 91 | 89 |
| | Cells + CM RT (6 hrs) | $1.73 \times 10^6$ | 88 | 86 |

Figure 23A:
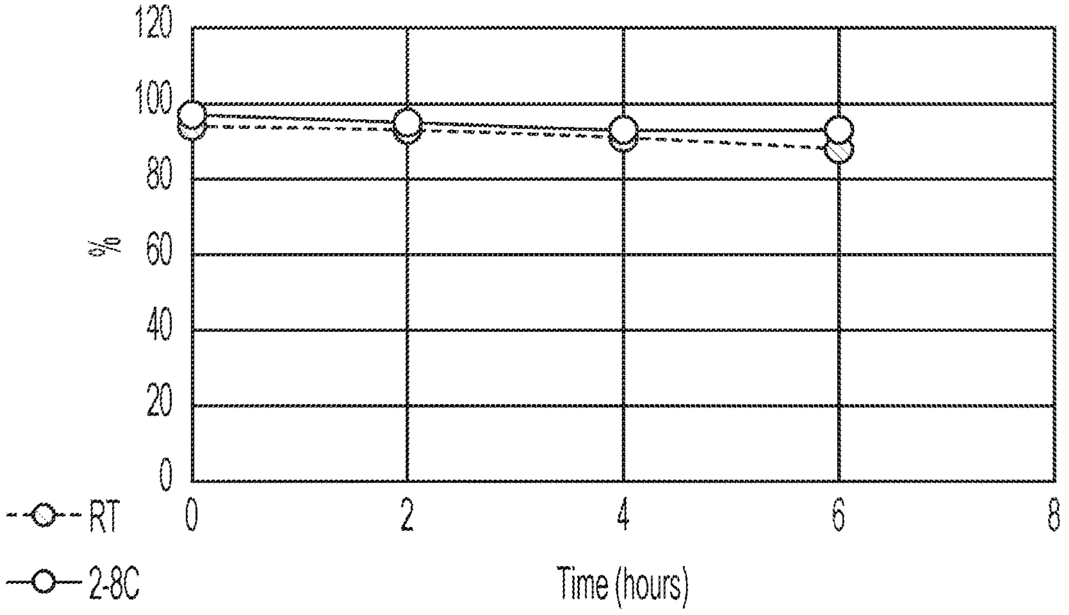
FIG. 23A is a graph showing the viability of therapeutic cell compositions comprising cryomedium under different incubation conditions.
Figure 23B:
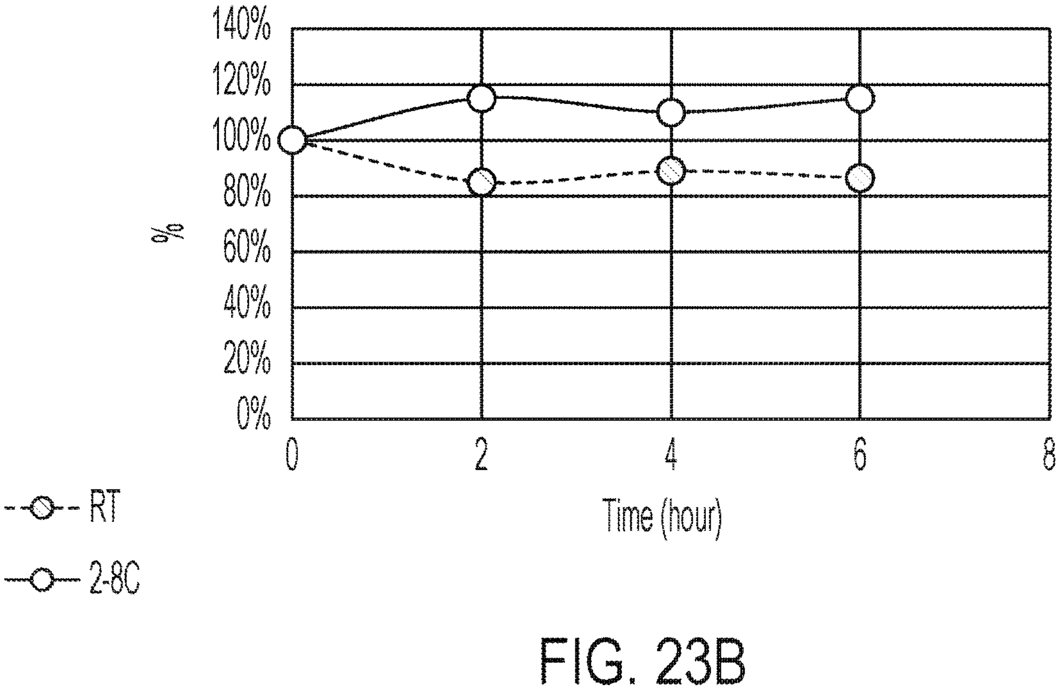
FIG. 23B is a graph showing the viability of therapeutic cell compositions comprising cryomedium under different incubation conditions.

As shown in Table 11 and FIG. 23A and FIG. 23B, there were no significant differences in viability between the cell compositions+cryomedium at RT and cell compositions+cryomedium at about 2-8° C. groups, with a small decrease in cell viability in all groups over time. The results indicate that cell recovery remains stable within all groups over at least 6 hours in both temperature conditions, about 2-8° C. and RT, with a slightly greater recovery of cells incubated at about 2-8° C., prior to the freezing process. The cells that were incubated at RT showed a 15% reduction in recovery at 2 hours, however, recovery and viability remained stable for at least 6 hours.

Example 9

Two cell thawing methods, one comprising a water bath at about 37° C. and the other comprising an automated cell thawing unit, were evaluated based on cell viability, recovery, sterility, potency and identity, as shown in Table 12.

TABLE 12

| Test groups and assay time points for post-thaw analysis. | | | | |
|---|---|---|---|---|
| Cells + CM (RTA) | Dose | Time point (hr.) | | |
| Group No. | (cells/mL) | T = 0 | T = 2 | T = 4 |
| Group 1 | $2 \times 10^6$ | V, R, I, P | V, R, P | V, R, P, S |
| Group 2 | $5 \times 10^6$ | V, R, P | V, R, I, P | V, R, P, S |
| Group 3 (Non-GMP) | $2 \times 10^6$ | V, R, P | V, R, P | V, R, I, P |
| Group 4 (Non-GMP) | $5 \times 10^5$ | V, R, I, P | V, R, P | V, R, P |

V—Viability %,
R—Recovery %,
I—Identity,
P—Potency,
S—Sterility

Two vials from each of the 4 groups of RTA therapeutic cell compositions were concurrently thawed; 1 vial using an automated cell thawing unit (e.g., a ThawSTAR automated thawing system by Sigma-Aldrich) and the second using a standard water bath at about 37° C. Thawed vials were then placed on ice. Each vial was gently pipetted and 2 samples of 20 μl from each vial were taken, diluted in 180 μl of NUTS (−), vortexed and counted. Average viability and recovery percentages were calculated for each thawed vial.

The stability of the RTA therapeutic cell compositions at room temperature post-thawing for up to 4 hours was evaluated by assaying thawed cell compositions for viability, recovery, sterility, potency and identity. Potency was determined by measured TEER, Basal PEDF/VEGF ratio secretion at day 21 and Apical VEGF/PEDF ratio secretion at day 21. Recovery percentages were calculated based on the targeted final concentration of $2\times10^6$ or $5\times10^6$ cells/ml.

The viability and recovery averages of the RTA therapeutic cell compositions which were thawed using an automated cell thawing unit were comparable with those achieved using a conventional water bath at about 37° C., at both cell concentrations, as shown in Table 13.

TABLE 13

Average viability and recovery of RTA therapeutic cell compositions thawed using an automated cell thawing unit vs. thawing using a water bath at about 37° C. at different cell concentrations.

| Thawing Method | Cell Concentration (cell/mL) | Live cells concentration (cell/mL) × $10^6$ | Avg. Viability % | Avg. Recovery % |
|---|---|---|---|---|
| 37° C. Water Bath | $2 \times 10^6$ (n = 2) | 2.32 | 95 | 117 |
| | $5 \times 10^6$ (n = 2) | 4.92 | 95 | 99 |
| Automated Cell Thawing Unit | $2 \times 10^6$ (n = 2) | 2.29 | 95 | 116 |
| | $5 \times 10^6$ (n = 2) | 5.55 | 95 | 112 |

As shown in Table 14, the average percent viability for each group at time points 0, 2, and 4 hours was at least 83%. The average percent recovery of all tested groups was at least about 78% at time points 0, 2, and 4 hours. There was a slight decrease of about 4% to 10% in viability and up to a 17% decrease in recovery of all groups post 2 and 4 hours room temperature incubation. Average recovery of the $5\times10^6$ cell per mL cell concentration was higher than that of the $2\times10^6$ cell per ml concentration at all time points.

TABLE 14

Viability and recovery averages.

| Time Point | Cells + CM (RTA) Group No. | Vial No. | Avg. Viability % per vial | Avg. Recovery % per vial |
|---|---|---|---|---|
| 0 Hours | Group 1 | 1 | 95 | 104 |
| | | 2 | 96 | 99 |
| | Group 2 | 1 | 96 | 115 |
| | Group 3 | 1 | 90 | 117 |
| | Group 4 | 1 | 93 | 90 |
| 2 Hours | Group 1 | 1 | 87 | 84 |
| | Group 2 | 1 | 91 | 107 |
| | Group 3 | 1 | 85 | 117 |
| | Group 4 | 1 | 89 | 78 |
| 4 Hours | Group 1 | 1 | 85 | 91 |
| | Group 2 | 1 | 89 | 112 |
| | Group 3 | 1 | 85 | 107 |
| | | 2 | 83 | 97 |
| | Group 4 | 1 | 89 | 84 |

Figure 24A:
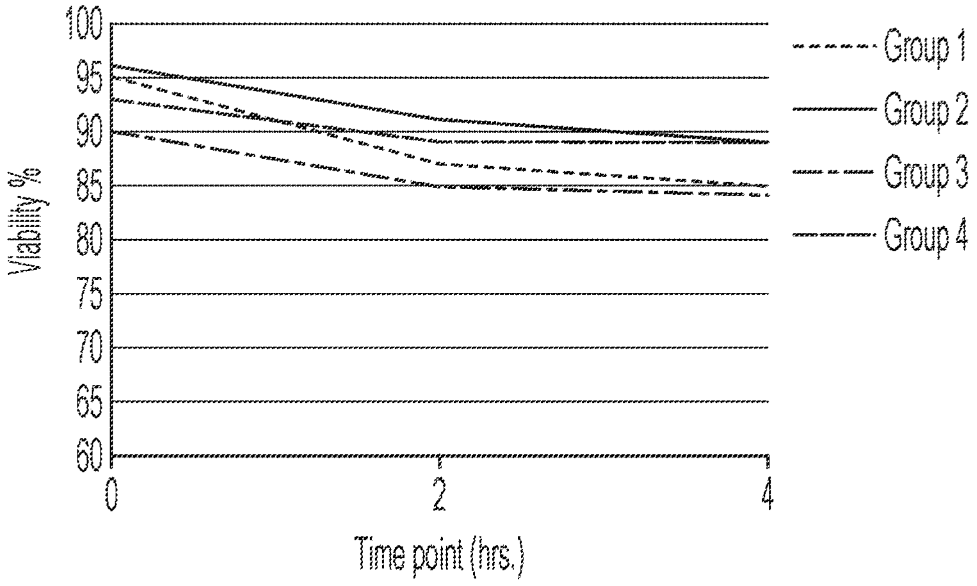
FIG. 24A is a graph showing viability of thawed RTA cell compositions kept at room temperature over a 4-hour period. Cells were tested at time points 0, 2, 4 hrs.
Figure 24B:
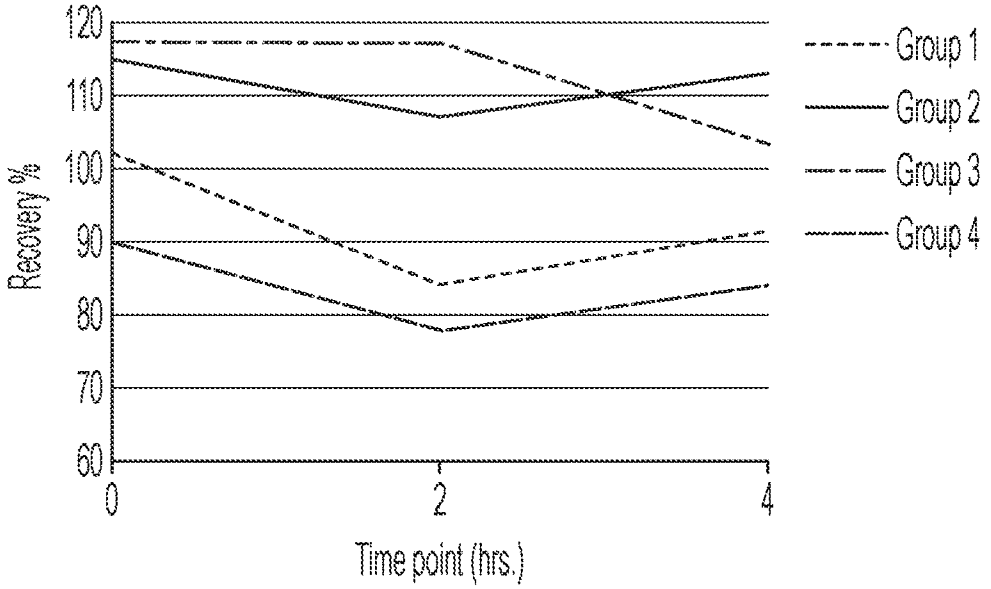
FIG. 24B is a graph showing recovery of thawed RTA cell compositions kept at room temperature over a 4-hour time period. Cells were tested at time points 0, 2, 4 hrs.

FIG. 24A and FIG. 24B are graphs showing the viability and recovery of the thawed RTA cell compositions at room temperature over a 4-hour incubation time.

Example 10

The compatibility of the RTA therapeutic cell compositions with a delivery device was assessed. Examples of delivery devises include but are not limited to devices manufactured by the Dutch Ophthalmic Research Center (D.O.R.C) comprising a needle with an outer diameter of about 0.63 mm and an inner diameter of about 0.53 mm, a capillary with an outer diameter of about 0.5 mm and an inner diameter of about 0.25 mm, and a tip with an outer diameter of about 0.12 mm and an inner diameter of about 0.07 mm. Delivery device released RTA therapeutic cell compositions comprising 4 batches were assayed for viability, recovery and potency following a 2-hour incubation time at RT, post-thawing, using an automated thawing system. All of the RTA cell compositions were formulated as described in Example 6, except for Group 4, in which no filtration step prior to cryopreservation was applied. The results are presented in Table 15.

TABLE 15

Stability of RTA Cell Composition Before Release from Delivery Device

| Time point | Batch ID | Identity assay | Potency assay | | |
|---|---|---|---|---|---|
| | | % CRALBP/ PMEL17 | Net TEER (Ω) (day 14) | PEDF Apical/ Basal Ratio (day 21) | VEGF Basal/ Apical Ratio (day 21) |
| 0 | Group 1 | 99.70 | 605 | 8.31 | 2.06 |
| | Group 2 | NA | 525 | 6.91 | 2.54 |
| | Group 3 | NA | 615 | 7.08 | 1.95 |
| | Group 4 | 98.39 | 322 | 4.30 | 2.77 |
| 2 hrs. | Group 1 | NA | 574 | 9.71 | 2.56 |
| | Group 2 | 98.74 | 536 | 5.20 | 2.15 |
| | Group 3 | NA | 660 | 7.09 | 2.13 |
| | Group 4 | NA | 333 | 5.21 | 2.47 |
| 4 hrs. | Group 1 | NA | 479 | 7.62 | 2.04 |
| | Group 2 | NA | 518 | 4.10 | 2.20 |
| | Group 3 | 98.68 | 605 | 6.51 | 1.99 |
| | Group 4 | NA | 235 | 3.38 | 2.34 |

CRALBP/PMEL17 (identity) values of tested groups (Table 15) were above 98% for all tested batches at all time points. Net TEER values (day 14) remained well above 100Ω in all groups. A gradual decrease was apparent as time progressed, mainly in Groups 1, and 4 after 4 hours. Batches from Group 1 and Group 2 were tested for sterility after 4 hours incubation at Room Temperature and there was no growth detected for both batches.

Compatibility of a delivery device to deliver viable, potent RTA therapeutic cell compositions was evaluated by releasing thawed RTA therapeutic cell compositions, which were incubated at RT for 2 hours, within the delivery device. First and second dose volumes were tested to allow flexibility. Cells were assayed for viability, recovery, and potency. Results for the viability and recovery percentages after being kept at RT for 2 hours before being loading the RTA therapeutic cell compositions into the delivery device.

TABLE 16

Viability and recovery after 2-hours at time at RT (pre-delivery device).

| Batch ID | Avg. Viability % per vial | Avg. Recovery % per vial |
|---|---|---|
| Group 1 | 92 | 91 |
| Group 2 | 91 | 94 |
| Group 3 | 87 | 94 |
| Group 4 | 90 | 76 |

Post-deliver device release viability and recovery percentage of all groups are presented in Table 17. Average viability was between 89% and 95%. Average total recovery across all groups was between about 71% and 94%. There was a slight decrease of up to 8% in recovery of the first 100 μl and up to a 16% decrease in the second 100 μl volume compared with pre-delivery device recovery results (except in Group 2, where recovery remained stable).

TABLE 17

Post-delivery device release cell viability and recovery result.

| Group ID | Cell Conc. | Sample | Avg. Viability % per sample | Avg. Recovery % per sample | Avg. Recovery % per vial |
|---|---|---|---|---|---|
| Group 1 | $2 \times 10^6$ | 100 μl-a | 95 | 84 | 80 |
| | | 100 μl-b | 94 | 75 | |
| Group 2 | $5 \times 10^6$ | 100 μl-a | 91 | 96 | 94 |
| | | 100 μl-b | 92 | 93 | |
| Group 3 | $2 \times 10^6$ | 100 μl-a | 90 | 86 | 84 |
| | | 100 μl-b | 89 | 82 | |
| Group 4 | $5 \times 10^6$ | 100 μl-a | 94 | 73 | 71 |
| | | 100 μl-b | 93 | 69 | |

Group 4 was formulated with no filtration step prior to cryopreservation. Thus, the reduced recovery may relate to cell and extracellular matrix aggregates residing in the delivery device.

Post-delivery device release net TEER (for day 14) values are shown in Table 18. The net TEER values ranged from between about 154Ω to about 435Ω. The results for the PEDF Apical/Basal Ratio (day 21) and VEGF Basal/Apical Ratio (day 21) are also presented in Table 18.

TABLE 18

Post-delivery device release potency results.

| Group ID | Net TEER (Ω) (day 14) | PEDF Apical/Basal Ratio (day 21) | VEGF Basal/Apical Ratio (day 21) |
|---|---|---|---|
| Group 1 | 331 | 6.70 | 1.80 |
| Group 2 | 159 | 4.36 | 1.93 |
| Group 3 | 435 | 5.38 | 1.90 |
| Group 4 | 154 | 2.99 | 2.19 |

Although the TEER values for the $2\times10^6$ cell dosages for Groups 1 and 3 were slightly higher than the TEER values of the $5\times10^6$ cell dosages (Groups 2 and 4), all tested post-delivery device sample groups displayed biological activity, according to potency assay results.

Example 11

Cryoshippers were loaded with liquid nitrogen, prepared for transport and loaded with the batches of cryopreserved RTA therapeutic cell compositions described in Example 10 (Groups 1-4). All of the RTA cell compositions were formulated as described in Example 6, except for Group 4, in which no filtration step prior to cryopreservation was applied. RTA therapeutic cell compositions were shipped from a Jerusalem, Israel to a US-biorepository in Frederick, Maryland, with intermediate storage in the vapor phase of a liquid nitrogen freezer and shipment of the product back to Jerusalem, Israel. The shipments included air and ground transportation of 4 batches (Groups 1-4) stored in a single vapor-phase cryoshipper and was carried out by World Courier. The Cryoshipper provided the required storage conditions of approximately (−196° C.) to (−150° C.) and was monitored by an internal Data Logger. Groups 1-4 were assayed for appearance, viability, recovery, potency and sterility. The results are presented in Table 19.

TABLE 19

Appearance, viability, recovery, potency and sterility of cryoshipped RTA cell compositions.

| | Assay | | | |
|---|---|---|---|---|
| Appearance | Group 1 ($2 \times 10^6$ cells/ml) Homogenous, opaque cell suspension, free of visible foreign particles and non-dissociated aggregates | Group 2 ($5 \times 10^6$ cells/ml) Homogenous, opaque cell suspension, free of visible foreign particles and non-dissociated aggregates | Group 3 ($2 \times 10^6$ cells/ml) Homogenous, opaque cell suspension, free of visible foreign particles and non-dissociated aggregates | Group 4 ($5 \times 10^6$ cells/ml) * Clumps were observed |
| % Viability (Avg.) | 95% | 94% | 91% | 90% |
| % Recovery (Avg.) | 98% | 110% | 108% | 75% |
| TEER (Ω) (day 14) | 672 | 522 | 658 | 395 |
| PEDF Apical/Basal Ratio (day 21) | 7.73 | 8.14 | 7.59 | 4.89 |
| VEGF Basal/Apical Ratio (day 21) | 1.97 | 2.35 | 2.26 | 2.44 |
| 14 days Sterility | No growth | No growth | Not tested | Not tested |

* The clumps were the result of formulation without filtration before fill and finish procedure.

Although the temperature in the cryoshipper did reach to below −196° C., this temperature does not pose a risk to the integrity and quality of the cell composition and is within the calibrated range of liquid nitrogen data loggers.

The results indicate that the stability, quality and integrity of cryopreserved RTA cell compositions formulated in CS5 cryomedium are maintained during controlled shipping from a Jerusalem, Israel to a US-biorepository in Frederick, Maryland, with intermediate storage in the vapor-phase of a liquid nitrogen freezer and shipment of the product back to Jerusalem, Israel.

Example 12

The safety of RTA therapeutic cell compositions comprising RPE cells and cryopreservation solution was assessed following sub-retinal injection into NOD/SCID mice. A total of 40 female NOD/SCID mice at the age of 5-9 weeks were utilized and divided into four (4) groups of 4 or 12 animals in each group (n=1 or 3 for each of the termination time points; 1, 3, 7, and 14 days post administration).

Four compositions were evaluated. Group 1 was administered BSS Plus, Group 2 was administered CS5 cryomedium, Group 3 was administered RTA therapeutic cell composition (comprising RPE cell and CS5), and Group 4 was administered RPE cells in BSS Plus, as shown in Table 20.

TABLE 20

Experimental design.

| Group No. | No. of Animals | Treatment | Dose Volume (μl/mouse) | Cell Concentration | Administration |
|---|---|---|---|---|---|
| 1 | 4 | BSS Plus | 1 μl | N/A | Subretinal |
| 2 | 12 | CS5 | 1 μl | N/A | |
| 3 | 12 | RTA (Cells + CS5) | 1 μl | $5 \times 10^3$ cells/mouse | |
| 4 | 12 | BSS Plus + Cells | 1 μl | $5 \times 10^3$ cells/mouse | |

Animals were observed periodically during the first 24 hours (with special attention given during the first 4 hours post dosing), and daily thereafter, until termination. Observations performed for any changes in local injection site, skin, fur, eyes, mucous membranes, respiratory, occurrence of secretions and excretions (e.g. diarrhea) and autonomic activity (e.g. lacrimation, salivation, piloerection, pupil size, unusual respiratory pattern). Changes in gait, posture and response to handling, as the presence of bizarre behavior, tremors, convulsions, sleep and coma are also included. No observed abnormalities, toxic signs, moribund condition and unscheduled deaths were recorded. Eye examination was performed by veterinary ophthalmologist once during acclimation, and on each termination day. In all right eyes (non-treated) from all groups, no visible lesions (NVL) were observed.

At termination, animals were sacrificed by CO2 asphyxiation and gross pathology was performed examining the local injection site (eyes) including the different eye structures, major tissue and organ systems. Animals were enucleated, including the optic nerve, and fixed in Davidson's solution. All eyes were subject to histopathologic examinations.

Figure 25A:
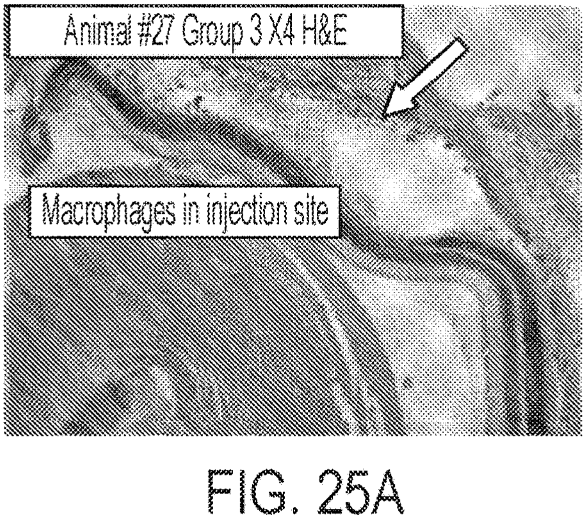
FIG. 25A is a histological image of the treated eye taken from an animal treated with RTA (cells+CS5) and sacrificed on day 14 of the study, showing mild inflammation and a few lose macrophages and lymphocytes. (H&E stained at ×4 magnification field).
Figure 25B:
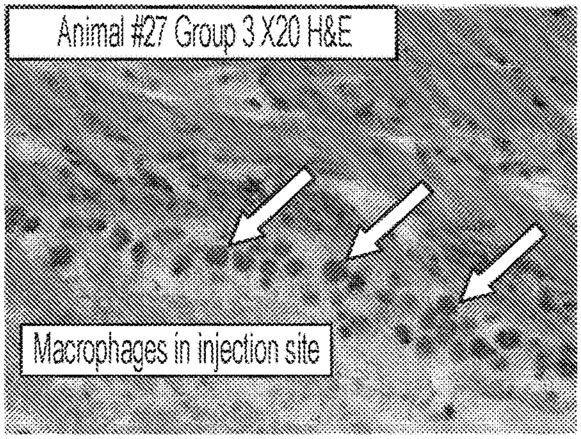
FIG. 25B is a histological image of the treated eye taken from an animal treated with RTA (cells+CS5) and sacrificed on day 14 of the study, showing mild inflammation and a few lose macrophages and lymphocytes. (H&E stained at ×20 magnification field).

Histopathologic evaluation revealed the presence of macrophage infiltration in a few cell-treated animals from Groups 3 and 4, on Days 3 and 14 (1 of 3 animals in each termination day and group). These findings are probably due to a late immune response to the injection of human RPE cells. However, most animals in the cell-treated groups (20/24) did not show any immune response to the transplanted cells. In Groups 1 and 2, which were not treated with cells, neutrophils were observed on Days 1, 3 and 7 (in 3 animals). Neutrophils are common in early stages of the immune response, while the lack of macrophages indicate no late response. Except for the appearance of macrophages in a few of the cells-treated mice (4/24), all groups displayed similar pathologies, indicating that the findings were most likely related to a procedure-induced inflammation. FIG. 25A and FIG. 25B are representative histological images at ×4 and ×20 magnification, respectively, showing mild inflammation in an animal treated with RTA formulation (cells+CS5). Based on the collected data, there were no major treatment-related and/or toxicologically significant effects following the sub-retinal administration of the therapeutic cell compositions as compared to the vehicle after 10 days follow-up.

Example 13

To evaluate the comparability of RTA RPE therapeutic cell compositions formulated during different manufacturing runs, several batches were prepared. hESCs were mechanically passaged by first thawing at least one ampule of hESCs. Post thawing, 10 fragments retrieved from the ampule, were seeded on two Center Well (CW) plates containing a monolayer of irradiated human cord derived feeder cells and incubated in 'NutriStem Plus'+HSA medium (or equivalent) at 37° C./5% $CO_2$ (1 ampule→2 CW with 10 colony fragments).

hESC colonies were expanded and passaged once a week for about 3 more weeks until reaching a total of 45 center well plates. Colonies were then transferred to 6 cm plates with feeders at a ratio of about 2:1 (2 CW→6 cm plate) and cultured for about 6 days in 'NutriStem Plus'+HSA medium at 37° C./5% $CO_2$.

To form spheroid bodies (SBs) and start the RPE directed differentiation process, hESC colonies were collected from the 6 cm plates and transferred to plates (such as Hydrocell™ (Nunc)) (non-adherent surface) at a ratio of about 5:1 (5×6 cm plate 4 μlate) and cultured for about 1 week in 'NutriStem Minus' medium supplemented with Nicotinamide at 37° C./5% $CO_2$/5% $O_2$. About one week after SB formation, SBs were collected and broken down to smaller fragments by pipetting. SB fragments were seeded on 6 well plates coated with Laminin 511 (BioLamina, Stockholm, Sweden) or an equivalent and cultured in the presence of Nicotinamide and Activin A (combination of Nicotinamide and Activin A varied according to the differentiation to stage) for about 5 weeks in NuriStem Minus or equivalent at about 37° C./5% $CO_2$/5% $O_2$ and about 1 week at 37° C./5% $CO_2$. At the end of the differentiation stage, pigmented cells were enriched enzymatically and transferred to recombinant human Gelatin coated T175 (175 $cm^2$) flasks (P0) and incubated in NutriStem Minus (20% human serum/DMEM for the first 2-3 days) at 37° C./5% $CO_2$.

Cells may be harvested around day 14 and passaged to rh-Gelatin coated T175 flasks and incubated in NutriStem Minus (20% human serum/DMEM for the first 2-3 days) at about 37° C./5% $CO_2$ (P1). Cells were harvested on day 12 and passaged to rh-Gelatin coated T175 flasks and incubated in NutriStem Minus (20% human serum/DMEM for the first 2-3 days) at 37° C./5% $CO_2$ (P2).

On day 10 post P2 passage, the T175 flasks were harvested, filtered using sequential tandem of 500-200-40 μm cell strainer system and then pooled. The total number of cells at this point can be at least about 551×$10^6$ cells. Cells were centrifuged and resuspended in cryomedium (such as CryoStor 5 (BioLife Solutions Inc., Bothell, WA) for example) and counted to reach a final concentration of about 1×$10^6$ cell/ml, about 2×$10^6$ cell/ml, about 3×$10^6$ cell/ml, about 4×$10^6$ cell/ml, about 5×$10^6$ cell/ml, about 6×$10^6$ cell/ml, about 7×$10^6$ cell/ml, about 8×$10^6$ cell/ml, or about 9×$10^6$ cell/ml. This cell suspension can be kept at 2-8° C. until it is dispensed into cryovials. The RTA therapeutic cell composition can then by cryopreserved using a controlled-rate freezer and then transferred to vapor-phase LN2 freezer. Examples of freezing profiles that may be used include:

Wait at 4° C.
Hold for 1 minute at 4° C.
1.00° C./minute Sample to −11° C.
30.00° C./minute Chamber to −50° C.
15.00° C./minute Chamber to −25° C.
1.00° C./minute Chamber to −50° C.
10.00° C./minute Chamber to −90° C.
End or Wait at 4° C.
1.00° C./minute Sample to −4° C.
25.00° C./minute Chamber to −40° C.
10.00° C./minute Chamber to −12° C.
1.00° C./minute Chamber to −40° C.
10.00° C./minute Chamber to −90° C.
End Table 21 provides morphology and purity results of the hESCs as they are expanded, differentiated into RPE cells and expanded as RPE cells. As shown in Table 21, the hESCs were successfully expanded and differentiated using the process described above.

TABLE 21

Analysis of cells during the expansion and differentiation phases for RTA Batch A

| Step | Test | Result |
|---|---|---|
| End of hESCs expansion | Morphology assessment | 70% |
| | Pluripotent Markers analysis (TRA-1-60+/OCT4+) | 66.16% |
| End of differentiation/ Enzymatic Isolation | Purity (CRALBP+/PMEL17+) | 26.77% |
| End of P0 (RPE expansion start) | Purity (CRALBP+/PMEL17+) | 88.95% |
| End of P1 (RPE expansion middle) | Purity (CRALBP+/PMEL17+) | 98.85% |
| | hESC impurities (TRA-1-60+/OCT4+) | 0.00000% BLOD |
| End of P2 (RPE expansion end) | Morphology assessment | Confluent and polygonal |
| | Purity (CRALBP+/PMEL17+) | 98.37% |

In addition, percent viability, cell concentration, percent recovery, and purity were determined for Batch A. Results are presented in Table 22.

TABLE 22

Percent viability, cell concentration, percent recovery, and purity for RTA Batch A

| Test | Result |
|---|---|
| Viability ± S.E | 95% ± 0.97% |
| Total cells/1 mL ± S.E | $2.36 \times 10^6$ ± $5.86 \times 10^4$ |
| % Recovery ± S.E | 118% ± 2.93% |
| Purity (CRALBP+/PMEL17+) | 98.74% |
| hESC impurities (TRA-1-60+/OCT4+) | 0.00000% BLOD |

Additional batches were produced and analyzed as described for Batch A. The cell dose for each Batch is shown in Table 23.

TABLE 23

Cell doses for each Batch

| Batch ID | Cell Dose |
|---|---|
| Batch B | $5 \times 10^6$ cells/ml |
| Batch C | $5 \times 10^6$ cells/ml |
| Batch D | $2 \times 10^6$ cells/ml |
| Batch E | $2 \times 10^6$ cells/ml |
| Batch F | $5 \times 10^6$ cells/ml |

Results for Batches B-F are presented in Table 24 and Table 25.

TABLE 24

Morphology, sterility, and purity for Batches B-F

| Step | Test | | Result |
|---|---|---|---|
| End of hESCs expansion | Morphology assessment | | 70% |
| | Sterility | | No Growth |
| | Mycoplasma | | No Growth |
| | Endotoxin | | <3.84 EU/ml |
| | Pluripotent Markers Analysis (TRA-1-60+/OCT4+) | | 78.30% |
| End of P1 (middle of RPE expansion) | Purity (CRALBP+/PMEL17+) | | 99.76% |
| | hESC impurities (TRA-1-60+/OCT4+) | | Not Detected |
| End of P2 (end of RPE expansion) | Morphology assessment | | Confluent and polygonal |
| | Purity (CRALBP+/PMEL17+) | | 99.81% |
| | Sterility* | Batch B | No Growth |
| | | Batch C | No Growth |
| | | Batch D | No Growth |
| | | Batch E | No Growth |
| | | Batch F | No Growth |
| | Mycoplasma* | Batch B | No Growth |
| | | Batch C | No Growth |
| | | Batch D | No Growth |
| | | Batch E | No Growth |
| | | Batch F | No Growth |
| | Endotoxin (LAL)* | Batch B | 0.03 EU/ml |
| | | Batch C | 0.03 EU/ml |
| | | Batch D | 0.03 EU/ml |
| | | Batch E | 0.03 EU/ml |
| | | Batch F | 0.03 EU/ml |

*Cell composition tested

TABLE 25

Percent viability, cell concentration, percent recovery, purity, sterility, PEDF secretion and VEGF secretion for Batches B-F

| Batch ID | Test | Result |
|---|---|---|
| Batch B | Percent Viability ± SE | 95% ± 0.46% |
| Batch C | | 95% ± 0.37% |
| Batch D | | 96% ± 1.15% |
| Batch E | | 97% ± 0.22% |
| Batch F | | 96% ± 0.25% |
| Batch B | Total cells/1 mL ± SE | $5.56 \times 10^6 \pm 1.38 \times 10^5$ |
| Batch C | | $5.37 \times 10^6 \pm 2.53 \times 10^5$ |
| Batch D | | $1.89 \times 10^6 \pm 1.08 \times 10^5$ |
| Batch E | | $2.25 \times 10^6 \pm 8.74 \times 10^4$ |
| Batch F | | $5.81 \times 10^6 \pm 6.90 \times 10^4$ |
| Batch B | Percent Recovery ± SE | 107% ± 2.23% |
| Batch C | | 102% ± 5.17% |
| Batch D | | 91% ± 5.92% |
| Batch E | | 109% ± 3.89% |
| Batch F | | 112% ± 1.44% |
| Batch B | Purity (CRALBP+/PMEL17+) | 99.10% |
| Batch C | | 99.36% |
| Batch D | | 99.39% |
| Batch E | | 99.52% |
| Batch F | | 99.40% |
| Batch B | hESC impurities (TRA-1-60+/OCT4+) | Not Detected |
| Batch B | Sterility | No Growth |
| Batch C | | No Growth |
| Batch D | | No Growth |
| Batch E | | No Growth |
| Batch F | | No Growth |
| Batch B | PEDF secretion (ng/ml/day)-Day 7 | 477.77 |
| | VEGF secretion (ng/ml/day)-Day 7 | 1.59 |
| | PEDF secretion (ng/ml/day)-Day 14 | 2458 |
| | VEGF secretion (ng/ml/day)-Day 14 | 5.90 |

TABLE 25-continued

| Percent viability, cell concentration, percent recovery, purity, sterility, PEDF secretion and VEGF secretion for Batches B-F | | |
|---|---|---|
| Batch ID | Test | Result |
| Batch C | PEDF secretion (ng/ml/day)-Day 7 | 688.18 |
| | VEGF secretion (ng/ml/day)-Day 7 | 1.97 |
| | PEDF secretion (ng/ml/day)-Day 14 | 2040 |
| | VEGF secretion (ng/ml/day)-Day 14 | 5.14 |
| Batch D | PEDF secretion (ng/ml/day)-Day 7 | 614.22 |
| | VEGF secretion (ng/ml/day)-Day 7 | 1.61 |
| | PEDF secretion (ng/ml/day)-Day 14 | 2468 |
| | VEGF secretion (ng/ml/day)-Day 14 | 5.68 |
| Batch E | PEDF secretion (ng/ml/day)-Day 7 | 481.75 |
| | VEGF secretion (ng/ml/day)-Day 7 | 1.28 |
| | PEDF secretion (ng/ml/day)-Day 14 | 2117 |
| | VEGF secretion (ng/ml/day)-Day 14 | 5.20 |
| Batch F | PEDF secretion (ng/ml/day)-Day 7 | 200.21 |
| | VEGF secretion (ng/ml/day)-Day 7 | 0.79 |
| | PEDF secretion (ng/ml/day)-Day 14 | 2016 |
| | VEGF secretion (ng/ml/day)-Day 14 | 4.44 |

As shown in Table 24 and Table 25, the formulation method of RTA RPE therapeutic cell compositions is reproducible and robust with regard to cell morphology, sterility, purity, percent viability, cell concentration, percent recovery, PEDF secretion and VEGF secretion (potency).

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method of treating a retinal degenerative disease in a human subject in need thereof, comprising thawing a frozen retinal pigment epithelium (RPE) cell therapy composition and administering the thawed RPE cell therapy composition to the retina of the subject directly after thawing without washing, reconstitution, or removal of dead cells; wherein the RPE cell therapy composition comprises:

a) a preservation media comprising: adenosine, dextran-40, HEPES (N-(2-hydroxyethyl) piperazine-N'-(2-ethanesulfonic acid)), and between about 4% and about 6% dimethyl sulfoxide (DMSO); and b) retinal pigment epithelium (RPE) cells.

2. The method of claim 1, wherein the RPE cell therapy composition comprises between about 100,000 and about 10,000,000 RPE cells/mL.

3. The method of claim 1, wherein the RPE cell therapy composition comprises between about 2,000,000 and about 5,000,000 RPE cells/mL.

4. The method of claim 1, wherein the preservation media comprises about 5% DMSO.

5. The method of claim 1, wherein the preservation media further comprises one or more of: a sugar acid, one or more of a base, an antioxidant, one or more halide salt, a basic salt, phosphate salt, one or more sugars, sugar alcohol, and water.

6. The method of claim 5, wherein:

a) the sugar acid comprises lactobionic acid, glyceric acid, xylonic acid, gluconic acid, ascorbic acid, neuraminic acid, ketodeoxyoctulosonic acid, glucuronic acid, galacturonic acid, galacturonic acid, iduronic acid, tartaric acid, mucic acid, or saccharic acid;

b) the one or more of a base comprises sodium hydroxide, or potassium hydroxide;

c) the antioxidant comprises L-glutathione, ascorbic acid, lipoic acid, uric acid, a carotene, alpha-tocopherol, or ubiquinol;

d) the one or more halide salt comprises potassium chloride, sodium chloride, or magnesium chloride;

e) the basic salt comprises potassium bicarbonate, sodium bicarbonate, or sodium acetate;

f) the phosphate salt comprises potassium phosphate, sodium phosphate, or potassium phosphate;

g) the one or more sugars comprises dextrose or sucrose; and h) the sugar alcohol comprises mannitol, sorbitol, erythritol or xylitol.

7. The method of claim 4, wherein the preservation media further comprises lactobionic acid, sodium hydroxide, L-glutathione, potassium chloride, potassium bicarbonate, potassium phosphate, dextrose, sucrose, mannitol, calcium chloride, magnesium chloride, potassium hydroxide, sodium hydroxide, and water.

8. The method of claim 1, wherein the preservation media further comprises one or more of a rho kinase (ROCK) inhibitor or nicotinamide (NA).

9. The method of claim 4, wherein the preservation media further comprises one or more of a rho kinase (ROCK) inhibitor or nicotinamide (NA).

10. The method of claim 1, wherein the RPE cells express one or more of: bestrophin 1, microphthalmia-associated transcription factor (MITF), ZO-1, paired box gene 6 (PAX-6), cellular retinaldehyde binding protein (CRALBP), melanocytes lineage-specific antigen GP100 (PMEL 17), RPE65, and markers for RPE primary cilia.

11. The method of claim 1, wherein the RPE cells secrete one or more of basic fibroblast growth factor (bFGF), acidic fibroblast growth factor (aFGF), ciliary neurotrophic factor (CNTF), pigment epithelium-derived factor (PEDF), brain-derived neurotrophic factor (BDNF), vascular endothelial growth factor (VEGF) or one or more anti-inflammatory cytokines.

12. The method of claim 1, wherein the RPE cells are in a single-cell suspension.

13. The method of claim 1, wherein at least about 40% to about 100% of the RPE cells are viable after thawing without washing, reconstituting, or removing dead cells.

14. The method of claim 13, wherein about 95% to about 100% of viable RPE cells are CRALBP+/PMEL17+ after thawing.

15. The method of claim 4, wherein at least about 40% to about 100% of the RPE cells are viable after thawing without washing, reconstituting, or removing dead cells.

16. The method of claim 15, wherein about 95% to about 100% of viable RPE cells are CRALBP+/PMEL17+ after thawing.

17. The method of claim 1, wherein the RPE cells were generated from pluripotent stem cells.

18. The method of claim 17, wherein the pluripotent stem cells are embryonic stem cells.

* * * * *